US009186365B2

(12) United States Patent
Zudaire et al.

(10) Patent No.: US 9,186,365 B2
(45) Date of Patent: Nov. 17, 2015

(54) ANTIANGIOGENIC SMALL MOLECULES AND METHODS OF USE

(75) Inventors: Enrique Zudaire, Germantown, MD (US); Marta Aparicio, Rockville, MD (US); Frank Cuttitta, Adamstown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 31 days.

(21) Appl. No.: 13/387,969

(22) PCT Filed: Jul. 30, 2010

(86) PCT No.: PCT/US2010/043998
§ 371 (c)(1),
(2), (4) Date: Jan. 30, 2012

(87) PCT Pub. No.: WO2011/014825
PCT Pub. Date: Feb. 3, 2011

(65) Prior Publication Data
US 2012/0129775 A1 May 24, 2012

Related U.S. Application Data

(60) Provisional application No. 61/230,667, filed on Jul. 31, 2009.

(51) Int. Cl.
| | | |
|---|---|---|
| *A61K 38/12* | (2006.01) | |
| *A61K 31/63* | (2006.01) | |
| *A61K 31/135* | (2006.01) | |
| *A61K 31/4015* | (2006.01) | |
| *A61K 31/5365* | (2006.01) | |
| *A61K 31/285* | (2006.01) | |
| *A61K 31/555* | (2006.01) | |

(52) U.S. Cl.
CPC ............... *A61K 31/63* (2013.01); *A61K 31/135* (2013.01); *A61K 31/285* (2013.01); *A61K 31/4015* (2013.01); *A61K 31/5365* (2013.01); *A61K 31/555* (2013.01); *A61K 38/12* (2013.01)

(58) Field of Classification Search
CPC .. A61K 31/135; A61K 31/136; A61K 31/337
USPC .............. 514/13.3, 188, 229.5, 504
See application file for complete search history.

(56) References Cited

U.S. PATENT DOCUMENTS

| 6,756,388 B1 | 6/2004 | Cameron et al. | |
| 2011/0110886 A1* | 5/2011 | Braddock | 424/85.2 |

FOREIGN PATENT DOCUMENTS

| EP | 0011277 | 5/1980 | | |
| EP | 0 031 430 | 7/1981 | | |
| EP | 1583522 | 10/2008 | | |
| EP | 1319000 | 11/2008 | | |
| JP | 2004-509890 | 4/2004 | | |
| WO | WO 99/65495 | * 12/1999 | ........... | A61K 31/535 |
| WO | WO 2008/027912 | 3/2008 | | |
| WO | WO 2009/151644 A2 | 12/2009 | | |

OTHER PUBLICATIONS

Yoshida et al.; Title: Suppression of retinal neovascularization by the NF-κB inhibitor pyrrolidine dithiocarbanate in mice; IOVS, Jun. 1999, vol. 4, No. 7, pp. 1624-1629.*
Gura et al; Title: Systems for identifying new drugs are aften faulty; Science, vol. 278, pp. 1041-1042, Nov. 1997.*
Auerbach et al.; Title: Angiogenesis assays: Problem and pitfalls; Cancer and Metas. Reviews, vol. 19, pp. 167-172, 2000; Khwer Academic Publisher.*
Unknown author; Title: Cilical aspects of cancer; The Merck mannual, May 3, 2008. Jain R; Title: Barriers to drug delivery in solid tumors; Scitific American, Jul. 1994.*
Karin et al., Title: NF-κB: Linking inflammation and Immunity to cancer development and progress, Nature Reviews: Immunology, vol. 5, pp. 749-759, published Oct. 2005.*
Griffioen et al., "Therapeutic Approaches of Angiogenesis Inhibition: Are We tackling the Problem at the Right Level?" *Trends in Cardiovascular Medicine (TCM)*, vol. 17, No. 5, pp. 171-176, Jul. 1, 2007.
Koizumi et al., "Metronomic scheduling of a cyclic hexapeptide Ra-VII for anti-angiogenesis, tumor vessel maturation and anti-tumor activity," *Cancer Science*, vol. 97, No. 7, pp. 665-674, Jul. 1, 2006.
Extended European Search Report issued by the European Patent Office on Nov. 16, 2012, for corresponding European Patent Application No. EP 10 80 5140, 16 pp.
Bergers et al., "Modes of Resistance to Antiangiogenic Therapy," *Nature Reviews*, 8: 592-603, 2008.
Blower et al, "Decision Tree Methods in Pharmaceutical Research," *Current Topics in Medicinal Chemistry*, 6(1): 1-9, 2006.
Blower et al., "Comparison of Methods for Sequential Screening of Large Compound Sets," *Combinatorial Chemistry & High Throughput Screening*, 9(2): 1-8, 2006.
Blower et al., "On Combining Recursive Partitioning and Simulated Annealing to Detect Groups of Biologically Active Compounds," *J. Chem. Inf. Comput. Sci.*, 42(2): 393-404, 2002.
Blower et al., "Pharmacogenomic Analysis: Correlating Molecular Substructure Classes with Microarray Gene Expression Data," *The Pharmaceutical Journal*, 2: 259-271, 2002.
Blower et al., "Systematic Analysis of Large Screening Sets in Drug Discovery," *Current Drug Discovery Technologies*, 1(1): 37-47, 2004.
Chau et al., "Identification of Novel Small Molecule Inhibitors of Hypoxia-Inducible Factor-1 That Differentially Block Hypoxia-Inducible Factor-1 Activity and Hypoxia-Inducible Factor-1 α Induction in Response to Hypoxic Stress and Growth Factors," *Cancer Res.*, 65(11): 4918-4928, 2005.
Cross et al., "Finding Discriminating Structural Features by Reassembling Common Building Blocks," *J. Med. Chem.*, 46(22): 4770-4775, 2003.
Ebos et al., "Accelerated Metastasis After Short-Term Treatment with a Potent Inhibitor of Tumor Angiogenesis," *Cancer Cell*, 15: 232-239, 2009.

(Continued)

*Primary Examiner* — Johann R Richter
*Assistant Examiner* — Yanzhi Zhang
(74) *Attorney, Agent, or Firm* — Klarquist Sparkman, LLP

(57) ABSTRACT

Methods of inhibiting undesired angiogenesis are provided, which methods include administering to a subject a therapeutically effective amount of at least one of the compounds described herein, or a pharmaceutically acceptable salt thereof.

4 Claims, 27 Drawing Sheets

(56) References Cited

OTHER PUBLICATIONS

Fligner et al., "A Modification of the Jaccard-Tanimoto Similarity Index for Diverse Selection of Chemical Compounds Using Binary Strings," *Technometrics*, pp. 1-10, 2002.

Pàez-Ribes et al., "Antiangiogenic Therapy Elicits Malignant Progression of Tumors to Increased Local Invasion and Distant Metastasis," *Cancer Cell*, 15: 220-231, 2009.

Saunders et al., "Identification of Small-Molecule Inhibitors of Autotaxin That Inhibit Melanoma Cell Migration and Invasion," *Mol. Cancer Ther.*, 7(10):3352-3362, 2008.

Wang et al., "Synthesis and Biologic Properties of Hydrophilic Sapphyrins, a New Class of Tumor-Selective Inhibitors of Gene Expression," *Molecular Cancer*, 6(9): 12 pages, 2007.

Willett, Peter, "Chemical Similarity Searching," *J. Chem. Inf. Comput. Sci.*, 38(6): 993-996, 1998.

Xia et al., "Identification of Small Molecule Compounds That Inhibit the HIF-1 Signaling Pathway," *Molecular Cancer*, 8(117): 13 pages, 2009.

Atanasov et al., "Inhibition of 11β-hydroxysteroid dehydrogenase type 2 by dithiocarbamates," *Biochemical and Biophysical Research Communications*, 308:257-262, 2003.

Moon et al., "PDT, Metal Chelating Compound, Induces G1 Phase Cell Cycle Arrest in Vascular Smooth Muscle Cells Through Inducing $p21^{Cip1}$ Expression: Involvement of p38 Mitogen Activated Protein Kinase," *Journal of Cellular Physiology*, 198:310-323, 2004.

Nobel et al., "Dithiocarbamates Induce Apoptosis in Thymocytes by Raising the Intracellular Level of Redox-active Copper," *The Journal of Biological Chemistry*, 270(44):26202-26208, Nov. 3, 1995.

Tsai et al., "Induction of Apoptosis by Pyrrolidinedithiocarbamate and N-Acetylcysteine in Vascular Smooth Muscle Cells," *The Journal of Biological Chemistry*, 271(7):3667-3670, Feb. 16, 1996.

Kim et al., "Prryolidine Dithiocarbamate Induces Bovine Cerebral Endothelial Cell Death by Increasing the Intracellular Zinc Level," *Journal of Neurochemistry*, 72(4):1586-1592, 1999.

Aoki et al., "Endothelial Apoptosis Induced by Oxidative Stress Through Activation of NF-κB: Antiapoptotic Effect of Antioxidant Agents on Endothelial Cells," *Hypertension*, 38:48-55, 2001.

Huang et al., "7-Ketocholesterol Induces Cell Apoptosis by Activation of Nuclear Factor kappa B in Mouse Macrophages," *Acta Med. Okayama*, 64(2):85-93, 2010.

Kisseleva et al., "NF-κB regulation of endothelial cell function during LPS-induced toxemia and cancer," *The Journal of Clinical Investigation*, 116(11):2955-2963, 2006.

Tabruyn et al., "A new role for NF-κB in angiogenesis inhibition," *Cell Death and Differentiation*, 14:1393-1397, 2007.

Tabruyn et al., "NF-κB: a new player in angiostatic therapy," *Angiogenesis*, 11:101-106, 2008.

Tabruyn et al., "NF-κB activation in endothelial cells is critical for the activity of angiostatic agents," *Molecular Cancer Therapeutics*, 8:2645-2654, 2009.

Wang et al., "Activation of nuclear factor-κB during doxorubicin-induced apoptosis in endothelial cells and myocytes is pro-apoptotic: the role of hydrogen peroxide," *Biochem. J.*, 367:729-740, 2002.

Aurora et al., "NF-κB balances vascular regression and angiogenesis via chromatin remodeling and NFAT displacement," *Blood*, 116:475-484, 2010.

"Nuclear Extraction Protocol," *Life Technologies*, pp. 1-3, Jun. 13, 2013.

Cho et al., "Reactive Oxygen Species-Induced Apoptosis and Necrosis in Bovine Corneal Endothelial Cells," *Investigative Ophthalmology & Visual Science*, 40(5):911-919, Apr. 1999.

Hida et al., "Nuclear factor-κB and caspases co-operatively regulate the activation and apoptosis of human macrophages," *Immunology*, 99:553-560, 2000.

Kwang et al., "Novel Biphasic Effect of Pyrrolidine Dithiocarbamate on Neuronal Cell Viability is Mediated by the Differential Regulation of Intracellular Zinc and Copper Ion Levels, NF-κB, and MAP Kinases," *Journal of Neuroscience Research*, 59:117-125, 2000.

Sunderkotter et al., "Macrophages and angiogenesis," *Journal of Leukocyte Biology*, 55:410-422, Mar. 1994.

Woods et al., "Activation of NF-κB in Normal Rat Kidney Epithelial (NRK52E) Cells is Mediated via a Redox-Insensitive, Calcium-Dependent Pathway," *Toxicology and Applied Pharmacology*, 154:219-227, 1991.

Orlowski et al, "NF-κB as a therapeutic target in cancer," *Trends in Molecular Medicine*, vol. 8, No. 8, pp. 385-389, 2002.

\* cited by examiner

Half maximal inhibitory concentration (IC50) in PAE

Data Reduction and Hit Definition

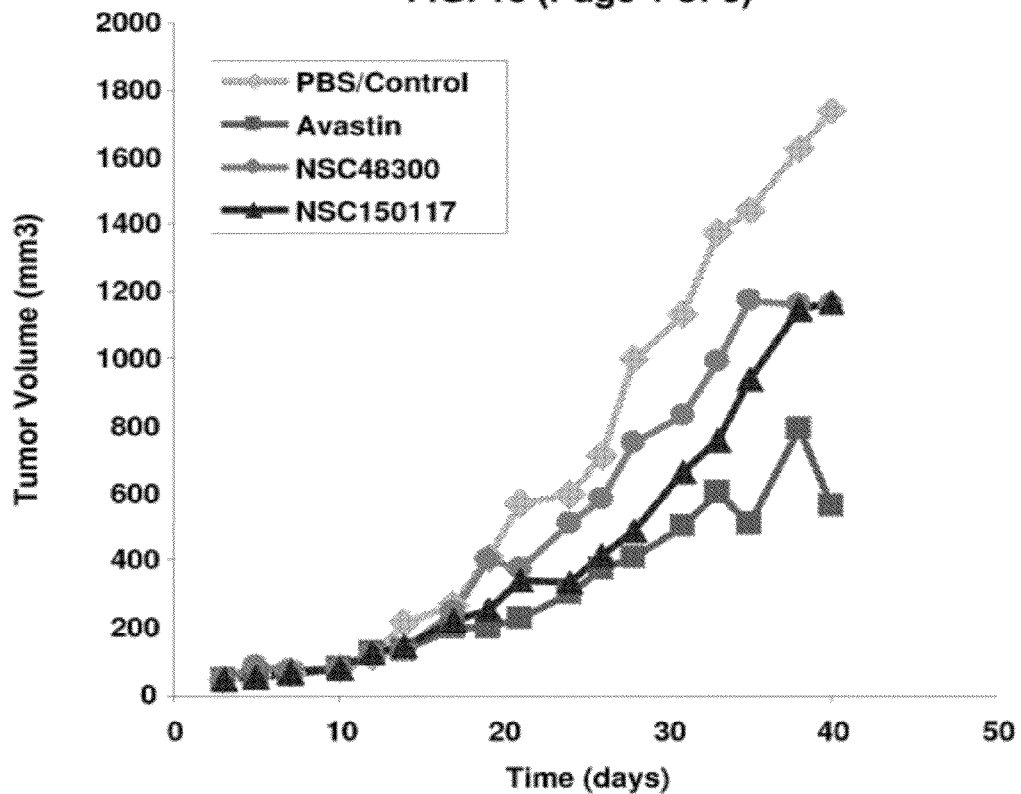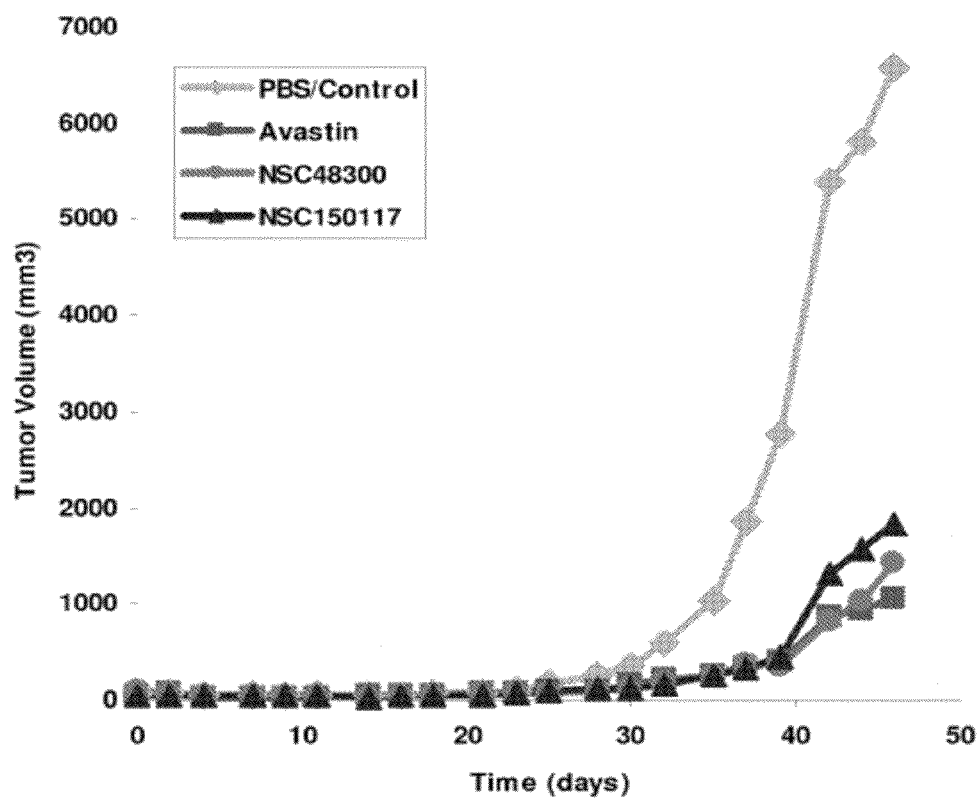
FIG. 15 (Page 1 of 3)

FIG. 15 (Page 2 of 3)
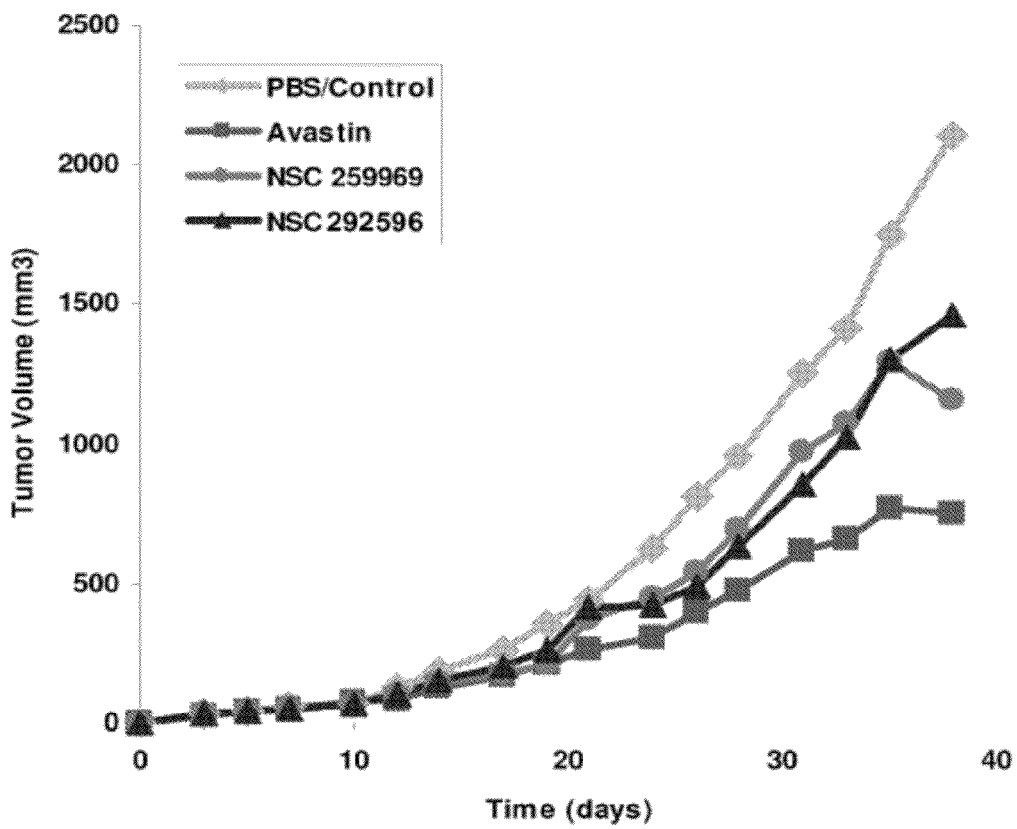
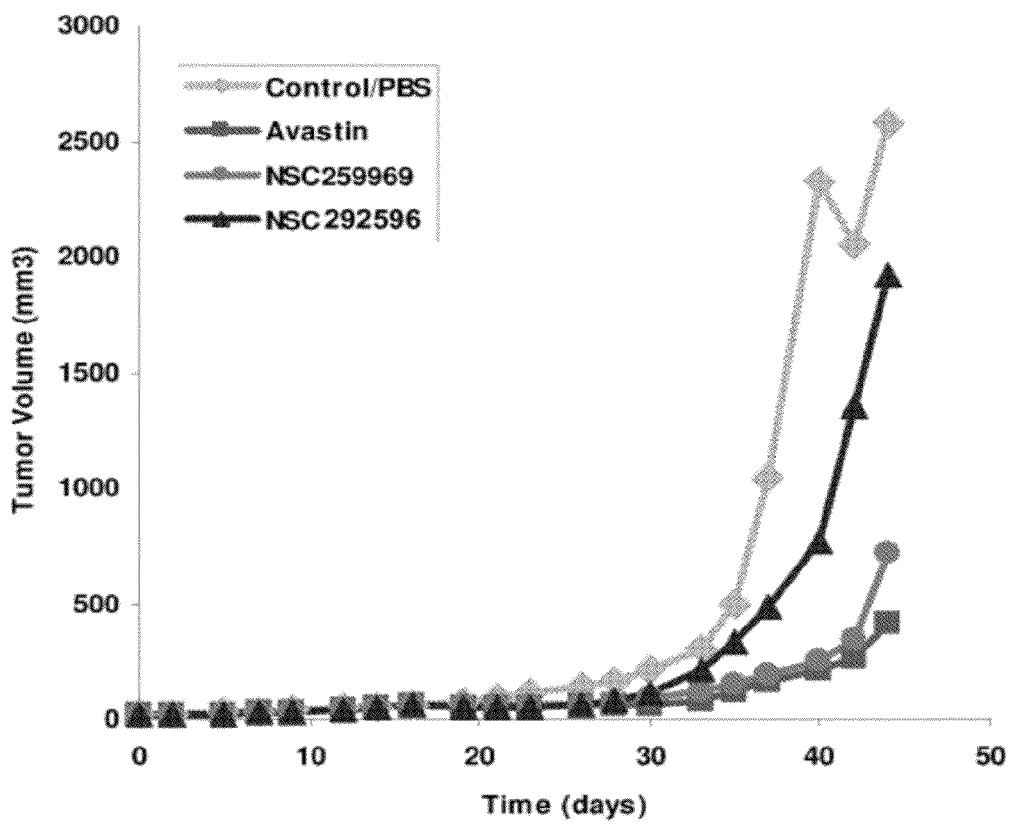

FIG. 15 (Page 3 of 3)
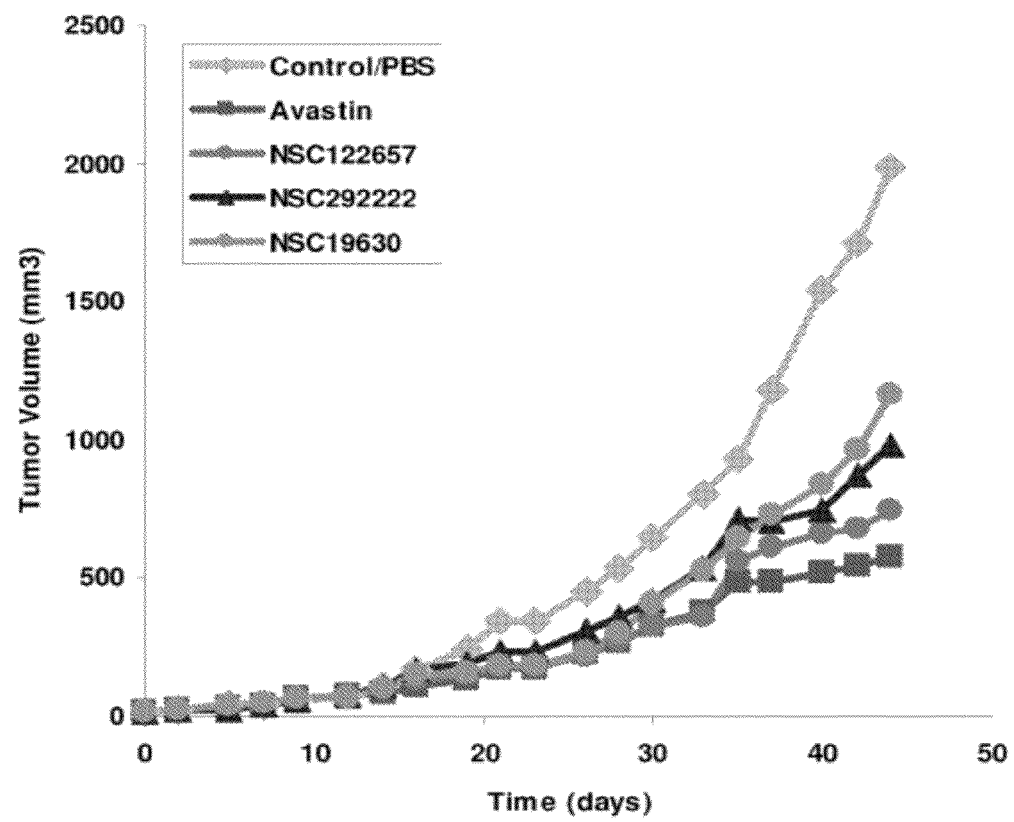
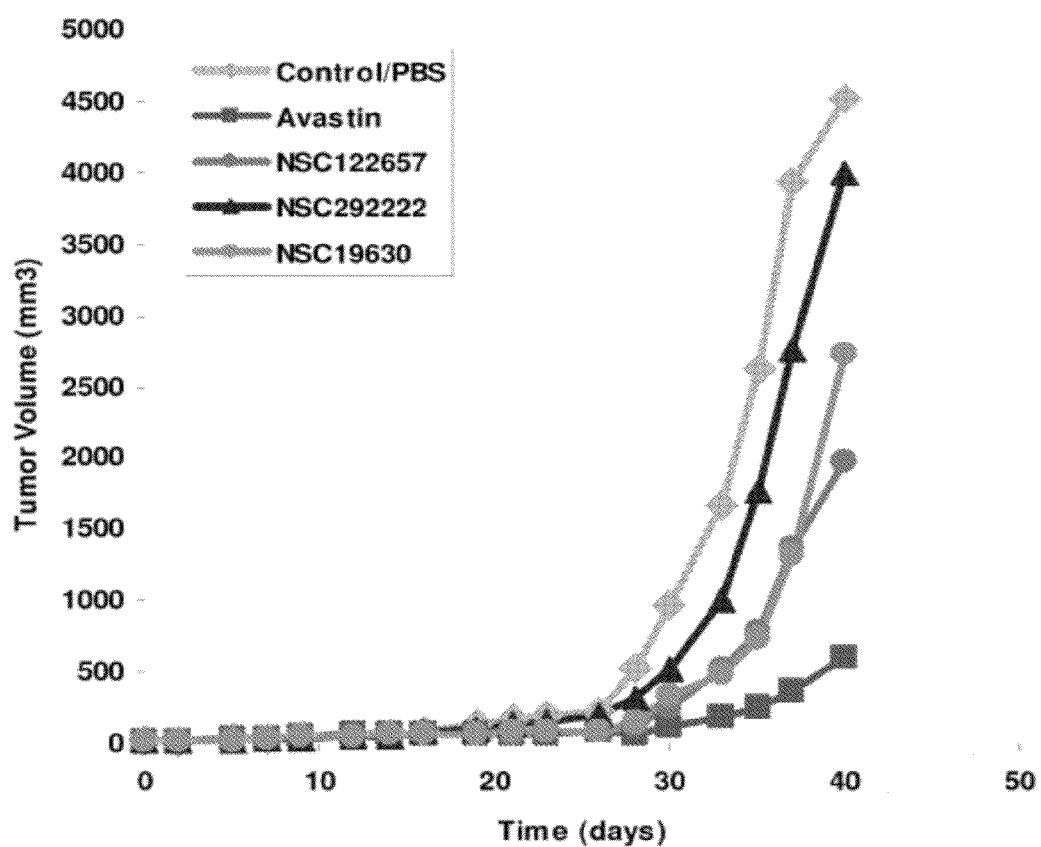

FIG. 16 (Page 1 of 4)
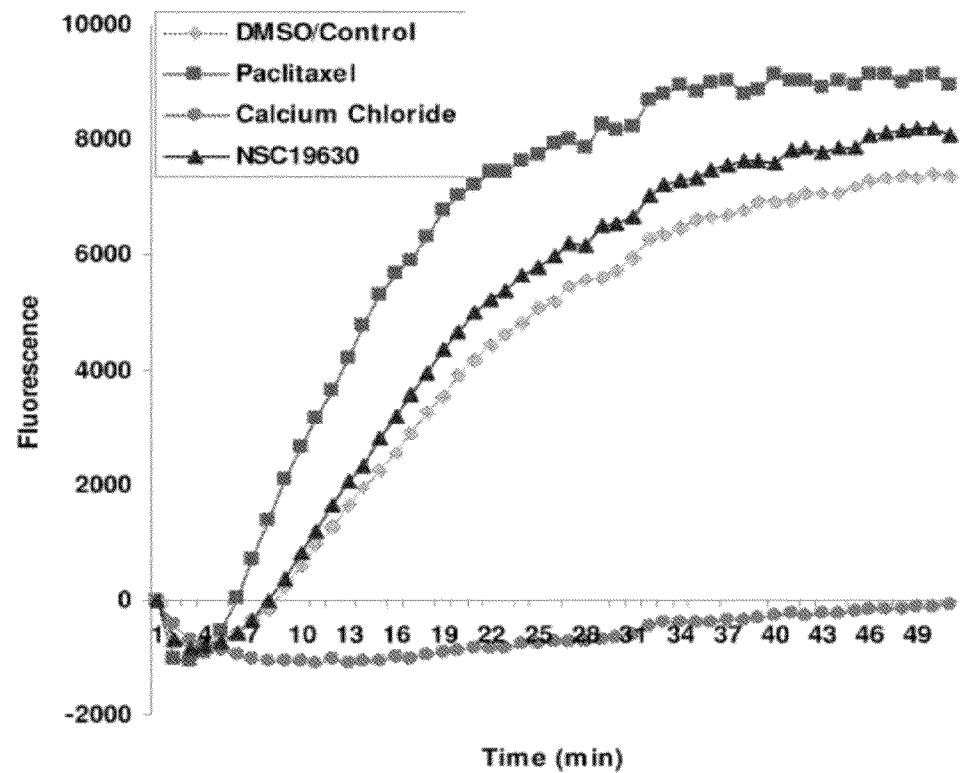
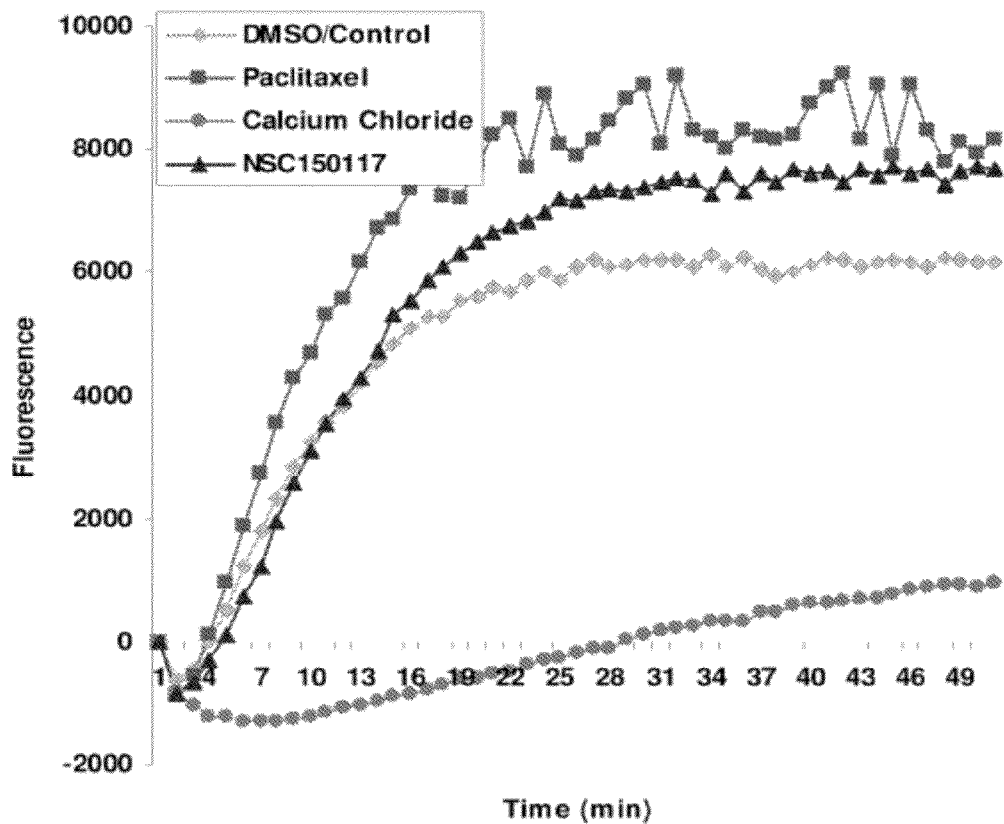

FIG. 16 (Page 2 of 4)
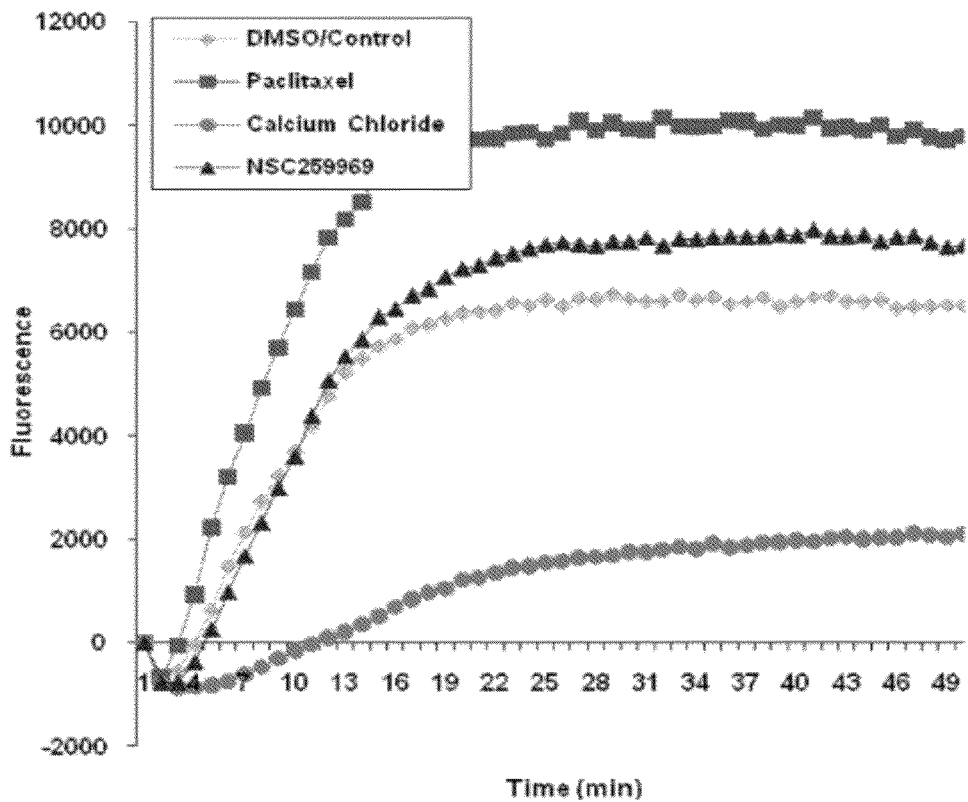
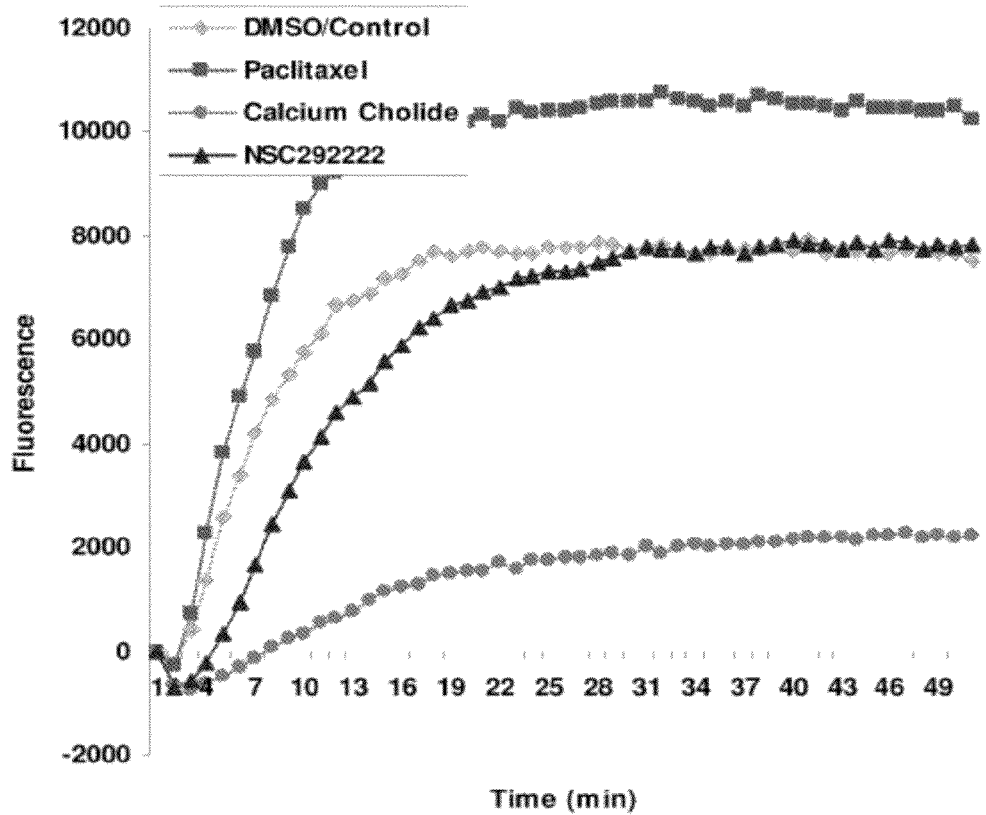

FIG. 16 (Page 3 of 4)
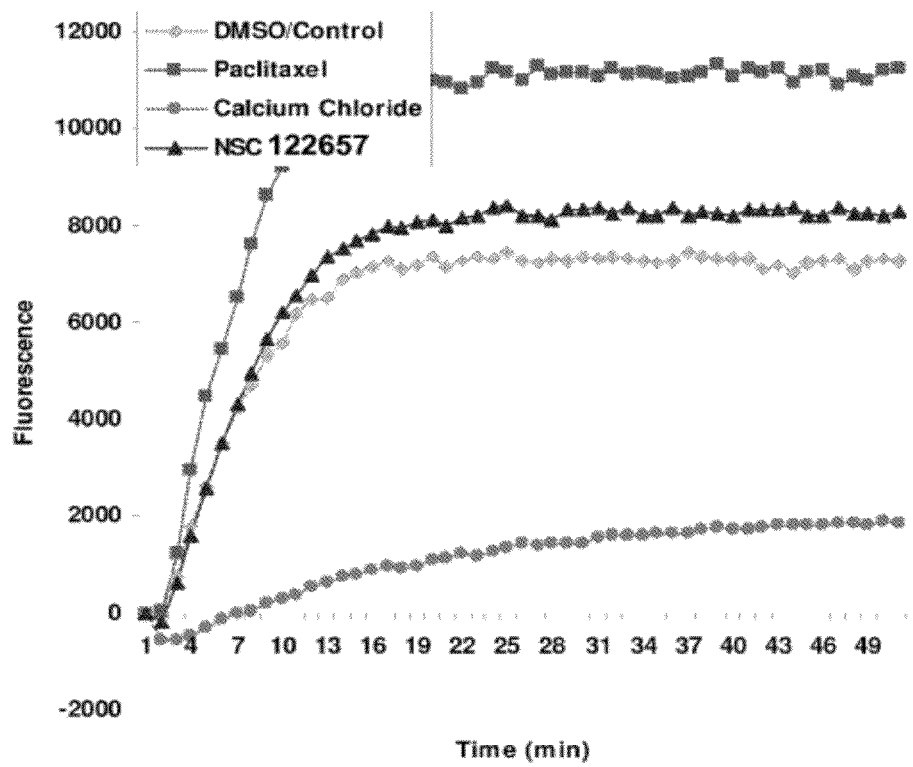
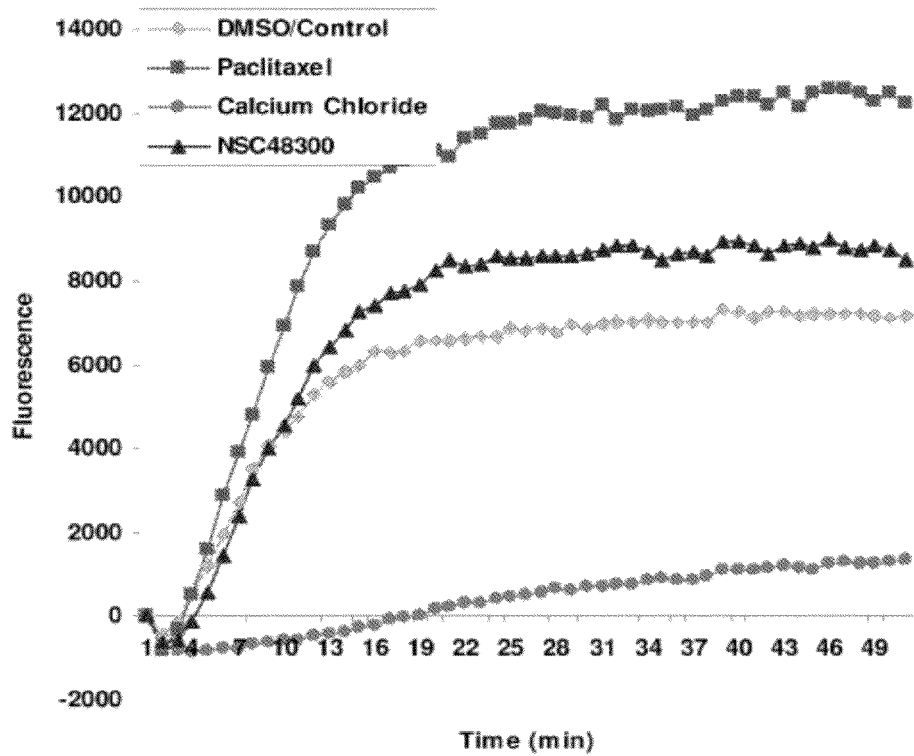

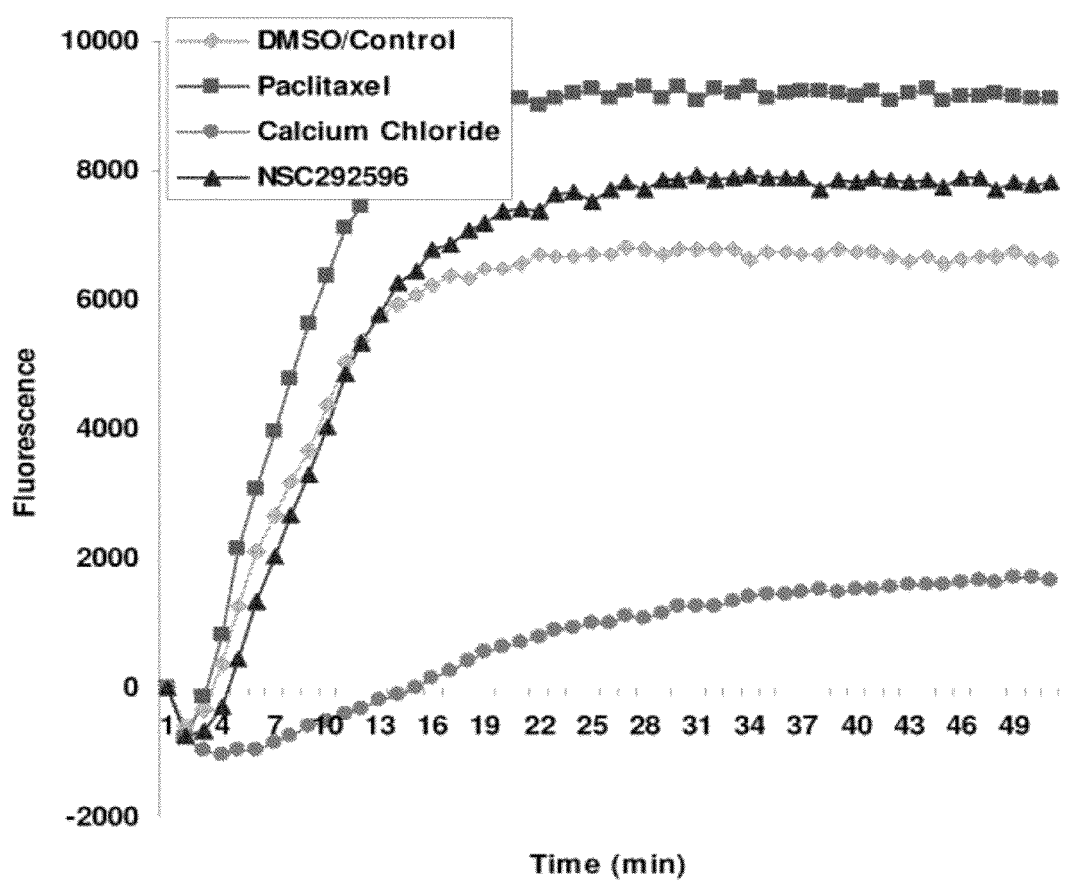
FIG. 16 (Page 4 of 4)

FIG. 17 (Page 1 of 6)
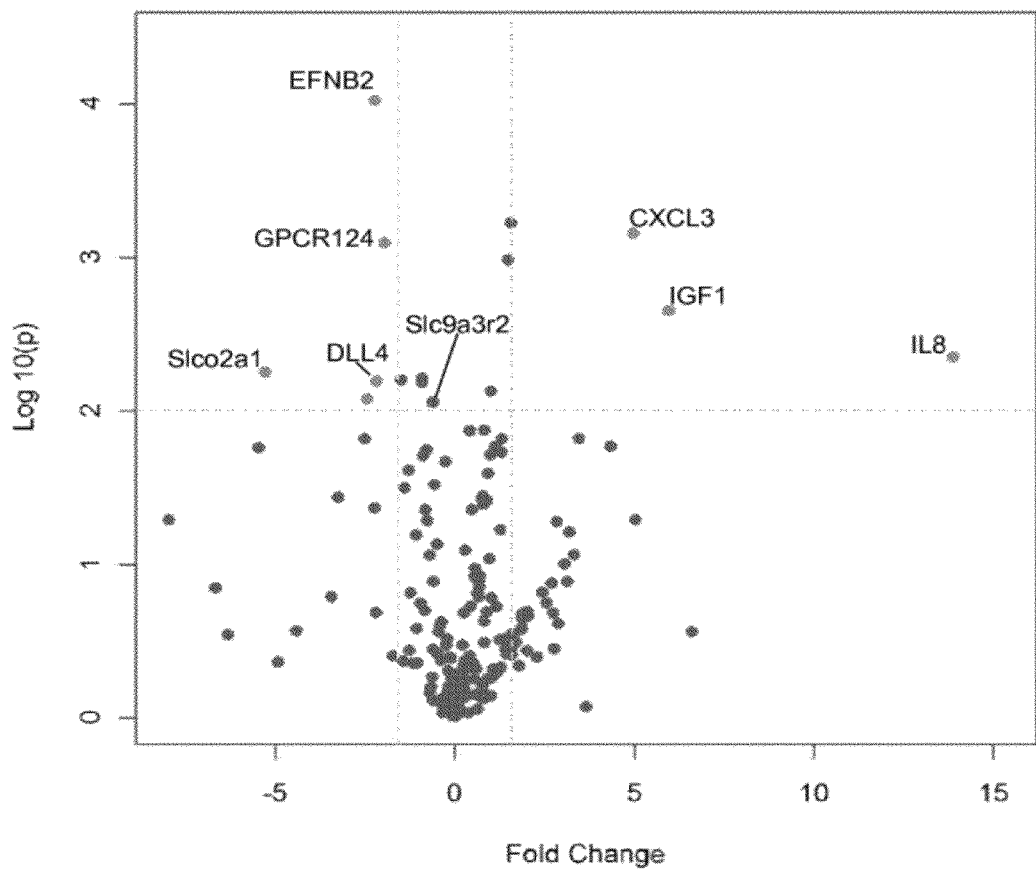

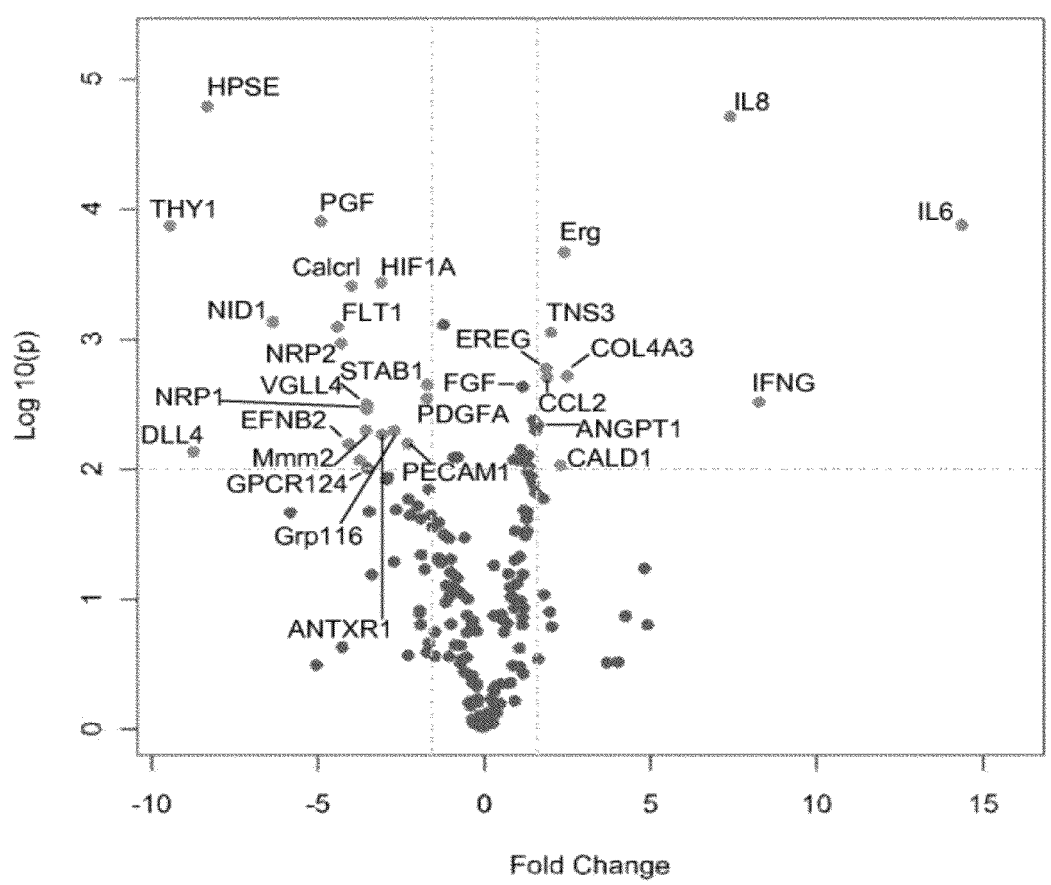
FIG. 17 (Page 2 of 6)

FIG. 17 (Page 3 of 6)
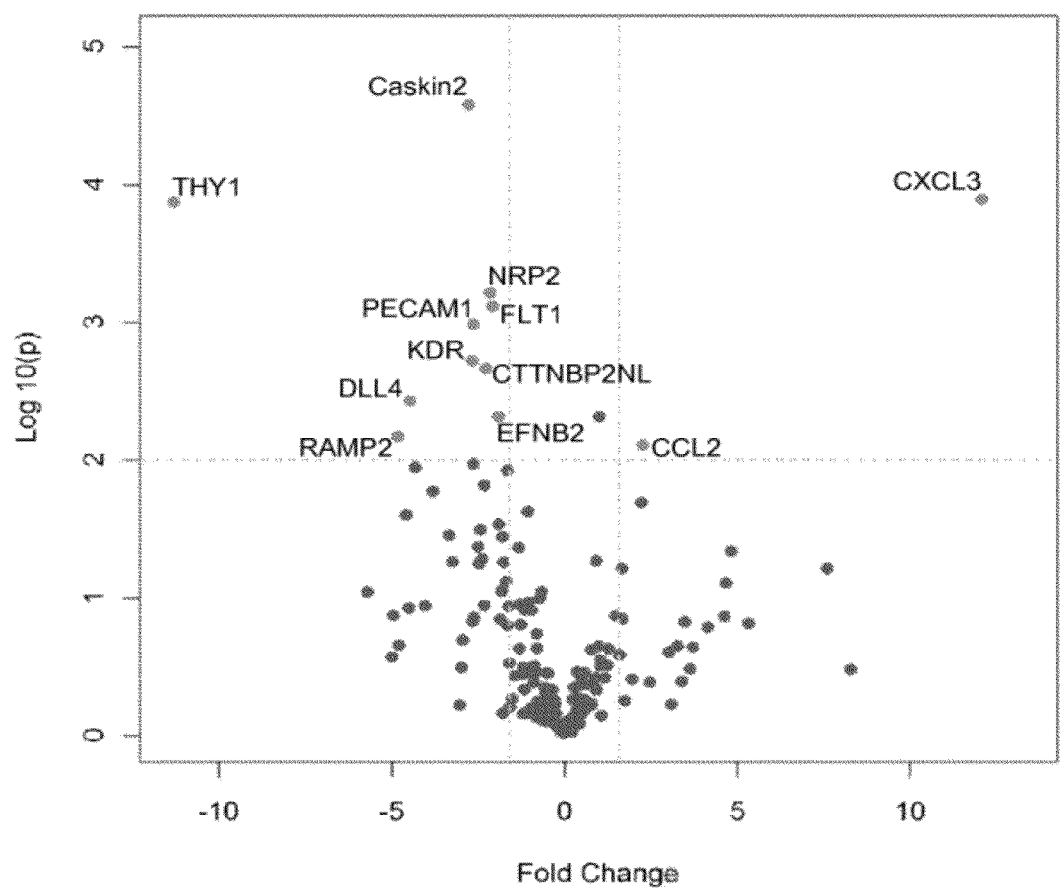

FIG. 17 (Page 4 of 6)
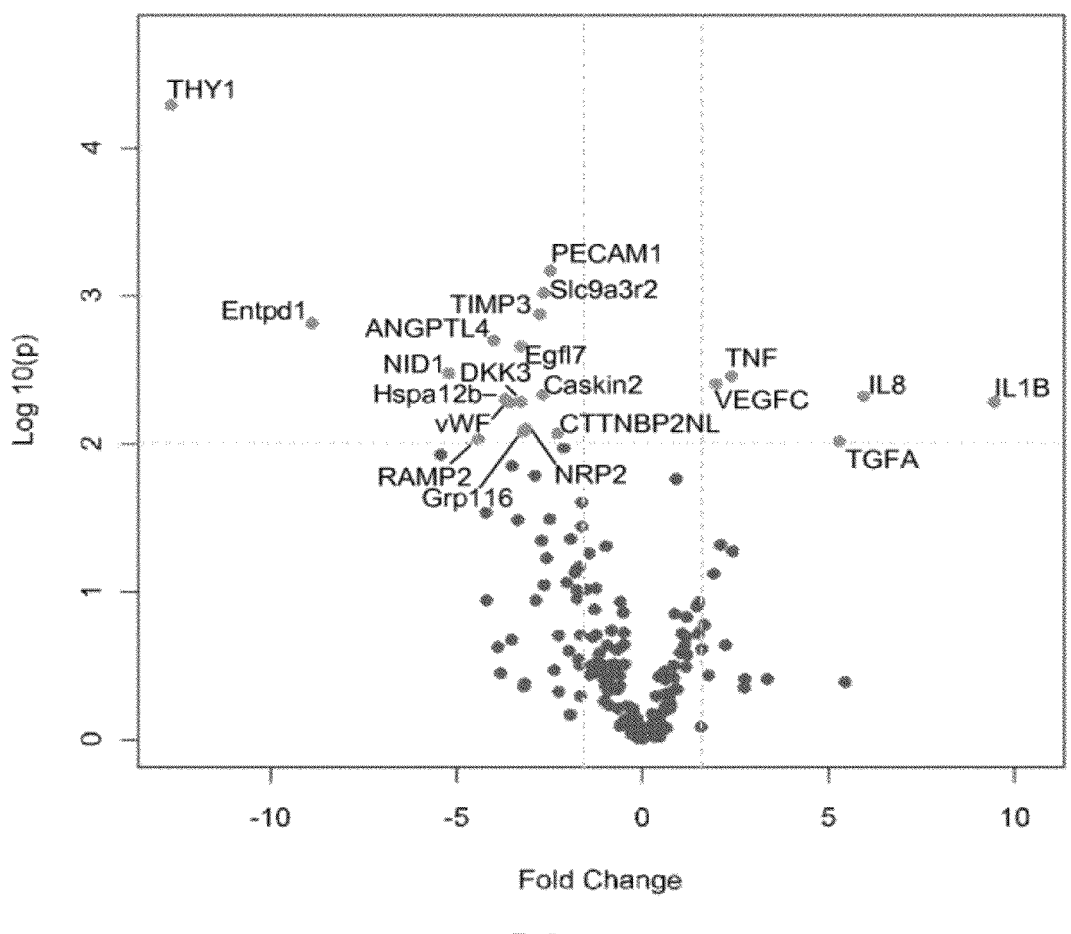
Egfl7

FIG. 17 (Page 5 of 6)
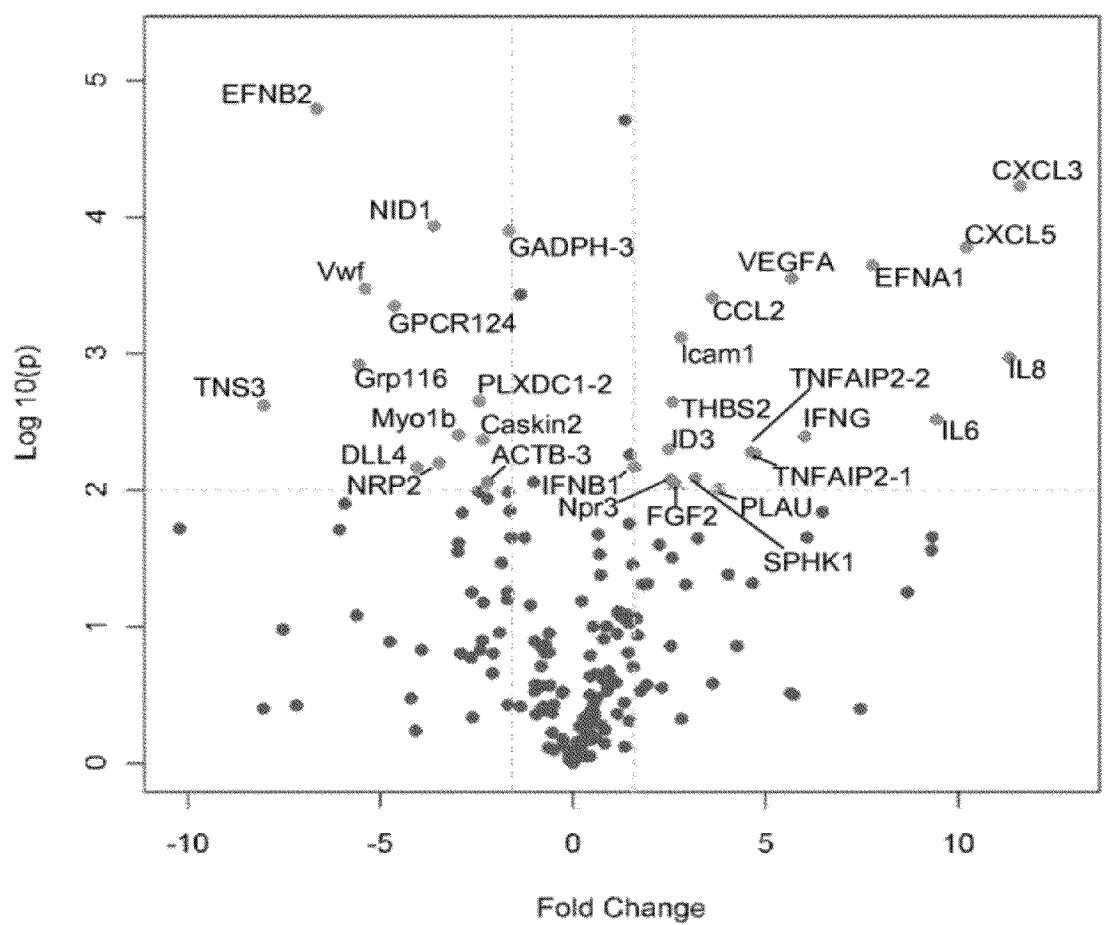

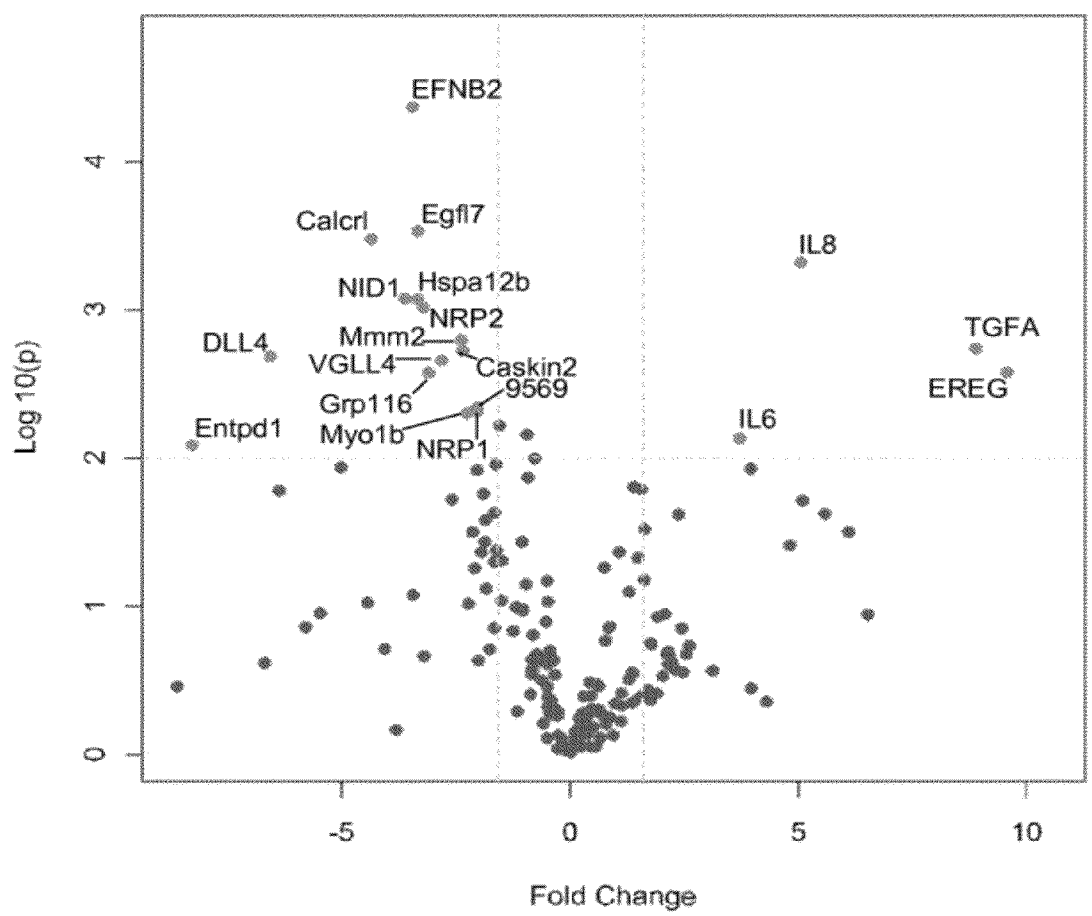
FIG. 17 (Page 6 of 6)

ANTIANGIOGENIC SMALL MOLECULES AND METHODS OF USE

CROSS REFERENCE TO RELATED APPLICATION

This is the U.S. National Stage of International Application No. PCT/US2010/043998, filed Jul. 30, 2010, which was published in English under PCT Article 21(2), which in turn claims the benefit of U.S. Provisional Application No. 61/230,667, filed Jul. 31, 2009, which is incorporated herein by reference in its entirety.

FIELD OF THE DISCLOSURE

The present disclosure relates to antiangiogenic compounds, derivatives thereof, and methods of use of such compounds and derivatives.

BACKGROUND

Angiogenesis is the process of formation of new blood vessels from existing ones. Angiogenesis is a normal and vital process in growth and development, as well as in pathological conditions. Angiogenesis has been intensively studied over the past several decades because of its fundamental importance in tissue development, vascular diseases, and cancer. Under normal physiological conditions, humans or animals undergo angiogenesis only in very specific restricted situations. For example, angiogenesis is normally observed in fetal and embryonal development and formation of the corpus luteum. Post-natal angiogenesis is an important physiological function in the ovary, endometrium, placenta, and in wound healing. Deregulation of angiogenesis plays a major role in many human diseases including diabetic retinopathy, age-related macular degeneration, endometriosis, atherogenesis, arthritis, psoriasis, corneal neovascularization, rheumatoid arthritis, tumorigenesis, and metastasis, among others.

Tumor angiogenesis involves the proliferation of a network of blood vessels that penetrates into cancerous growths, supplying nutrients and oxygen and removing waste products. Angiogenesis is also an element of metastasis of a tumor. Single cancer cells can break away from an established solid tumor, enter the blood vessel, and be carried to a distant site, where they can implant and begin the growth of a secondary tumor. It has even been suggested that the blood vessels in a solid tumor may in fact be mosaic vessels, comprised of both endothelial cells and tumor cells. Such mosaicity allows for substantial shedding of tumor cells into the vasculature.

It has been shown that there is a direct correlation between tumor microvessel density and the incidence of metastasis. Tumor cells themselves can produce factors that stimulate the proliferation of endothelial cells and new capillary growth. Angiogenesis is important in two stages of tumor metastasis: in vascularization of the tumor, which allows tumor cells to enter the blood stream and to circulate throughout the body; and after the tumor cells have left the primary site and settled into the secondary (metastasis) site, angiogenesis must occur before the new tumor can grow and expand. Therefore, prevention of angiogenesis could lead to the prevention of metastasis of tumors and possibly contain the neoplastic growth at the primary site.

Blockage of angiogenesis is recognized as one of the most promising strategies against cancer (including metastases), retinopathy and endometriosis, among other diseases. A significant increase in the research effort in the angiogenesis field over the past decade has resulted in a substantial increased understanding of the angiogenic process and subsequently the development of new therapeutics to modulate angiogenesis. Because of their extended biological half-life, high diffusibility coefficient and cost effective synthesis non-peptidic antiangiogenic small molecules (SMs) are the main focus of pharmaceutical companies and academic institutions.

Angiogenesis-based anti-tumor therapies typically use natural and synthetic angiogenesis inhibitors such as angiostatin, endostatin and tumstatin. Recently the Food and Drug Administration (FDA) approved an antibody therapy targeting angiogenesis in colorectal cancer. This therapy is based on a monoclonal antibody directed against an isoform of VEGF and is marketed under the trade name Avastin®. The pharmaceutical industry has focused in the development tyrosine kinase inhibitors and tubulin binders as antiangiogenic small molecules. Thus, a need exists for small molecules which exploit other angiogenesis pathways.

SUMMARY OF THE DISCLOSURE

The present disclosure relates to the identification of a new set of antiangiogenic small molecule inhibitors. Cell-based high throughput screenings (HTS) together with chemo-informatic tools were applied to the discovery of antiangiogenic small molecules. Rather than targeting the HTS to a single subcellular molecule, the screen described herein targeted the entire cellular process of angiogenesis. In particular, two cell based assays were employed, which represent the two most important steps in angiogenesis: endothelial cell growth and tube formation.

As a result, a new set of antiangiogenic small molecules (SMs) have been discovered. Structure-activity-relationship (SAR) studies have shown that the majority of the newly identified bioactive SMs are not related to previously recognized antiangiogenic SMs, based on comparisons to various databases (e.g., FDA marketed compounds; SMs currently in clinical trials compounds; and SMs annotated as antiangiogenic in chemical databases compounds, PubChem, LeadScope, DrugBank, DTP/NCI, etc.).

Based on the identification of this new set of antiangiogenic SMs, disclosed herein are methods for inhibiting angiogenesis (particularly undesired angiogenesis) in a subject that include administering to a subject a therapeutically effective amount of at least one antiangiogenic compound (e.g., antiangiogenic small molecule) from among the compounds referred to herein as Compounds 1-77, or pharmaceutically acceptable salts thereof, examples of which are described in detail below.

Also disclosed herein are methods of inhibiting angiogenesis that include administering to a subject a therapeutically effective amount of at least one of the compounds referred to herein as Compounds 1-77, or pharmaceutically acceptable salts thereof, examples of which are described in detail below.

Further disclosed herein are compounds having a structure represented by any one of the formulas shown in TABLE 1 (referred to herein as Compounds 1-77), and pharmaceutically acceptable salts thereof. Pharmaceutical compositions that include the above-described compounds are also disclosed herein.

Thus, disclosed herein are pharmaceutical compositions for treating an angiogenesis-dependent disease, comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically-acceptable salt thereof. In particular examples, the pharmaceutical composition further comprises [4-[(4-arsonophenyl)methyl]phenyl]arsonic acid (NSC 48300), or a pharmaceutically-acceptable salt thereof.

Also disclosed herein are pharmaceutical compositions for inhibiting aberrant angiogenesis or inhibiting growth of neoplastic tissue comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically-acceptable salt thereof. In particular examples, the pharmaceutical composition further comprises [4-[(4-arsonophenyl)methyl]phenyl]arsonic acid (NSC 48300), or a pharmaceutically-acceptable salt thereof.

Also disclosed herein are methods of treating an angiogenesis-dependent disease, comprising: administering to a subject having or predisposed to an angiogenesis-dependent disease a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular embodiments of the methods, the composition further comprises [4-[(4-arsonophenyl)methyl]phenyl]arsonic acid (NSC 48300), or a pharmaceutically-acceptable salt thereof.

Further disclosed herein are methods of inhibiting undesired angiogenesis in a subject, comprising: identifying a subject wherein angiogenesis is not desired, and administering to the subject a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular examples of the disclosed methods, the composition further comprises [4-[(4-arsonophenyl)methyl]phenyl]arsonic acid (NSC 48300), or a pharmaceutically-acceptable salt thereof.

Also disclosed are methods of inhibiting a neoplasm in a subject, comprising: administering to the subject a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular examples, the composition further comprises [4-[(4-arsonophenyl)methyl]phenyl]arsonic acid (NSC 48300), or a pharmaceutically-acceptable salt thereof.

Further disclosed are methods of inhibiting angiogenesis in a tissue or a target area in a subject wherein the formation of new blood vessels is not desired, comprising identifying a tissue or target area in a subject wherein the formation of new blood vessels is not desired; and introducing directly or indirectly into the tissue or target area an effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof, thereby inhibiting angiogenesis in the tissue or target area. In particular examples, the composition further comprises [4-[(4-arsonophenyl)methyl]phenyl]arsonic acid (NSC 48300), or a pharmaceutically-acceptable salt thereof.

The foregoing and other objects, features, and advantages will become more apparent from the following detailed description, which proceeds with reference to the figures.

Figure 4:
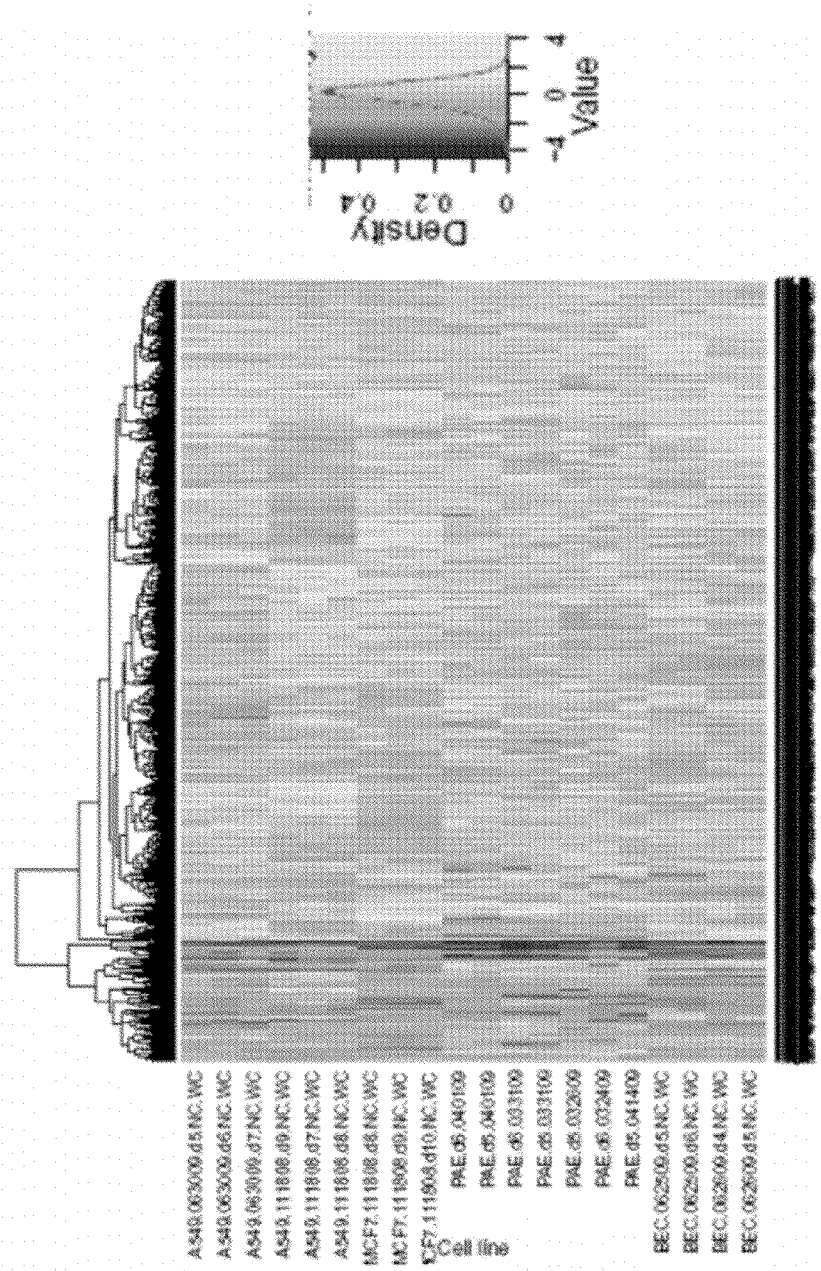
FIG. 4: Following the same protocol, HTS growth experiments were performed for PAE, BEC, A549 and MCF7 cells. These experiments were designed to explore the specificity of SMs with inhibitory activity in endothelial cells as compared to tumor cells from different anatomical origins.

The image in FIG. 4 shows a heatmap which summarizes the results obtained in the HTS experiments. The heatmap was constructed using the function heatmap.2 of the package gplots of the R statistical software. Clustering was performed using Euclidean distance matrix. The X axis shows the 1974 SMs tested and the Y axis represents some of the growth HTS experiments performed. For all experiments, measurements obtained in different days have been included and as expected show a high degree of consistency. Dark cells in the heatmap represent SMs with strongest growth inhibitory activity, and lighter greys are SM with no activity on growth.

Figure 5:
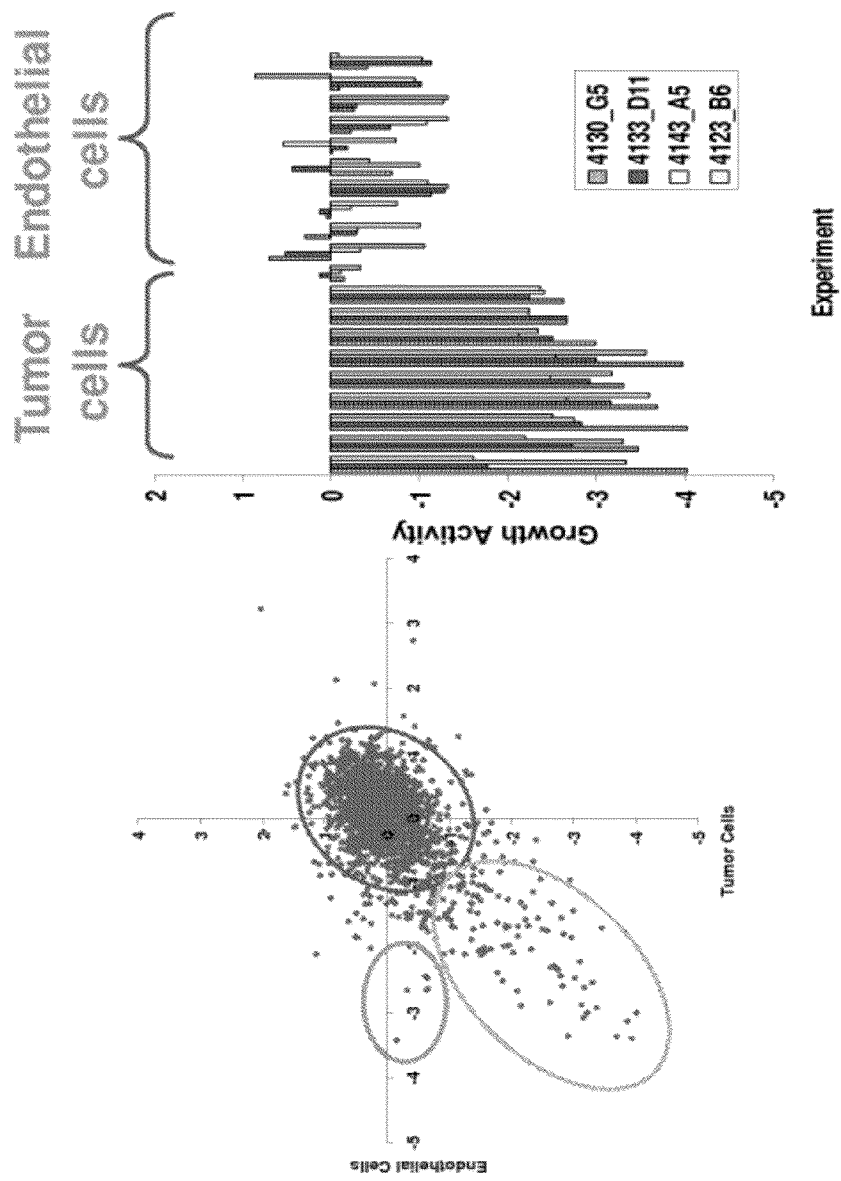

FIG. 5: In order to study SMs which preferentially inhibit the growth of endothelial cells or tumor cells, average growth activity values for endothelial cells and tumor cells were compared in a bivariate scatterplot. Most of the SMs do not have an effect on growth in any of the cell lines tested and cluster in the center of the scatterplot (indicated within the middle-sized oval). Also, most SMs with growth inhibitory activity show similar potency against tumor cells and endothelial cells and therefore cluster in the lower left quadrant (indicated within the largest oval). Interestingly, a few SMs showed growth inhibitory activity in tumor cells but not in endothelial cells (small oval; see also TABLE 10). Growth activity of these small molecules is shown in the adjacent plot (small molecules are identified by their position in the plate; TABLE 10 correlates plate position to NSC number).

Figure 6:
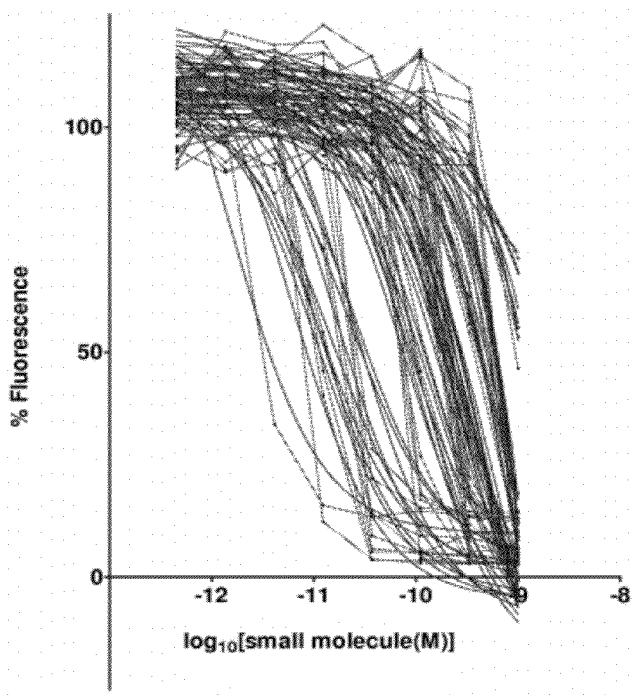

FIG. 6: Dose response curves were constructed for all the SMs of interest using PAE cells. Data were fitted to non-linear sigmoid curves using GraphPad Prism (GraphPad Software, Inc., La Jolla, Calif.). Since the initial screening was performed using a final SM concentration of 1 µM, IC50 for most compounds were confirmed to be in the range of $10^{-12}$ to $10^{-9}$ M. This confirms that all the SMs discovered in this project are highly potent inhibitors of endothelial cell growth.

Figure 7:
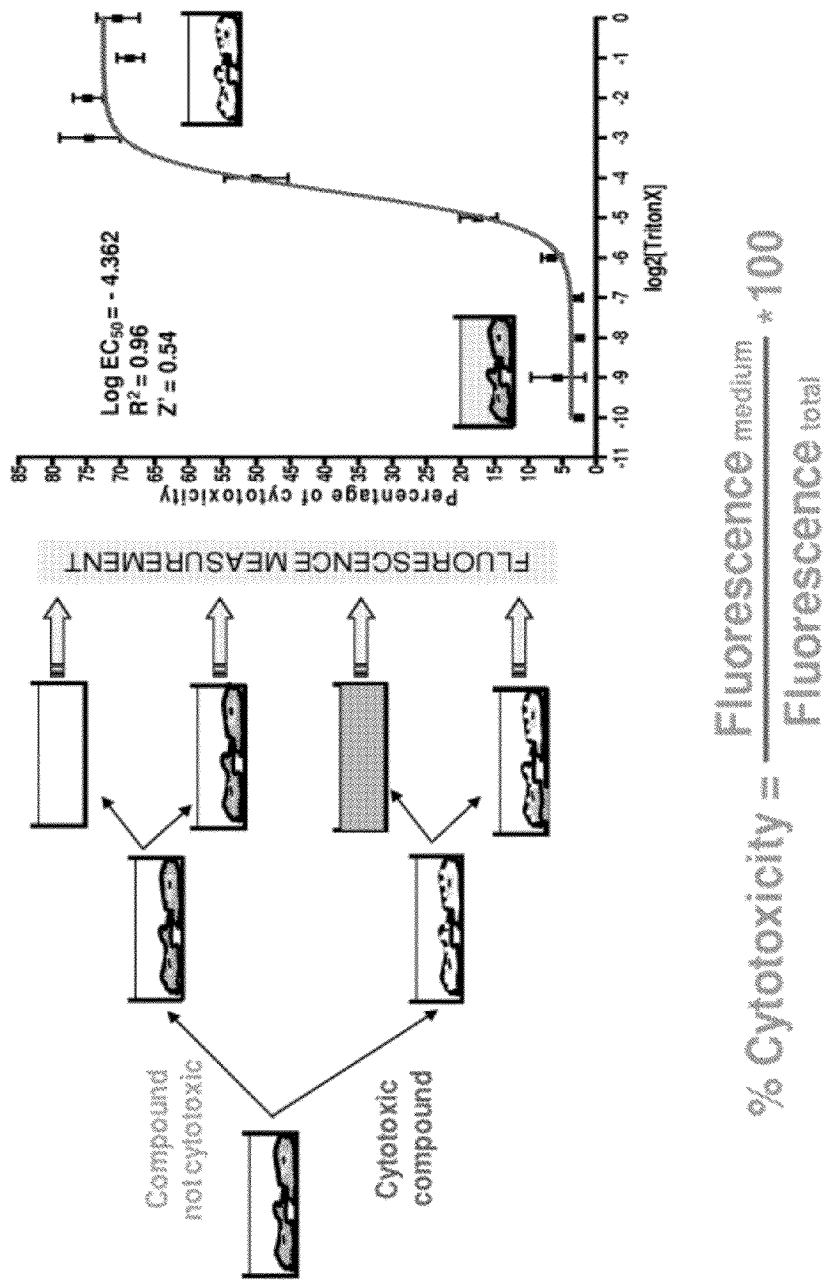

FIG. 7: In order to explore the cytotoxic potential of the SMs of interest, a novel high throughput cytotoxicity assay was developed, and is further described in U.S. application Ser. No. 12/060,752 (published as US 2009/0088341 on Apr. 2, 2009; incorporated herein by reference in its entirety). In FIG. 7, two different hypothetical situations are graphically described: In the lower area of the diagram, fluorescent cells are exposed to a cytotoxic substance, which results in the release of florescence to the cell culture medium. Both the fluorescence in the medium and the remaining fluorescence in the cells can be quantitated and used to calculate the percentage of cytotoxicity using the formula in the lower area of the figure. The plot shows the expected dose response curve when Triton X is used as a cytotoxic agent on PAE cells.

Figure 8:
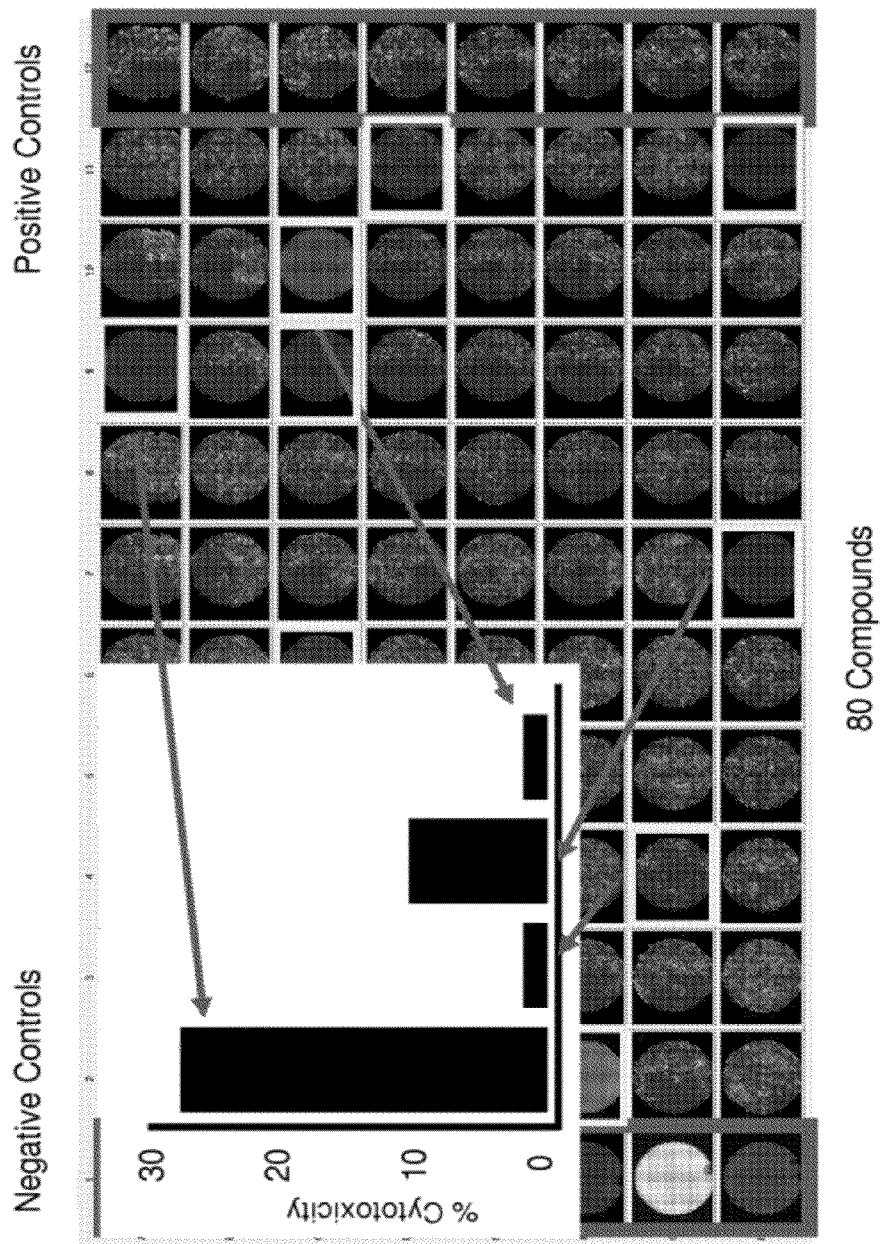

FIG. 8 shows an example of four compounds with growth inhibitory activity, two of which present a strong and moderate cytotoxic activity respectively. Using the cytotoxicity assay illustrated in FIG. 7 and described herein, four compounds were identified as cytotoxic (NSC 88903, NSC 310551, NSC 18877, and NSC 321206; see TABLE 10).

Figure 9:
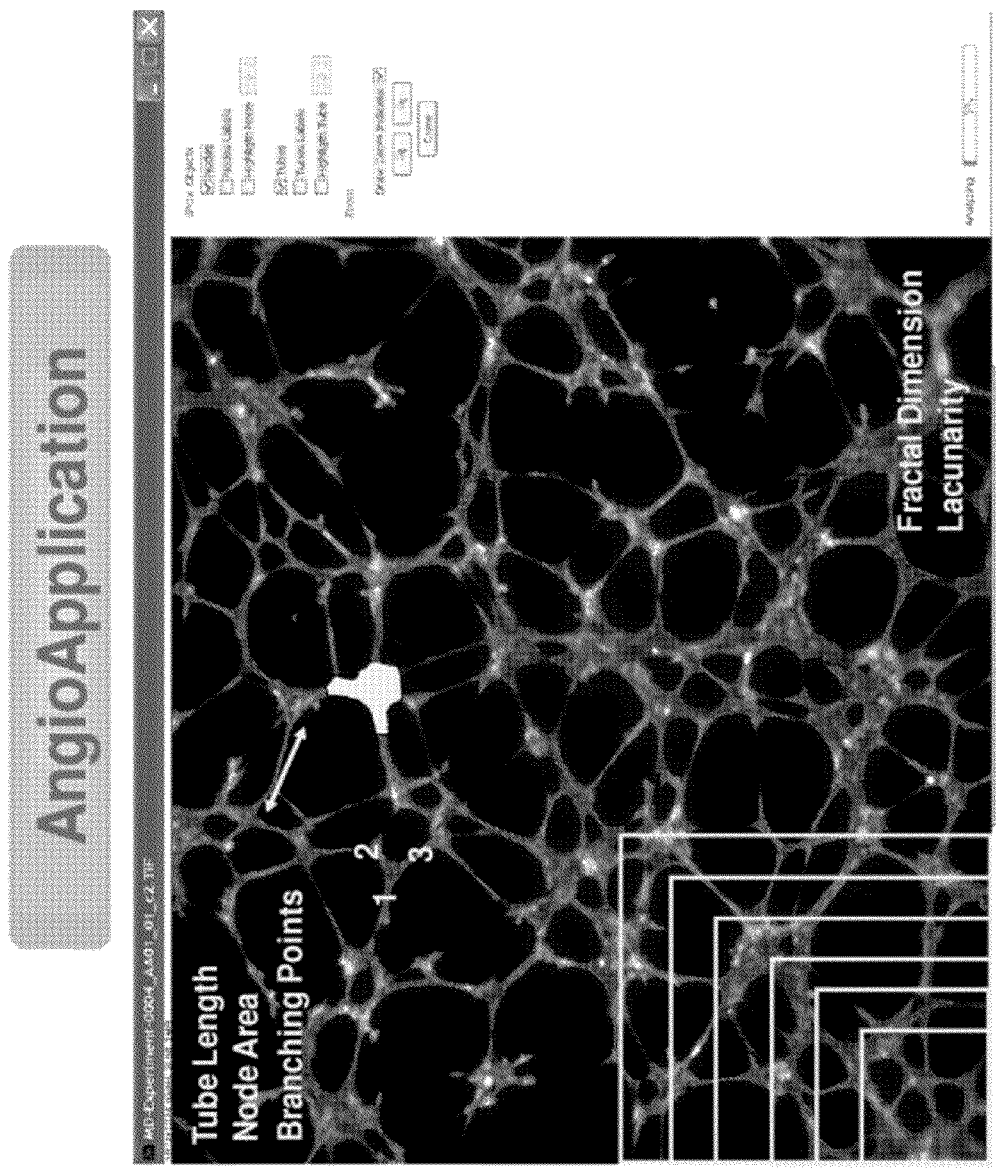

FIG. 9 shows a screen shot from the an image analysis program named AngioApplication™, which was developed for the HTS format and permitted a morphological quantitative analysis of tube formation (described in detail in U.S. application Ser. No. 12/060,752, which published as US 2009/0088341 on Apr. 2, 2009; incorporated herein by reference in its entirety). This software is able to rapidly assess a variety of metrics in images of tube formation including (but not limited to) tube length, node area, branching points, fractal dimension and lacunarity.

Figure 10:
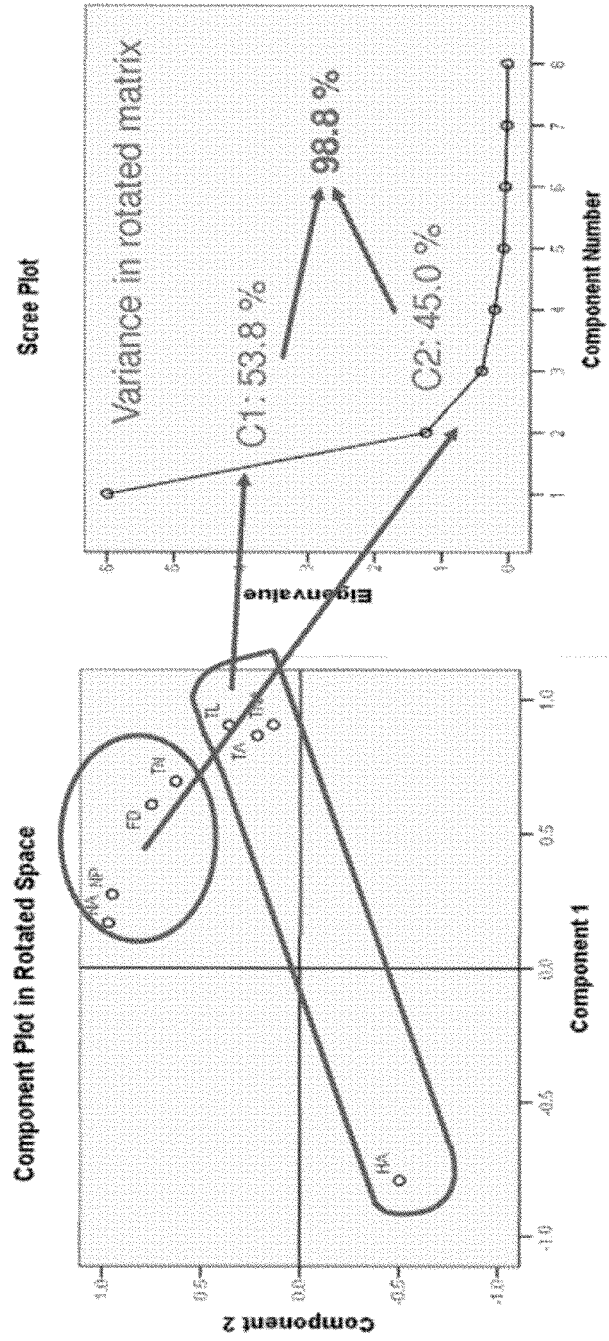

FIG. 10 shows how principal component analysis was used to investigate which metrics explained better the variability of the data sets. The results showed that emptiness and branching index were the most appropriate metrics.

Figure 11:
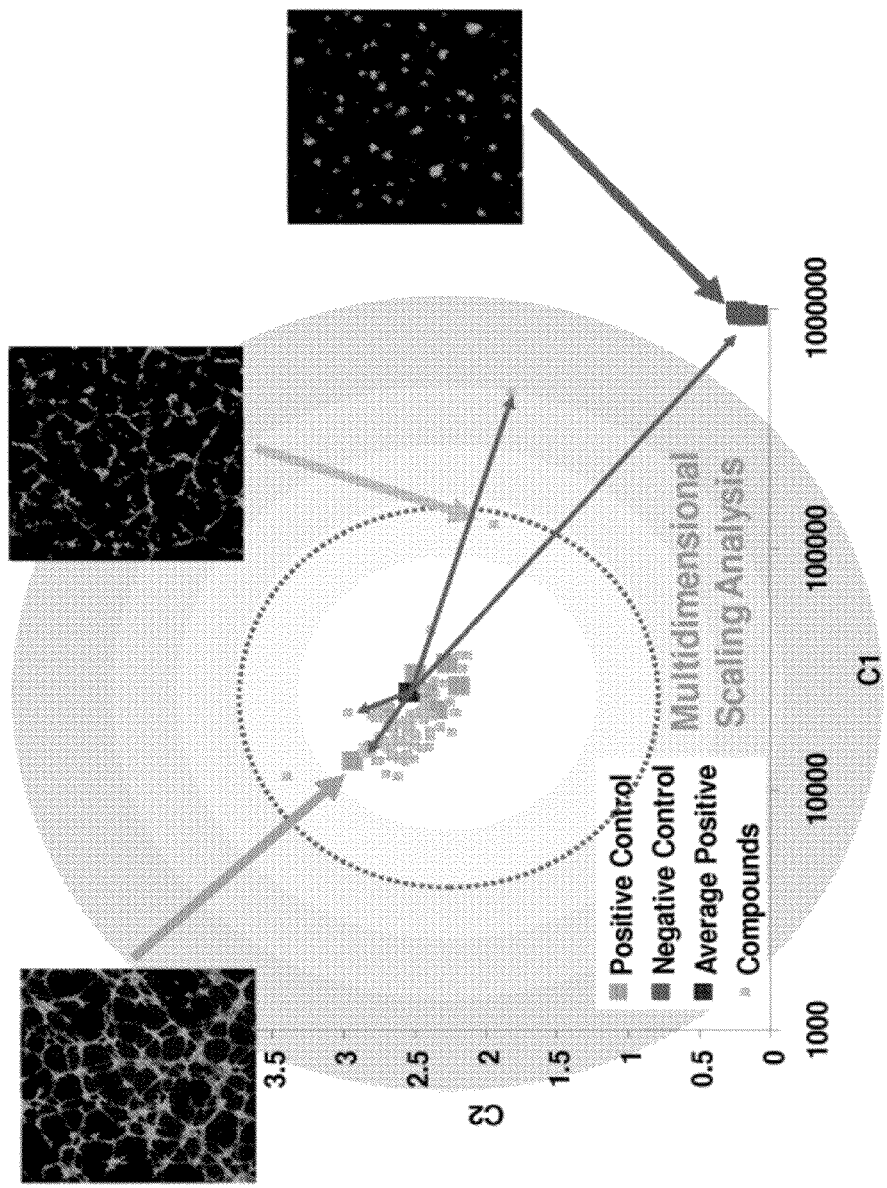

FIG. 11: Emptiness (C1) and branching index (C2) were plotted in a bivariate scatter plot for every SM tested. The Euclidean distance between the average of the positive controls and every SM was used as metric to define anti-tube formation activity (calculations were done separately for every plate). In essence, compounds which are further away from the positive controls are more likely to be antiangiogenic. This figure illustrates the results from all the SMs in one plate. As expected, most of the compounds (small squares clustered in center of graph) are located closely to the positive controls (large squares clustered near center of graph). In contrast, the negative controls (large squares clustered in lower right corner of graph) are positioned farther away from the positive controls. Representative images of the positive and negative control cells are shown. Tube formation inhibitory compounds are detected as being located at an intermediate distance between the positive controls and the negative controls. A representative image of an active SM is shown. 35 out the 1974 compounds in the library (1.75%) were found to statistically significantly inhibit tube formation (TABLE 10).

Figure 12:
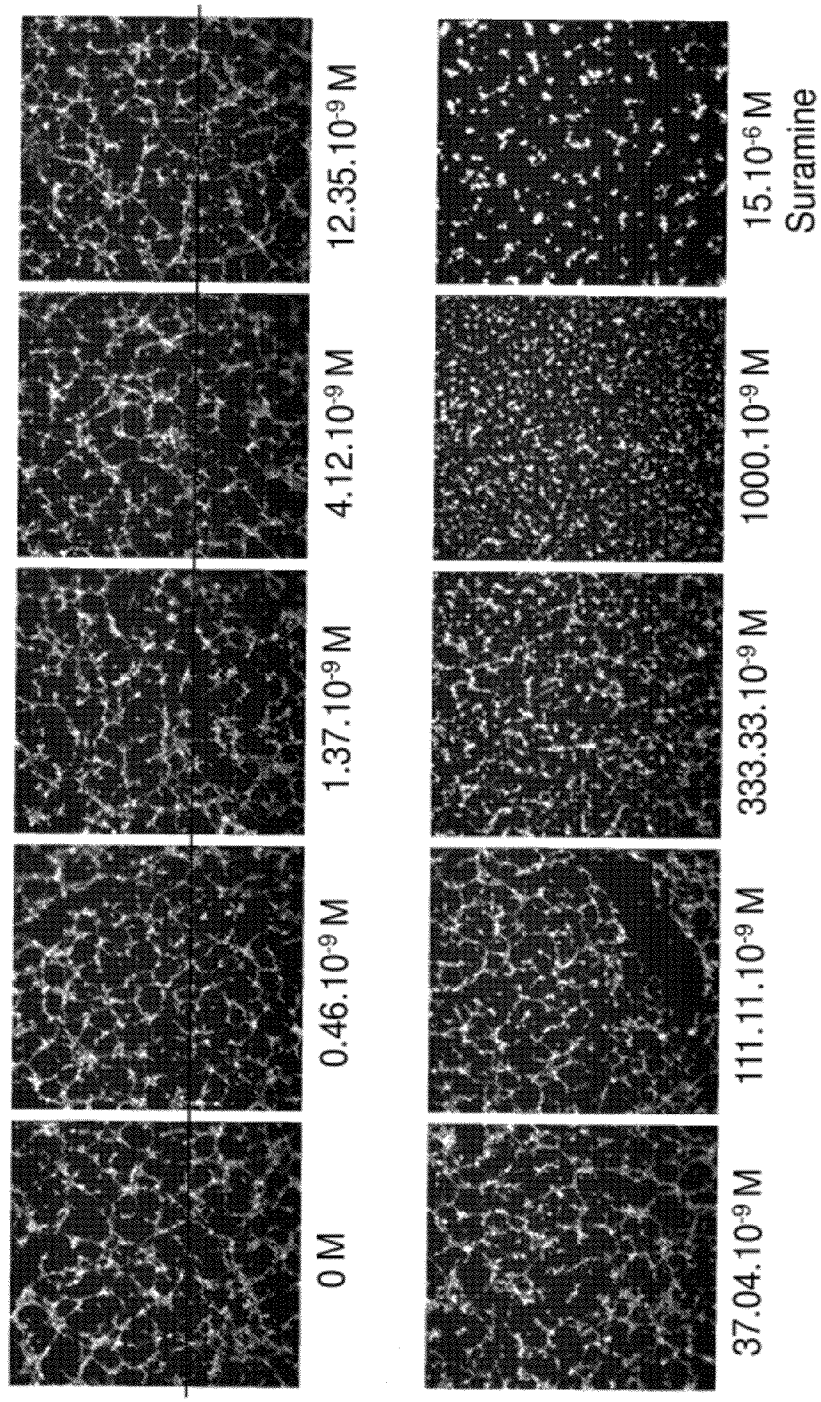

FIG. 12: IC50 were calculated for all tube formation inhibitors. As expected, most IC50 were in the range of $10^{-9}$ to $10^{-12}$ M, making these compounds highly effective tube formation inhibitors. This figure illustrates an example of the dose response generated with compound NSC119889.

Figure 13:
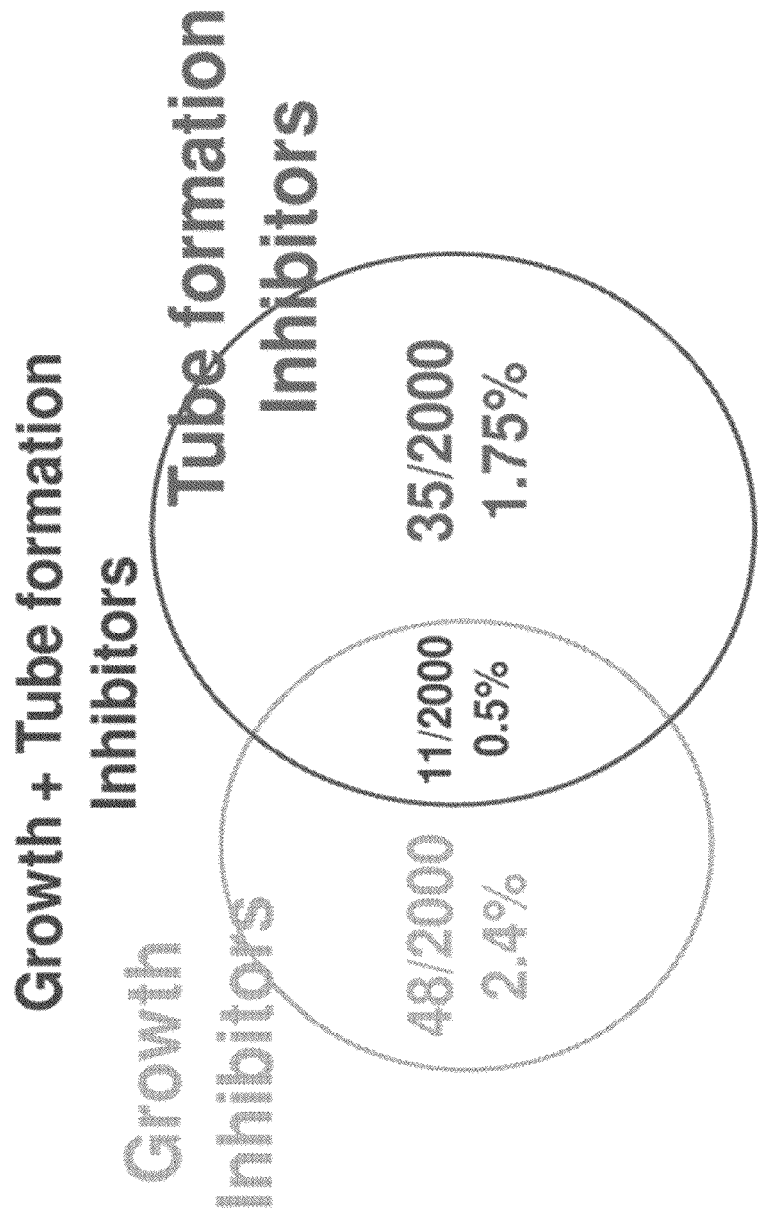

FIG. 13 summarizes the results obtained in the growth and tube formation HTS for endothelial cells; information related to specific compounds is summarized in TABLE 10. 2.4% (48) of the compounds were growth inhibitors, and 1.75% (35) were tube formation inhibitors. 0.5% (11) of the compounds showed both growth and tube formation inhibitory activity.

Figure 14:
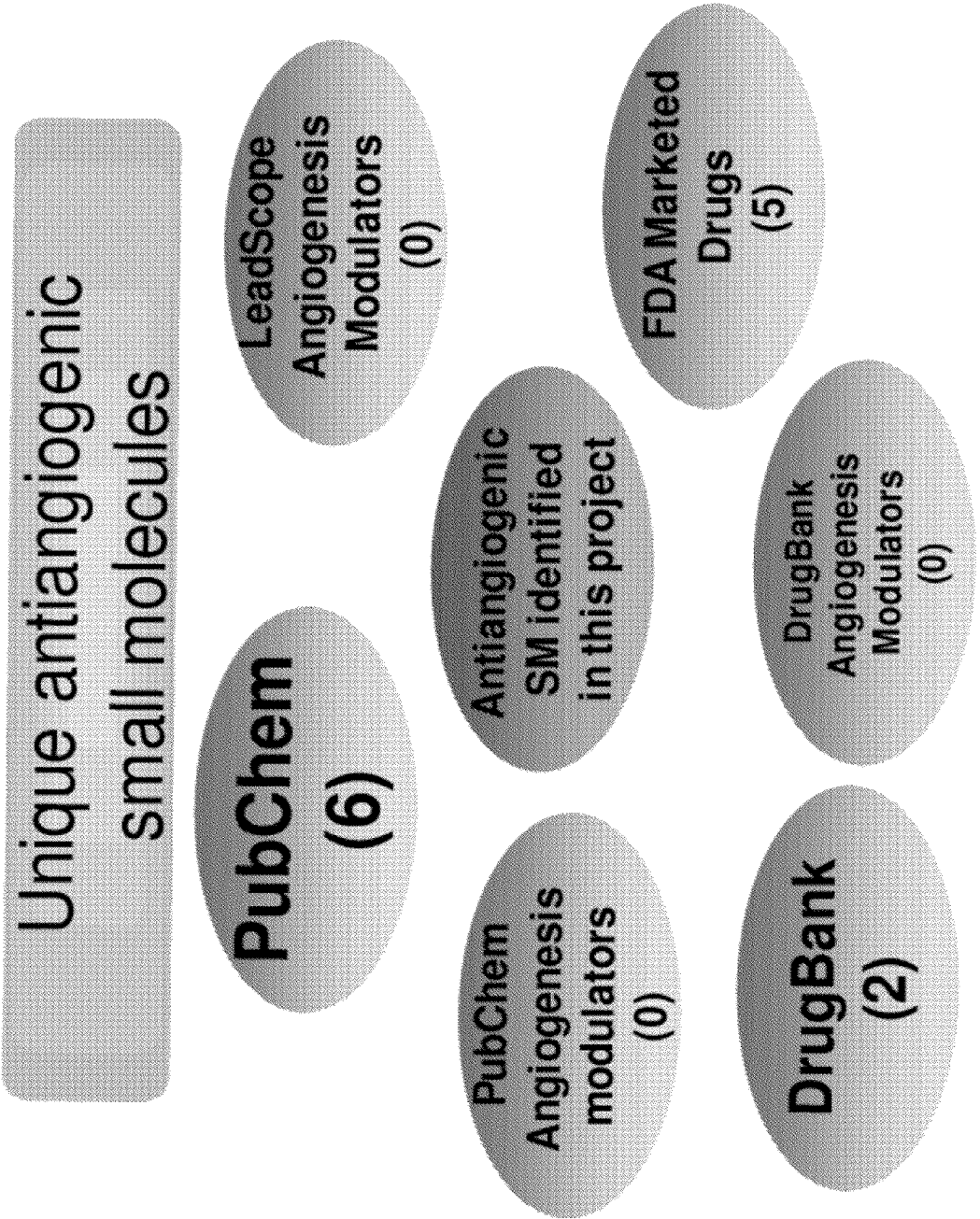

FIG. 14: The antiangiogenic SMs identified in this project were structurally compared with annotated compounds in available annotated SM databases, such as PubChem, Drug-Bank, LeadScope and FDA Marketed Drugs among others. Structural classifications were performed with LeadScope software. Only a few of the SMs identified were structurally related to annotated compounds in other databases (numbers in parenthesis in the above figure). This can be explained by the novel drug discovery methodology utilized in this project, which, as expected, results in compounds with novel SARs. None of the antiangiogenic SMs discovered in this project are structurally related to any known antiangiogenic SMs. This supports the novelty of the herein described antiangiogenic SMs and emphasizes that new SARs will result in exploitation of new cellular antiangiogenic pathways.

FIG. 15 is a series of graphs showing the inhibitory effects of selected SMs on growth of tumor xenografts. Top panels show the effect of SMs on growth of A549 tumors. Bottom panels show the effect of SMs on growth of SK-ML-1 tumors.

FIG. 16 is a series of graphs showing the effects of selected SMs on the inhibition of tubulin polymerization.

FIG. 17 is a series of volcano plots showing quantitative real time RT-PCR analysis of the effects of selected SMs on expression of genes implicated in angiogenesis

SEQUENCE LISTING

The nucleic and/or amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The SEQ ID designations in the accompanying sequence listing are set forth in Table 13. Sequences and information associated with the accession numbers listed on Table 14 (and available online at ncbi.nlm.nih.gov/guide/) are incorporated by reference herein in their entirety.

The Sequence Listing is submitted as an ASCII text file, Annex C/St.25 text file, created on Jul. 27, 2010, 68.1 KB, which is incorporated by reference herein.

DETAILED DESCRIPTION OF SEVERAL EMBODIMENTS

I. Abbreviations bFGF: basic fibroblast growth factor
EC50: The term half maximal effective concentration
FDA: Food and Drug Administration
GFP: green fluorescent protein
HTS: high throughput screen PAE: porcine aortic endothelial
RTK: receptor tyrosine kinase
SAR: structure-activity relationship
SMs: small molecules
RFP: red fluorescent protein
VEGF: vascular endothelial growth factor
YFP: yellow fluorescent protein II. Terms Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. The term "comprises" means "includes." The abbreviation, "e.g." is derived from the Latin exempli gratia, and is used herein to indicate a non-limiting example. Thus, the abbreviation "e.g." is synonymous with the term "for example." All chemical compounds include both the (+) and (−) stereoisomers (as well as either the (+) or (−) stereoisomer), and any tautomers thereof. It is further to be understood that all molecular weight or molecular mass values given for compounds are approximate, and are provided for description. Although methods and materials similar or equivalent to those described herein can be used in the practice or testing of this disclosure, suitable methods and materials are described herein. In addition, the materials, methods, and examples are illustrative only and not intended to be limiting.

To facilitate review of the various embodiments of the disclosure, the following explanations of specific terms are provided:

Acid: A compound capable of transferring a hydrogen atom in solution. Acid is inclusive of, but not limited to, a carboxylic acid.

Administer/Administration: To give or apply, for instance to a subject. To "introduce" is understood to be equivalent to "administer." This term includes topical, parenteral, oral, intravenous, intra-muscular, sub-cutaneous, inhalational, nasal, or intra-articular routes of administration, among others. By way of example, a therapeutic compound, such as an antiangiogenic agent, can be administered. Administration can be local or systemic, direct or indirect.

Non-limiting examples of local administration include, but are not limited to, topical administration, subcutaneous administration, intramuscular administration, intrathecal administration, intrapericardial administration, intra-ocular administration, topical ophthalmic administration, or administration to the nasal mucosa or lungs by inhalational administration. In addition, local administration includes routes of administration typically used for systemic administration, for example by directing intravascular administration to the arterial supply for a particular organ or tumor. Thus, in particular embodiments, local administration includes intra-arterial administration and intravenous administration when such administration is targeted to the vasculature supplying a particular organ or tumor.

Systemic administration includes any route of administration designed to distribute the administered compound widely throughout the body via the circulatory system. Thus, systemic administration includes, but is not limited to, intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Direct administration or introduction involves the direct contact of a compound to a target are, such as by injection. Indirect administration or introduction involves any other method other than direct contact of the compound, for example by oral ingestion.

Alkyl: A branched or straight chain alkyl group containing only carbon and hydrogen. In certain embodiments, alkyl groups may contain one to twelve carbon atoms, particularly one to six carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkoxy, cycloalkyl, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

Amino acid moiety: A moiety that contain one or more primary, secondary or tertiary amino groups and one or more acidic carboxyl groups (—COOH) or a moiety that is a derivative or residue of an amino acid in the sense that the moiety contains one or more amino groups (e.g., —NH$_2$) and one or more ester groups (i.e., —OC(O)—).

Animal: A living multi-cellular vertebrate organism, a category that includes, for example, mammals and birds. The term mammal includes both human and non-human mammals. Similarly, the term "subject" includes both human and veterinary subjects, for example, humans, non-human primates, dogs, cats, horses, pigs, rats, mice, and cows.

Angiogenesis: A biological process leading to the generation of new blood vessels through sprouting and/or growth from pre-existing blood vessels. The process can involve the migration and proliferation of endothelial cells from preexisting vessels. Angiogenesis occurs during pre-natal development, post-natal development, and in the adult. In the adult, angiogenesis occurs during the normal cycle of the female reproductive system, wound healing, and during pathological processes such as cancer (for a review see Battegay, *J. Molec. Med.* 73(7): 333-346, 1995).

Angiogenic activity: The ability of an agent to promote or inhibit angiogenesis. Angiogenic activity can be measured in an angiogenesis assay, for example using the fluorescent cell-lines and assays disclosed herein and/or in U.S. application Ser. No. 12/060,752 (published as US 2009/0088341 on Apr. 2, 2009; and incorporated herein by reference in its entirety).

Angiogesis-dependent disease: A disease that is at least partially dependent on the stimulation of aberrant (undesired) angiogenesis for its progression. Aberrant angiogenesis can result from misexpression of angiogenic factors in otherwise normal cells. Aberrant angiogenesis can also be stimulated by tumors producing one or more angiogenic factors.

Angiogenic factor: A molecule that affects angiogenesis, for example by stimulating or inhibiting angiogenesis.

Numerous experiments have suggested that tissues secrete factors that promote angiogenesis under conditions of poor blood supply during normal and pathological angiogenesis processes. The formation of blood vessels is initiated and maintained by a variety of factors secreted either by a cell (such as a tumor cell) or by accessory cells. Many different growth factors and cytokines have been shown to exert chemotactic, mitogenic, modulatory or inhibitory activities on endothelial cells, smooth muscle cells and fibroblasts and can, therefore, be expected to participate in an angiogenic process. For example, factors modulating growth, chemotactic behavior and/or functional activities of vascular endothelial cells include aFGF, bFGF, angiogenin, angiotropin, epithelial growth factor, IL-8, and vascular endothelial growth factor (VEGF) among others.

Because many angiogenic factors are mitogenic and chemotactic for endothelial cells, their biological activities (such as angiogenic activities) can be determined in vitro by measuring the induced migration of endothelial cells or the effect of these factors on endothelial cell proliferation using the cell-lines assays and methods disclosed herein. For example, migration assays and other assays, such as tubule formation assays and growth assays can also be used to determine angiogenic activity, for example the angiogenic activity in the presence of a test agent, such as a potential angiogenesis inhibitor.

Aryl: A monovalent unsaturated aromatic carbocyclic group having a single ring (e.g., phenyl) or multiple condensed rings (e.g., naphthyl or anthryl), which can optionally be unsubstituted or substituted with, e.g., halogen, alkyl, alkoxy, mercapto (—SH), alkylthio, trifluoromethyl, acyloxy, hydroxy, mercapto, carboxy, aryloxy, another aryl, arylalkyl, heteroaryl, amino, alkylamino, dialkylamino, morpholino, piperidino, pyrrolidin-1-yl, piperazin-1-yl, or other functionality.

Biological sample: A sample obtained from a plant or animal subject about which information is desired, for example, information about the samples ability to promote cellular growth, tubule formation, and/or cellular migration. As used herein, biological samples include all clinical samples, including, but not limited to, cells, tissues, and bodily fluids, such as: blood; derivatives and fractions of blood, such as serum, and lymphocytes (such as B cells, T cell, and subfractions thereof); extracted galls; biopsied or surgically removed tissue, including tissues that are, for example, unfixed, frozen, fixed in formalin and/or embedded in paraffin; tears; milk; skin scrapes; surface washings; urine; sputum; cerebrospinal fluid; prostate fluid; pus; bone marrow aspirates; middle ear fluids, bronchoalveolar levage, tracheal aspirates, sputum, nasopharyngeal aspirates, oropharyngeal aspirates, or saliva. In particular embodiments, the biological sample is obtained from an animal subject, such as in the form of middle ear fluids, bronchoalveolar levage, tracheal aspirates, sputum, nasopharyngeal aspirates, oropharyngeal aspirates, or saliva. In particular embodiments, the biological sample is obtained from a subject, such as blood or serum. A patient sample is a sample obtained from a subject, such as a mammalian subject, for example a human subject under medical care.

Cellular activity: An activity of a particular cell-line, such as the ability of the cell to divide, migrate in response to stimulus, or to form three dimensional structures, such as tubules. Cellular activity(s) of a particular cell-line can be assessed using in vitro assays, for example the assays disclosed herein.

Cancer: A malignant disease characterized by the abnormal growth and differentiation of cells. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubules (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melanoma).

Cell culture: The process by which either prokaryotic or eukaryotic cells are grown under controlled conditions. In practice the term "cell culture" has come to refer to the culturing of cells derived from multicellular eukaryotes, especially animal cells, such as mammalian cells, for example the fluorescent cells disclosed herein. Mammalian cells are grown and maintained at an appropriate temperature and gas mixture (typically, 37° C., 5% $CO_2$) in a cell incubator. Culture conditions vary widely for each cell type, and variation of conditions for a particular cell type can result in different phenotypes being expressed. Aside from temperature and gas mixture, the most commonly varied factor in culture systems is the growth medium. Recipes for growth media can vary in pH, glucose concentration, growth factors, and the presence of other nutrient components. The growth factors used to supplement media are often derived from animal blood, such as calf serum.

Some cells naturally live without attaching to a surface, such as cells that exist in the bloodstream. Others require a surface, such as most cells derived from solid tissues. Cells grown unattached to a surface are referred to as suspension cultures. Other adherent cultures cells can be grown on tissue culture plastic, which may be coated with extracellular matrix components (for example collagen or fibronectin) to increase its adhesion properties and provide other signals needed for growth. "Co-culture" refers to the culture of more than one cell-line (such as more than one of the disclosed cell-lines) in a single vessel. Co-cultures can be 2-dimensional (2-D) or 3-dimensional (3-D). Examples of both 2-D and 3-D co-cultures are described in U.S. patent application Ser. No. 12/802,666, filed on Jun. 10, 2010 *published as now U.S. Pat. No. 8,679,836 on Mar. 25, 2014).

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an angiogenesis inhibitor. Chemotherapeutic agents are described for example in Slapak and Kufe, *Principles of Cancer Therapy*, Chapter 86 in Harrison's Principles of Internal Medicine, 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy*, 2nd ed. St. Louis, Mosby-Year Book, 1995; Fischer Knobf, and Durivage (eds): *The Cancer Chemotherapy Handbook*, 4th ed. St. Louis, Mosby-Year Book, 1993. Combination chemotherapy is the administration of more than one agent to treat cancer, for example an alkylating agent and an angiogenesis inhibitor.

Contacting: To place in direct physical association, including in solid or in liquid form. Contacting can occur in vivo, for example by administering an agent to a subject, or in vitro for example with isolated cells or cell-cultures, for example cell-cultures of the disclosed fluorescent cell-lines.

Control: A reference standard. A control can be a known value indicative of basal cellular activity, such as basal migratory potential, doubling time, tubule formation potential and the like, or a control cell-culture, such as a culture including at least one of the disclosed fluorescent cell-lines, not treated with an exogenous agent, such as a test agent, one or more cell-lines (such as the fluorescent cell-lines disclosed herein), angiogenic factor, angiogenic inhibitor, or the like. A difference between a test sample and a control can be an increase or conversely a decrease. The difference can be a qualitative difference or a quantitative difference, for example a statistically significant difference. In some examples, a difference is an increase or decrease, relative to a control, of at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater then 500%.

Cycloalkyl: Includes a moiety that contains at least one cycloalkyl ring structure. There may be one or more ring structures including a bridged cyclic structure or a fused ring structure. The cycloalkyl may be unsubstituted or substituted with one or more substituents, e.g., halogen, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. Illustrative cycloalkyl groups include cyclopropyl, cyclopentyl, cyclohexyl, cyclobutyl, and decahydronaphthyl.

EC50: The term half maximal effective concentration (EC50 or $EC_{50}$) refers to the concentration of a drug which induces a response halfway between the baseline and maximum. EC50 is commonly used as a measure of drug potency.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite one fluorophore with a specific excitation wavelength but not excite a second fluorophore with a specific excitation wavelength difference and distinct from the excitation wavelength on the first fluorophore.

Emission or emission signal: The light of a particular wavelength generated from a source. In particular examples, an emission signal is emitted from a fluorophore, such as a fluorescent protein, after the fluorophore absorbs light at its excitation wavelength(s).

Excitation or excitation signal: The light of a particular wavelength necessary and/or sufficient to excite an electron transition to a higher energy level. In particular examples, an excitation is the light of a particular wavelength necessary and/or sufficient to excite a fluorophore, such as a fluorescent protein, to a state such that the fluorophore will emit a different (such as a longer) wavelength of light then the wavelength of light from the excitation signal.

Exogenous agent: An exogenous agent is any agent external to a target cell-line that is to be studied, and it includes small molecules, proteins, biological samples (such as patient samples) and other cells or cell-lines, such as fluorescent cell-lines other than the target cell-line, for example a different type of cell that can by identified as different by a distinguishable fluorescent signal.

Expression: With respect to a gene sequence, refers to transcription of the gene and, as appropriate, translation of the resulting mRNA transcript to a protein. Thus, expression of a protein coding sequence, such as the expression of a fluorescent protein, results from transcription and translation of the coding sequence for that protein. Constitutive expression refers to the expression of a gene product, such as a protein, for example a fluorescent protein, in a substantial continuous manner, such that the expression is not interrupted. An example of constitutive expression is continuous expression in the absence of an exogenous stimulating agent, such as an agent used to activate a promoter. Stable expression refers to expression that is not lost or reduced substantially over time, for example expression that does not diminish through multiple passages of a cell-line, for example a cell-line constitutively expressing a fluorescent protein.

Fluorescent property: A characteristic of a fluorescent molecule, such as a fluorescent protein, for example green fluorescent protein, red fluorescent protein, yellow fluorescent protein, cyan fluorescent protein and the like. Examples of fluorescent properties include the molar extinction coefficient at an appropriate excitation wavelength, the fluorescence quantum efficiency, the shape of the excitation spectrum or emission spectrum (the "fluorescence spectrum," the excitation wavelength maximum and emission wavelength maximum, the ratio of excitation amplitudes at two different wavelengths, the ratio of emission amplitudes at two different wavelengths, the excited state lifetime, or the fluorescence anisotropy. Quantifying fluorescence refers to the determination of the amount of fluorescence generated by a fluorophore, for example a fluorescent protein, which can be the quantity of photons emitted by a fluorophore. In some examples, fluorescence is quantified by measuring the intensity of a fluorescence signal at a particular wavelength, for example the wavelength of the emission maxima of a particular fluorophore, such as a fluorescent protein. Fluorescence intensity can also be quantified at a wavelength that is not the emission maxima of a particular fluorophore, for example to avoid emission spectra that overlap and thereby interfere with the emission maxima of a particular fluorophore, such as a particular fluorescent protein. In some examples, a fluorescence signal is emitted by a population of fluorescent proteins, for example fluorescent proteins present in a population of cells containing such fluorescent proteins. Such a signal can be quantified, for example to determine the number, or relative number of cells that emit such a fluorescent signal. Detecting a pattern of fluorescence refers to the correlation of a fluorescent signal to a specific location to determine the location where a fluorescence signal, such as a fluorescent signal of a particular wavelength, originates. In some examples, a pattern of fluorescence determines the location and or shape of the cells that emit a fluorescence signal, such as cells containing a fluorescent protein, for example to determine the number of the total area of the tubules, the total number of tubules, number of nodes, number of branch points, the number of tubes per node, or node area formed by such cells using the methods disclosed herein, and disclosed in U.S. application Ser. No. 12/060,752 (published as US 2009/0088341 on Apr. 2, 2009; and incorporated herein by reference in its entirety).

Fluorescent protein: A protein capable of emission of a detectable fluorescent signal. Fluorescent proteins can be characterized by the wavelength of their emission spectrum. For example green fluorescent protein (GFP) has a fluorescent emission spectrum in the green part of the visible spectrum. In addition to green-fluorescent proteins, fluorescent proteins are known which fluoresce in other regions of the visible spectrum, for example blue-fluorescent proteins, cyan-fluorescent proteins, yellow-fluorescent proteins, orange-fluorescent proteins, red-fluorescent proteins, and far-red fluorescent proteins. Examples of fluorescent proteins can be found in the following patent documents: U.S. Pat. Nos. 5,804,387; 6,090,919; 6,096,865; 6,054,321; 5,625,048; 5,874,304; 5,777,079; 5,968,750; 6,020,192; 6,146,826; 6,969,597; 7,150,979; 7,157,565; and 7,166,444; and published international patent applications WO 07/085,923; WO 07/052,102, WO 04/058973, WO 04/044203, WO 03/062270; and WO 99/64592. Additional examples of fluorescent proteins are available from Clonetech, Laboratories, Inc. (Mountain View, Calif.) under the trade name Living Colors®. Nucleic acids encoding such fluorescent proteins can be incorporated into mammalian expression vectors for use in producing the disclosed fluorescent cell-lines.

Growth rate: The expansion of the number of cells of a specified cell-line through cell division as a function of time. In one example the growth rate is the rate at which a cell-line grown in culture doubles.

Halogen: Refers to fluoro, bromo, chloro and iodo substituents.

High throughput technique: Through this process one can rapidly identify active compounds, antibodies or genes which affect a particular biomolecular pathway, for example pathways in angiogenesis. In certain examples, combining modern robotics, data processing and control software, liquid handling devices, and sensitive detectors, high throughput techniques allows the rapid screening of potential pharmaceutical agents in a short period of time.

Histology: The study of the microscopic anatomy and classification of tissue, including the histology of mammalian cells, such as cells and cell-lines from mammalian tissues. Histological typing refers to the categorizing of tissue into histological types, for example by microanatomical origin (such as connective tissue, nerves, muscles, and circulatory cells, among others) or cell-types (such as epithelial cells, stromal cells among others). Cells can be classified as being of different histological types by virtue of the staining and/or reaction with antibodies, or by characteristic microanatomical features. Cells of different histological types interact differently with different stains and/or antibodies. Methods for histological typing are well known in the art. Histology can be use to determine if cells are of different types. Thus, in some examples different cell-lines are histologically different cell-lines.

Immortalized cell or cell-line: A cell or cell-line that has acquired the ability to proliferate indefinitely either through random mutation or deliberate modification, such as artificial expression of the telomerase gene. There are numerous well established immortalized cell-lines representative of particular cell types.

Inhibitor (for example, of angiogenesis): A substance capable of inhibiting [something] to some measurable extent, for example angiogenesis. In disclosed examples, inhibition of angiogenesis is measured in one of the assays disclosed herein.

Mammal: This term includes both human and non-human mammals. Similarly, the term "subject" includes both human and veterinary subjects, for example, humans, non-human primates, mice, rats, dogs, cats, horses, and cows.

Migration potential: The ability of cells, such as the cell-line disclosed herein, to translocate in response to a chemical stimulus, such as a growth factor. Migration potential can be determined with the assays disclosed herein.

Mixed cell population: A population of cells, such as cells in culture, that contains two or more different types of cells, such as histologically different cell-lines. Examples of different types of cells include cells of different embryonic origin (such as cells originating from the ectoderm, endoderm, or mesoderm), cells from different cellular locations (such as cells from epithelium, endothelium, or stroma), cells from different tissues or organs (such as cells from pulmonary myocardial, neural, vascular, skin, bone, or skeletal or smooth muscle tissue).

Neoplasm or tumor: Any new and abnormal growth; particularly a new growth of tissue in which the growth is uncontrolled and progressive. A neoplasm, or tumor, serves no useful function and grows at the expense of the healthy organism.

In general, tumors appear to be caused by abnormal regulation of cell growth. Typically, the growth of cells in the body is strictly controlled; new cells are created to replace older ones or to perform new functions. If the balance of cell growth and death is disturbed, a tumor may form. Abnormalities of the immune system, which usually detects and blocks aberrant growth, also can lead to tumors. Other causes include radiation, genetic abnormalities, certain viruses, sunlight, tobacco, benzene, certain poisonous mushrooms, and aflatoxins.

Tumors are classified as either benign (slow-growing and usually harmless depending on the location), malignant (fast-growing and likely to spread and damage other organs or systems) or intermediate (a mixture of benign and malignant cells). Some tumors are more common in men or women, some are more common amongst children or elderly people, and some vary with diet, environment and genetic risk factors.

Symptoms of neoplasms depend on the type and location of the tumor. For example, lung tumors can cause coughing, shortness of breath, or chest pain, while tumors of the colon can cause weight loss, diarrhea, constipation and blood in the stool. Some tumors produce no symptoms, but symptoms that often accompany tumors include fevers, chills, night sweats, weight loss, loss of appetite, fatigue, and malaise.

Blood vessels supply tumors with nutrients and oxygen. Tumor growth is dependent on the generation of new blood vessels that can maintain the needs of the growing tumor, and many tumors secrete substances (angiogenic factors) that are able to induce proliferation of new blood vessels (angiogenesis). Anti-tumor therapies include the use of angiogenesis inhibitors, which reduce the formation of blood vessels in the tumor, effectively starving the tumor and/or cause the tumor to drown in its own waste.

Neovascularization: The growth of new blood vessels. Neovascularization can be the proliferation of blood vessels in tissue not normally containing them, or the proliferation of blood vessels in an ischemic or otherwise damaged tissue. Neovascularization can be pathological when it is unwanted or mediates a pathological process, for example when it occurs in the retina or cornea.

Passaging cells: Passaging or splitting cells involves transferring a small number of cells into a new vessel. Cells can be cultured for a longer time if they are split regularly, as it avoids the senescence associated with prolonged high cell density. Suspension cultures are easily passaged with a small amount of culture containing a few cells diluted in a larger volume of fresh media. For adherent cultures, cells first need to be detached; which is typically done with a mixture of trypsin-EDTA. A small number of detached cells can then be used to seed a new culture.

Pharmaceutical agent or drug: A chemical compound or composition capable of inducing a desired therapeutic or prophylactic effect when properly administered to a subject (such as the inhibition of angiogenesis), alone or in combination with another therapeutic agent(s) or pharmaceutically acceptable carriers. Pharmaceutical agents include, but are not limited to, angiogenic factors, for example bFGF, and VEGF, and anti-angiogenic factors, such as inhibitors of bFGF, or VEGF. For example, suitable anti-angiogenic factors include, but are not limited to, SU5416, which is a specific VEGF-R antagonist, SU6668 which blocks the receptors for VEGF, bFGF, and PDGF and Avastin®. See, for example, Liu et al., *Seminars in Oncology* 29 (Suppl 11): 96-103, 2002; Shepherd et al., *Lung Cancer* 34:S81-S89, 2001. The term pharmaceutical agent also can be applied to the bioactive compounds discussed herein, including specifically the anti-angiogenic compounds listed in TABLE 1, and characterized in TABLE 10.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Primary cells: Cells that are cultured directly from a subject. With the exception of some derived from tumors, most primary cell cultures have limited lifespan. After a certain number of population doublings cells undergo the process of senescence and stop dividing, while generally retaining viability.

Signal: A detectable change or impulse in a physical property that provides information. In the context of the disclosed methods, examples include electromagnetic signals, such as light, for example light of a particular quantity or wavelength, for example a wavelength of light emitted from a fluorescent protein.

Small molecule inhibitor (for example, of an inhibitory of angiogenesis): A molecule, typically with a molecular weight less than 1000 Daltons, or in some embodiments, less than about 500 Daltons, wherein the molecule is capable of inhibiting, to some measurable extent, an activity of some target molecule. In particular embodiments, the small molecule inhibitor is an inhibitor of angiogenesis, which activity can be tested, detected, determined, and/or measured using methods known in the art and/or described herein.

Test agent: Any agent that is tested for its effects, for example its effects on a cell. In some embodiments, a test agent is a chemical compound, such as an antiangiogenic agent or even an agent with unknown biological properties.

Therapeutically effective amount/dose: A dose sufficient to have a therapeutic effect, for example to inhibit to some degree advancement, or to cause regression of the disease, or which is capable of relieving symptoms caused by the disease. For example, a therapeutically effective amount of an angiogenesis inhibitor can vary from about 0.1 nM per kilogram (kg) body weight to about 1 µM per kg body weight, such as about 1 nM to about 500 nM per kg body weight, or about 5 nM to about 50 nM per kg body weight. The exact dose of a particular therapeutic/bioactive compound is readily determined by one of skill in the art based on the potency of the compound, the age, weight, sex and physiological condition of the subject, the disease being treated, and so forth.

Treating: Inhibiting the full development of a disease or condition, for example, in a subject who is at risk for a disease such as cancer. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Tubule formation potential: The ability of a cell-line to form a tube-like structure in vitro, for example a structure similar to a blood vessel, such as a capillary. Tubule formation potential can be determined by determining the pattern displayed by cells which have been induced to form tubules, for example by determining the pattern of fluorescence from cells expressing fluorescent proteins, such as the cell-lines disclosed herein.

III. Description of Several Embodiments

Described herein is a stringent HTS strategy which, together with advanced bioinformatics mining tools, was used to identify a new set of antiangiogenic small molecules. The strategy included the following:

Two cell-based HTS were designed to identify small molecules that block the main steps of the angiogenic process: growth of endothelial cells and tube formation. In both assays, compounds were tested at a low final concentration (1 µM) to avoid false positives. The following classes of bioactive SMs were identified in these assays: 48 growth inhibitors, 35 tube formation inhibitors. 11 SMs block both growth and tube formation. 3 SMs have been identified as specific inhibitors of tumor growth; these compounds are not antiangiogenic but are antitumoral. See TABLE 10 for a summary of the HTS results.

All bioactive compounds were tested for their ability to induce cytotoxicity and apoptosis in endothelial cells. Three out the 77 small molecules were cytotoxic. These cytotoxic SMs were not considered for in vivo experiments. Another three SM showed 5-8 fold increase in apoptotic potential, and 11 showed a 2-3 fold increase (see TABLE 10).

Structure similarity analysis has revealed that most of the bioactive SMs (68) are not structurally related to existing FDA marketed antiangiogenic SMs, SMs currently in clinical trials or SMs annotated as angiogenesis modulators in PubChem, DrugBank, LeadScope, etc. Therefore, based on structure-activity relationship (SAR), the compounds identified herein (see TABLE 1) represent a new set of antiangiogenic compounds functionally unrelated to known antiangiogenic SMs. Additional SAR analysis has identified a number of scaffolds which correlate with inhibitory activity of both endothelial cell growth and endothelial cell tube formation (see TABLES 2-9).

Structure-activity-relationship (SAR) studies have shown a potential mechanism of action for some (14) of the SMs of interest. For instance, the structure of some of the growth inhibitors is consistent with topoisomerase II inhibitory activity while some tube formation inhibitors show structures consistent with known tubulin binders. See TABLE 10.

Comparison of the growth inhibitory activity of these compounds in endothelial cells and tumor cells has allowed their classification in several groups including: 1) SMs able to inhibit the growth of both endothelial cells and tumor cells (Compounds 1-73); and 2) SMs which inhibit the growth of tumor cells but not endothelial cells (Compounds 74-77).

Thus, described herein are compounds that exhibit inhibition of undesirable angiogenesis, and methods for using these compounds to treat angiogenesis-dependent diseases or neoplasms (e.g., solid tumors). In particular, the presently disclosed method provides for inhibiting unwanted angiogenesis in a human or animal by administering to the human or animal with the undesired angiogenesis a composition comprising an effective amount of at least one of the compounds described herein, such as specifically one or more of Compounds 1 through 77 as shown in TABLE 1. Examples of such methods involve inhibiting angiogenesis by exposing a tissue or cell mass having the undesirable angiogenesis to an angiogenesis inhibiting amount of one or more compounds, or pharmaceutically acceptable salts or derivatives of such compounds, wherein such compounds are selected from those of Compounds 1 through 77 as shown in TABLE 1.

It will be recognized that although the compounds disclosed herein exhibit antiangiogenic properties, the mechanism for specific action by the compounds are not necessarily limited to antiangiogenic mechanisms. For example, the compounds may also exhibit cytotoxic properties (that may be independent of any antiangiogenic properties) that are useful for treating neoplasms.

Antiangiogenic drugs are among the most promising agents for the clinical management of cancer and other angiogenesis related diseases, such as endometriosis. A multibillion dollar market has developed over the past decade involving innumerable pharmaceutical companies that are in the process of developing or attempting to develop antiangiogenic SMs.

Recent advances in the understanding of the angiogenic process have impelled the development of a new group of antiangiogenic SMs. Most of the antiangiogenic SMs currently being considered in the clinic are tubulin binders or target the tyrosine kinase activity of cell surface receptors involved in the angiogenic process such as the VEGF receptor. Some of these compounds (such as inhibitors of the VEGF pathway) have already shown limited clinical success in the management of angiogenesis-related diseases, mainly cancer.

In contrast to the antiangiogenic SMs that were previously identified, the innovative approach to identifying antiangiogenic compounds described herein is not restricted by the subcellular target, rather it targets the main cellular processes involved in angiogenesis. Therefore, this method has permitted the discovery of novel SM that are not related to tyrosine kinase inhibitors, tubulin binders or any other known antiangiogenic SM currently in development. Additionally this highly stringent screening design guarantees the absence of "false positives," which commonly represent a major obstacle in HTS.

Therefore, the newly identified SMs provided herein (e.g., Compounds 1-77) represent new groups of high quality compound leads, defining new antiangiogenic subcellular targets and opening up the possibility of developing drugs based on mechanism of action alternative to the ones currently being considered by academic institutions and private pharmaceutical industry.

In addition, the screen employed herein has provided information about the specificity of the growth inhibitory activity of some of the bioactive SMs. For instance, some molecules have been found which inhibit the growth of tumor cells while having no substantial effect on endothelial cells. This enables advanced combinatorial drug regimens. For instance, in the treatment of angiogenesis-dependent tumors it may sometimes be important to deliver first drugs that inhibit tumor growth but do not affect endothelial cells (which are the main components of the vasculature), since drugs are delivered through the tumor vasculature and a functional vasculature is needed for drug delivery. Therefore, drugs like those found in this study with the ability to specifically inhibit tumor growth, but not endothelial cell growth (e.g., Compounds 74-77) would be of great value for such treatment. Once the tumor has been significantly reduced, drugs with inhibitory activity in both tumor cells and endothelial cells might be preferred, since both tumor cells and endothelial cells need to be targeted. A number of such drugs have also been found in this study (for instance, Compounds 1-37 and 63-73). Therefore, the SM specificity information obtained in this study will be very useful in the development of anticancer SM therapies.

The bioactive SMs identified herein represent candidates to be applied to the clinical management of a variety of angiogenesis related diseases including (but not limited to) cancer, endometriosis, diabetic retinopathy, age-related macular degeneration, etc.

Thus, disclosed herein are pharmaceuticals composition for treating an angiogenesis-dependent disease, comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically-acceptable salt thereof. In particular examples, the pharmaceutical compositions further comprising [4-[(4-arsonophenyl)methyl]phenyl]arsonic acid (NSC 48300), or a pharmaceutically-acceptable salt thereof. In other examples, the angiogenesis-dependent disease comprises cancer, retinopathy, endometriosis, arthritis, or psoriasis. In further examples, the composition is administered topically, intravenously, orally, parenterally, or as an implant. In still other examples, the pharmaceutical composition further comprises an additional angiogenesis inhibitor.

Also disclosed herein are pharmaceutical compositions for inhibiting aberrant angiogenesis, comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically-acceptable salt thereof. In some examples, the pharmaceutical compositions further comprise [4-[(4-arsonophenyl)methyl]phenyl]arsonic acid (NSC 48300), or a pharmaceutically-acceptable salt thereof. In some examples, the aberrant angiogenesis is stimulated by a tumor, which can be benign or malignant.

Also disclosed herein are pharmaceutical compositions for inhibiting growth of neoplastic tissue, comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically-acceptable salt thereof. In particular examples, the pharmaceutical compositions further comprise [4-[(4-arsonophenyl)methyl]phenyl]arsonic acid (NSC 48300), or a pharmaceutically-acceptable salt thereof.

Additionally disclosed are methods of treating an angiogenesis-dependent disease, comprising: administering to a subject having or predisposed to an angiogenesis-dependent disease a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular examples, the composition further comprises [4-[(4-arsonophenyl)methyl]phenyl]arsonic acid (NSC 48300), or a pharmaceutically-acceptable salt thereof. In further examples, the angiogenesis-dependent disease comprises cancer, retinopathy, endometriosis, arthritis, or psoriasis. In some examples, the composition is administered topically, intravenously, orally, parenterally, or as an implant.

In still other examples, the methods further comprise administering to the subject an additional angiogenesis inhibitor, such as an inhibitor of bFGF, FGF, or VEGF.

Also disclosed herein are methods of inhibiting undesired angiogenesis in a subject, comprising: identifying a subject wherein angiogenesis is not desired, and administering to the subject a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular examples, the composition further comprises [4-[(4-arsonophenyl)methyl]phenyl]arsonic acid (NSC 48300), or a pharmaceutically-acceptable salt thereof. In other examples, the method further comprises administering an additional inhibitor of angiogenesis, such as an inhibitor of bFGF, FGF, or VEGF. In some examples, the undesired angiogenesis comprises tumor angiogenesis, for example wherein the tumor is benign or malignant.

Further disclosed herein are methods of inhibiting a neoplasm in a subject, comprising: administering to the subject a therapeutically effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. In particular examples, the composition further comprises [4-[(4-arsonophenyl)methyl]phenyl]arsonic acid (NSC 48300), or a pharmaceutically-acceptable salt thereof.

Lastly, disclosed herein are methods of inhibiting angiogenesis in a tissue or a target area in a subject wherein the formation of new blood vessels is not desired, comprising identifying a tissue or target area in a subject wherein the formation of new blood vessels is not desired; and introducing directly or indirectly into the tissue or target area an effective amount of a composition comprising at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof, thereby inhibiting angiogenesis in the tissue or target area. In particular examples, the composition further comprises [4-[(4-arsonophenyl)methyl]phenyl]arsonic acid (NSC 48300), or a pharmaceutically-acceptable salt thereof. In some examples, the target area comprises skin, a tumor, a retina, a joint, or endometrial tissue. In other examples, the subject has or is predisposed to developing a tumor, retinopathy, endometriosis, arthritis, or psoriasis.

IV. Bioactive Molecules

A set of diverse chemical compounds (Diversity Set I) was obtained from the NCI/DTP Open Chemical Repository (available on-line at dtp.cancer.gov). Diversity Set I included 1990 compounds, each of which contains at least five new pharmacophores and five or fewer rotatable bonds as determined by the Chem-X program (Oxford Molecular Group, Oxford, UK). Although Diversity Set I is no longer available as a set, individual compounds can be obtained from the NIC/DTP Open Chemical Repository (though large amounts of NSC 675865, NSC 18877, NSC 176327, NSC 521777, NSC 166687, and NSC 119889 are not available). It will be understood by one of skill in the art that each member of Diversity Set I represents a large family of molecules, information related to which can be accessed through public databases. With the identification herein of the antiangiogenic activity of representative Compounds 1-77, methods of testing each related class of molecules for antiangiogenic activity are now enabled, as is use of any molecules identified through such screening as antiangiogenic agents. Structure similarity analyses, including structure-activity relationship analysis as described below in Section V, will be used to identify additional compounds that could potentially show antiangiogenic activity. Such analysis will enable the screening of compounds that are not associated with the Diversity Set I families, but are available through public databases.

The compounds in Diversity Set I were screened for potential antiangiogenic activity, as provided herein. Table 1 includes 77 compounds from Diversity Set I that were discovered to inhibit (1) endothelial cell growth, (2) tube formation, (3) endothelial cell growth and tube formation, or (4) specific tumor cell growth without concomitant endothelial cell growth inhibition. Specifically, compounds 1-37 are endothelial cell growth inhibitors, compounds 38-62 are tube formation inhibitors, compounds 63-73 are both endothelial cell growth and tube formation inhibitors, and compounds 74-77 are specific tumor cell growth inhibitors. Of the 77 compounds found to be bioactive in the screening assays, compounds 63, 64, 67, 69, and 71 are considered to be of particular interest. Each of these compounds inhibited both endothelial cell growth and tube formation without cytotoxicity (less than 10% cytotoxicity is considered to be a basal level).

TABLE 1

BIOACTIVE SMALL MOLECULES

| Compound | Structure | NSC Number/Nomenclature |
|---|---|---|
| 1 | 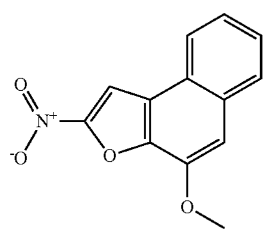 [SMILES: COc1cc2ccccc2c2cc([N+](=O)[O-])oc12] | NSC 329226<br>4-methoxy-2-nitrobenzo[e][1]benzofuran |
| 2 | 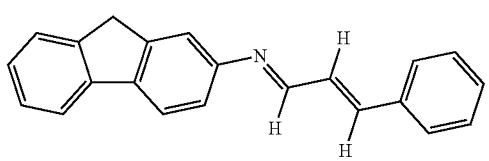 [SMILES: C(=C\c1ccccc1)/C=N/c1ccc2c(c1)Cc1ccccc1-2] | NSC 15234<br>(E)-N-(9H-fluoren-2-yl)-3-phenylprop-2-en-1-imine |
| 3 | 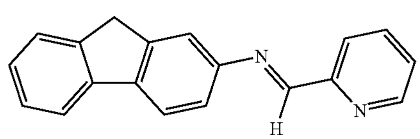 [SMILES: C(=N\c1ccc2c(c1)Cc1ccccc1-2)/c1ccccn1] | NSC 15226<br>N-(9H-fluoren-2-yl)-1-pyridin-2-ylmethanimine |
| 4 | 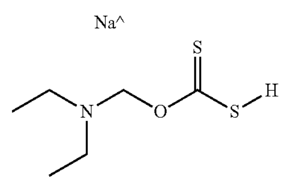 | NSC 24076<br>diethylaminomethoxymethanedithioic acid; sodium |
| 5 | 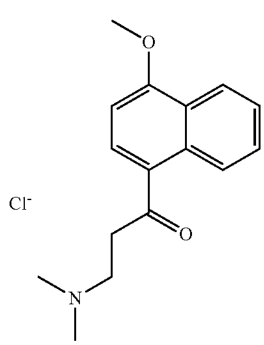 [SMILES: [Cl-] ; COc1ccc(C(=O)CCN(C)C)c2ccccc12] | NSC 26081<br>3-(dimethylamino)-1-(4-methoxynaphthalen-1-yl)propan-1-one chloride |

TABLE 1-continued

BIOACTIVE SMALL MOLECULES

| Compound | Structure | NSC Number/Nomenclature |
|---|---|---|
| 6 | 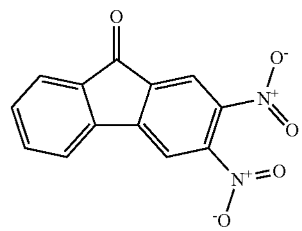 [SMILES: O=C1c2ccccc2-c2cc([N+](=O)[O-])c([N+](=O)[O-])cc21] | NSC 133896<br>2,3-dinitrofluoren-9-one |
| 7 | 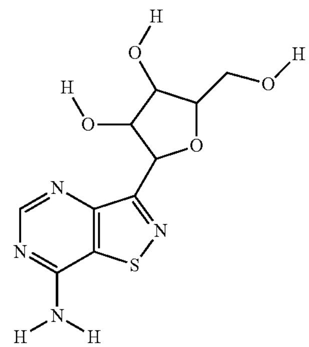 [SMILES: Nc1ncnc2c(C3OC(CO)C(O)C3O)nsc12] | NSC 675865<br>2-(7-amino-[1,2]thiazolo[4,5-d]pyrimidin-3-yl)-5-(hydroxymethyl)oxolane-3,4-diol |
| 8 | 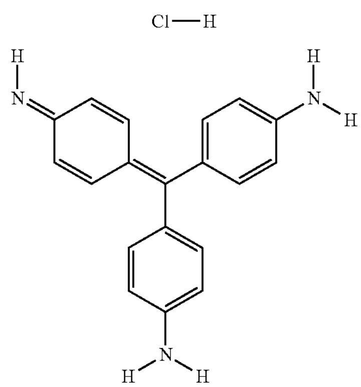 [SMILES: Cl ; N=C1C=CC(=C(c2ccc(N)cc2)c2ccc(N)cc2)C=C1] | NSC 10460<br>[4-[(4-aminophenyl)-(4-iminocyclohexa-2,5-dien-1-ylidene)methyl]phenyl]azanium chloride |
| 9 | 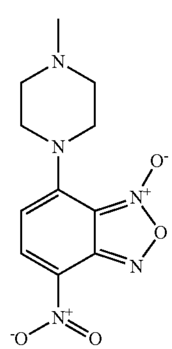 [SMILES: CN1CCN(c2ccc([N+](=O)[O-])c3no[n+]([O-])c23)CC1] | NSC 207895<br>7-(4-methylpiperazin-1-yl)-4-nitro-1-oxido-2,1,3-benzoxadiazol-1-ium |

TABLE 1-continued

BIOACTIVE SMALL MOLECULES

| Compound | Structure | NSC Number/Nomenclature |
|---|---|---|
| 10 | 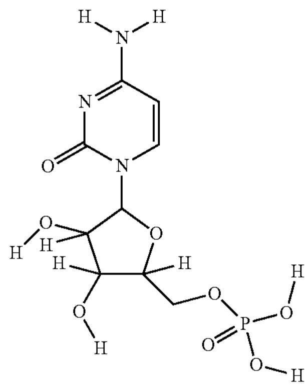 [SMILES: Nc1ccn(C2OC(COP(=O)(O)O)C(O)C2O)c(=O)n1] | NSC 99445<br>[5-(4-amino-2-oxopyrimidin-1-yl)-3,4-dihydroxyoxolan-2-yl]methyl dihydrogen phosphate |
| 11 | 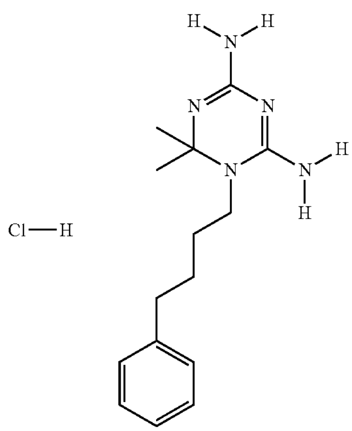 [SMILES: Cl ; CC1(C)N=C(N)N=C(N)N1CCCCc1ccccc1] | NSC 88903<br>6,6-dimethyl-1-(4-phenylbutyl)-1,3,5-triazine-2,4-diamine hydrochloride |
| 12 | 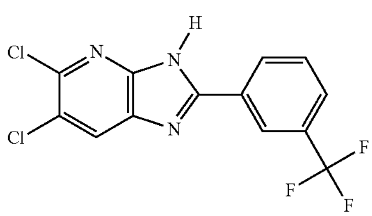 [SMILES: FC(F)(F)c1cccc(-c2nc3cc(Cl)c(Cl)nc3[nH]2)c1] | NSC 177407<br>5,6-dichloro-2-[3-(trifluoromethyl)phenyl]-1H-imidazo[4,5-b]pyrazine |
| 13 | 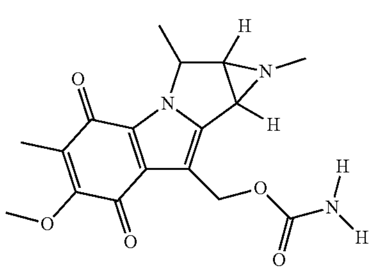 [SMILES: COC1=C(C)C(=O)c2c(c(COC(N)=O)c3n2C(C)C2C3N2C)C1=O] | NSC 123111<br>(6-Methoxy-1,5-dimethyl-4,7-dioxo-1,1a,2,4,7,8b-hexahydroazireno[2',3':3,4]pyrrolo[1,2-a]indol-8-yl)methyl carbamate |

TABLE 1-continued

BIOACTIVE SMALL MOLECULES

| Compound | Structure | NSC Number/Nomenclature |
|---|---|---|
| 14 | 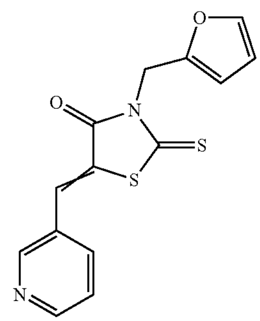 [SMILES: O=C1C(=Cc2cccnc2)SC(=S)N1Cc1ccco1] | NSC 329261<br>3-(furan-2-ylmethyl)-5-(pyridin-3-ylmethylidene)-2-sulfanylidene-1,3-thiazolidin-4-one<br>(The crossed bond represents a double bond for which the cis- or trans- structure is unknown or can be either.) |
| 15 | 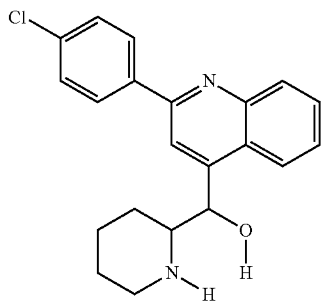 [SMILES: OC(c1cc(-c2ccc(Cl)cc2)nc2ccccc12)C1CCCCN1] | NSC 13316<br>[2-(4-chlorophenyl)quinolin-4-yl]-piperidin-2-ylmethanol |
| 16 | 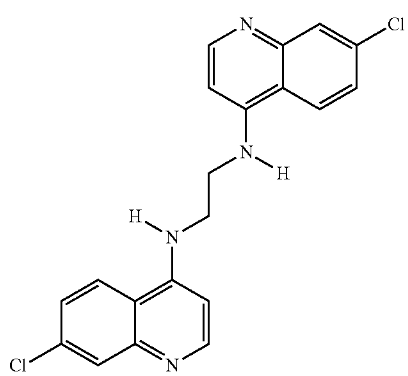 [SMILES: Clc1ccc2c(NCCNc3ccnc4cc(Cl)ccc34)ccnc2c1] | NSC 5844<br>N-N'-bis(7-chloroquinolin-4-yl)ethane-1,2-diamine |
| 17 | 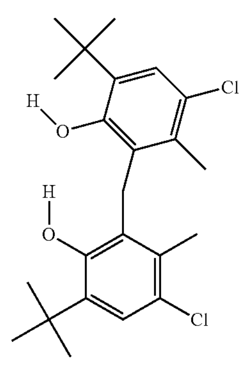 [SMILES: Cc1c(Cl)cc(C(C)(C)C)c(O)c1Cc1c(C)c(Cl)cc(C(C)(C)C)c1O] | NSC 5857<br>6-tert-butyl-2-[(3-tert-butyl-5-chloro-2-hydroxy-6-methylphenyl)methyl]-4-chloro-3-methylphenol |

TABLE 1-continued

BIOACTIVE SMALL MOLECULES

| Compound | Structure | NSC Number/Nomenclature |
|---|---|---|
| 18 | 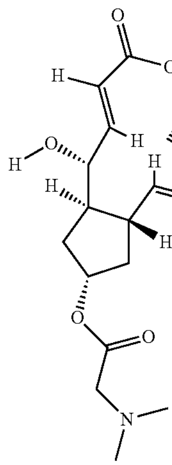 | NSC 656202<br>[(1R,2R,3E,7S,11E,13S,15S)-2-hydroxy-7-methyl-5-oxo-6-oxabicyclo[11.3.0]hexadeca-3,11-dien-15-yl] 2-(dimethylamino)acetate |
| 19 | 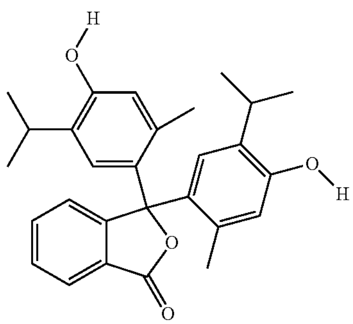 [SMILES: Cc1cc(O)c(C(C)C)cc1C1(c2cc(C(C)C)c(O)cc2C)OC(=O)c2ccccc21] | NSC 2186<br>3,3-bis(4-hydroxy-2-methyl-5-propan-2-ylphenyl)-2-benzofuran-1-one |
| 20 | 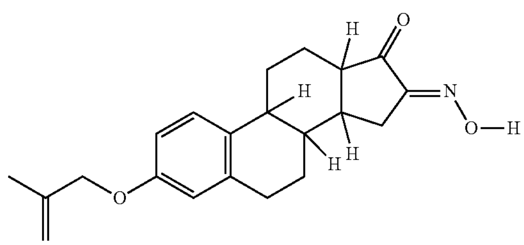 | NSC 97845<br>(16E)-16-hydroxyimino-13-methyl-3-(2-methylprop-2-enoxy)-6,7,8,9,11,12,14,15-octahydrocyclopenta[a]phenanthren-17-one |
| 21 | 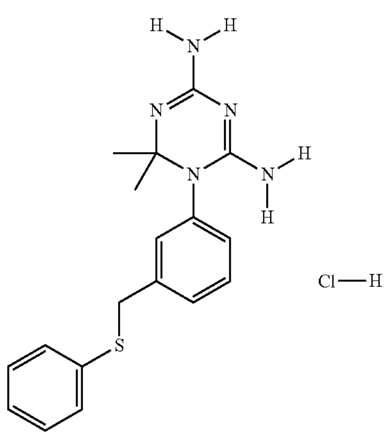 [SMILES: CC1(C)N=C(N)N=C(N)N1c1cccc(CSc2ccccc2)c1 ; Cl] | NSC 368891<br>6,6-dimethyl-1-[3-(phenylsulfanylmethyl)-phenyl]-1,3,5-triazine-2,4-diamine hydrochloride |

TABLE 1-continued

BIOACTIVE SMALL MOLECULES

| Compound | Structure | NSC Number/Nomenclature |
|---|---|---|
| 22 | 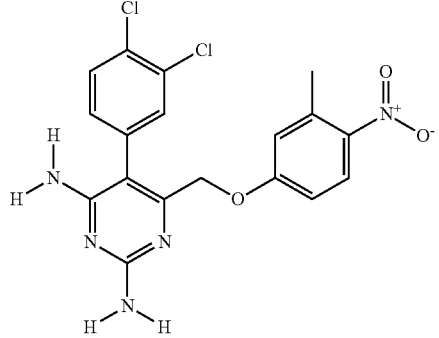 [SMILES: Cc1cc(OCc2nc(N)nc(N)c2-c2ccc(Cl)c(Cl)c2)ccc1[N+](=O)[O-]] | NSC 126710<br>5-(3,4-dichlorophenyl)-6-[(3-methyl-4-nitrophenoxy)methyl]pyrimidine-2,4-diamine |
| 23 | 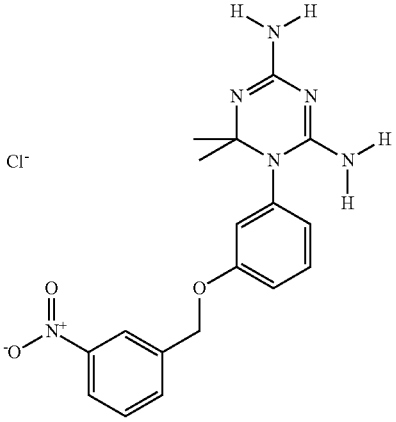 [SMILES: [Cl-] ; CC1(C)N=C(N)N=C(N)N1c1cccc(OCc2cccc([N+](=O)[O-])c2)c1] | NSC 109836<br>6,6-dimethyl-1-[3-[(3-nitrophenyl)methoxy]-phenyl]-1,3,5-triazine-2,4-diamine chloride |
| 24 | 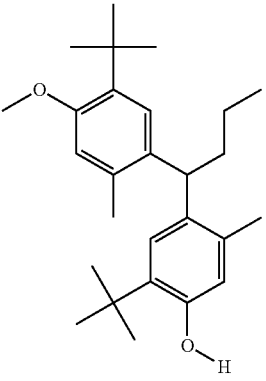 [SMILES: CCCC(c1cc(C(C)(C)C)c(O)cc1C)c1cc(C(C)(C)C)c(OC)cc1C] | NSC 67485<br>2-tert-butyl-4-[1-(5-tert-butyl-4-hydroxy-2-methylphenyl)butyl]-5-methylphenol |
| 25 | 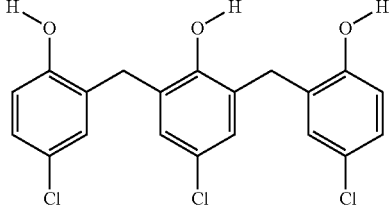 [SMILES: Oc1ccc(Cl)cc1Cc1cc(Cl)cc(Cc2cc(Cl)ccc2O)c1O] | NSC 47932<br>4-chloro-2,6-bis[(5-chloro-2-hydroxyphenyl)methyl]phenol |

TABLE 1-continued

BIOACTIVE SMALL MOLECULES

| Compound | Structure | NSC Number/Nomenclature |
|---|---|---|
| 26 | 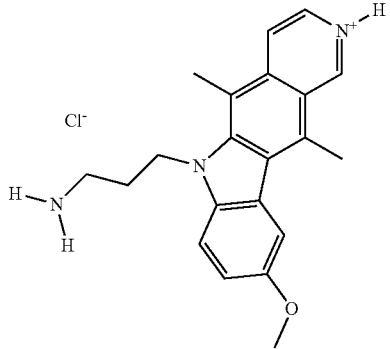 [SMILES: COc1ccc2c(c1)c1c(C)c3c[nH+]ccc3c(C)c1n2CCCN ; [Cl-]] | NSC 176327<br>3-(9-methoxy-5,11-dimethylpyrido[4,3-b]carbazol-2-ium-6-yl)propan-1-amine chloride |
| 27 | 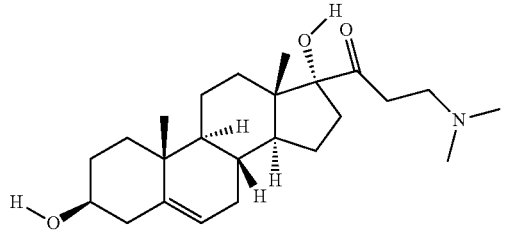 | NSC 48630<br>1-[(3S,8R,9S,10R,13S,14S,17R)-3,17-dihydroxy-10,13-dimethyl-1,2,3,4,7,8,9,11,12,14,15,16-dodecahydrocyclopenta[a]phenanthren-17-yl]-3-(dimethylamino)propan-1-one chloride |
| 28 | 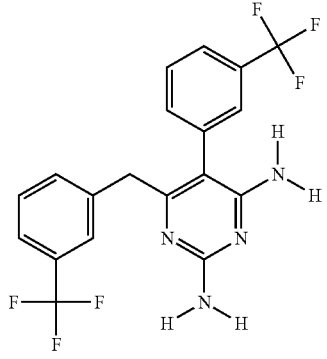 [SMILES: Nc1nc(N)c(-c2cccc(C(F)(F)F)c2)c(Cc2cccc(C(F)(F)F)c2)n1] | NSC 71669<br>5-[3-(trifluoromethyl)phenyl]-6-[[3-(trifluoromethyl)phenyl]methyl]pyrimidine-2,4-diamine |
| 29 | 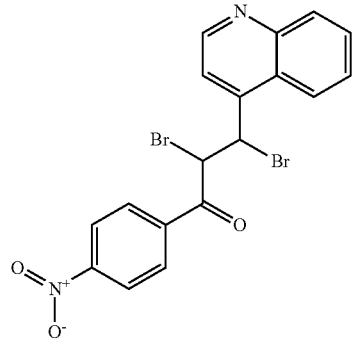 [SMILES: O=C(c1ccc([N+](=O)[O-])cc1)C(Br)C(Br)c1ccnc2ccccc12] | NSC 150289<br>2,3-dibromo-1-(4-nitrophenyl)-3-quinolin-4-ylpropan-1-one |

TABLE 1-continued
BIOACTIVE SMALL MOLECULES
| Compound | Structure | NSC Number/Nomenclature |
|---|---|---|
| 30 | 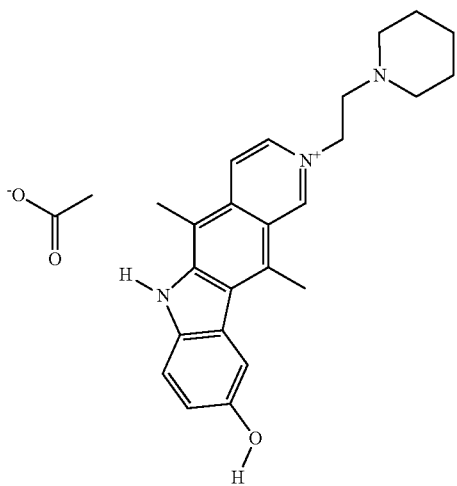 | NSC 311153<br>5,11-dimethyl-2-(2-piperidin-1-ylethyl)-6H-pyrido[4,3-b]carbazol-2-ium-9-ol acetate |
| 31 | 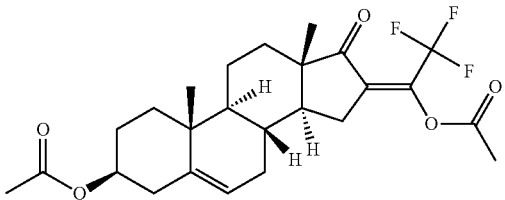 | NSC 45238<br>[(3S,8R,9S,10R,13S,14S,16E)-16-(1-acetyloxy-2,2,2-trifluoroethylidene)-10,13-dimethyl-17-oxo-2,3,4,7,8,9,11,12,14,15-decahydro-1H-cyclopenta[a]phenanthren-3-yl] acetate |
| 32 | 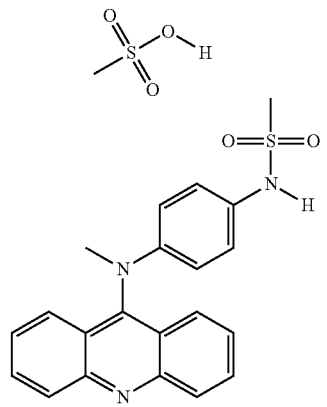 | NSC 156305<br>N-[4-(acridin-9-ylamino)phenyl]-methanesulfonamide; methanesulfonic acid |

TABLE 1-continued

BIOACTIVE SMALL MOLECULES

| Compound | Structure | NSC Number/Nomenclature |
|---|---|---|
| 33 | 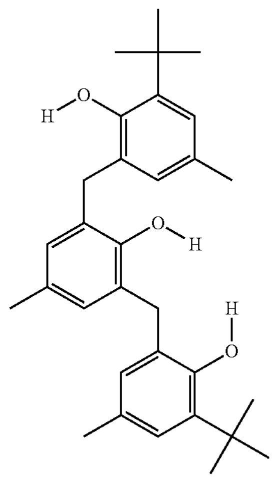 [SMILES: Cc1cc(Cc2cc(C)cc(C(C)(C)C)c2O)c(O)c(Cc2cc(C)cc(C(C)(C)C)c2O)c1] | NSC 62914<br>2-tert-butyl-6-[[3-[(3-tert-butyl-2-hydroxy-5-methylphenyl)methyl]-2-hydroxy-5-methylphenyl]methyl]-4-methylphenol |
| 34 | 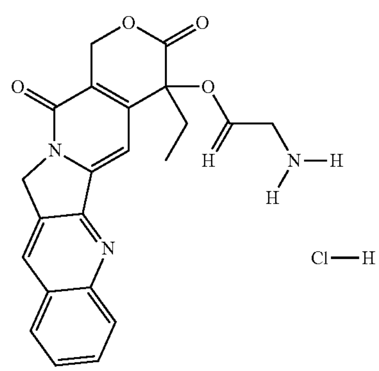 | NSC 606985<br>4-Ethyl-3,14-dioxo-3,4,12,14-tetrahydro-1H-pyrano[3',4':6,7]indolizino[1,2-b]quinolin-4-yl aminoacetate hydrochloride |
| 35 | 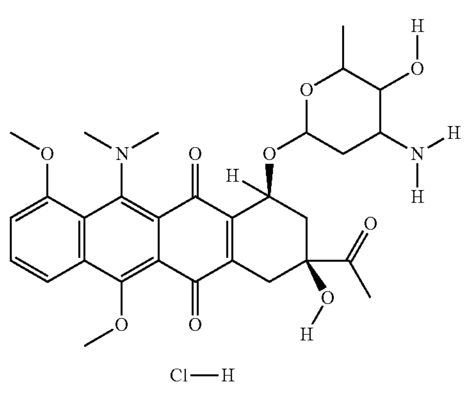 | NSC 254681<br>(1S,3S)-3-acetyl-11-amino-1-(4-amino-5-hydroxy-6-methyloxan-2-yl)oxy-3,6-dihydroxy-10-methoxy-2,4-dihydro-1H-tetracene-5,12-dione hydrochloride |

TABLE 1-continued

BIOACTIVE SMALL MOLECULES

| Compound | Structure | NSC Number/Nomenclature |
|---|---|---|
| 36 | 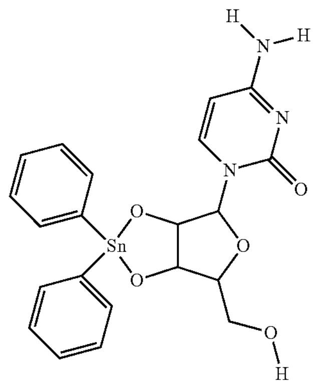 [SMILES: Nc1ccn(C2OC(CO)C3[O][Sn]([c]4ccccc4)([c]4ccccc4)[O]C32)c(=O)n1] | NSC 268665<br>4-amino-1-[6-(hydroxymethyl)-2,2-diphenyl-3a,4,6,6a-tetrahydrofuro[3,4-d][1,3,2]dioxastannol-4-yl]pyrimidin-2-one |
| 37 | 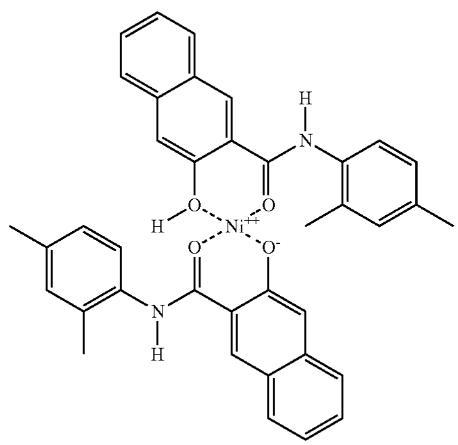 | NSC 306698<br>3-[(2,4-dimethylphenyl)carbamoyl]naphthalen-2-olate; N-(2,4-dimethylphenyl)-3-hydroxynaphthalene-2-carboxamide; nickel(2+) |
| 38 | 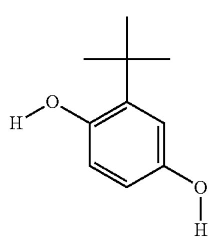 | NSC 4972<br>2-tert-butylbenzene-1,4-diol |
| 39 | 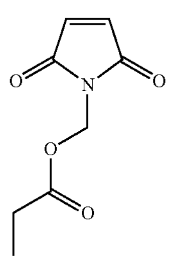 | NSC 19630<br>(2,5-dioxopyrrol-1-yl)methyl propanoate |

TABLE 1-continued

BIOACTIVE SMALL MOLECULES

| Compound | Structure | NSC Number/Nomenclature |
|---|---|---|
| 40 | 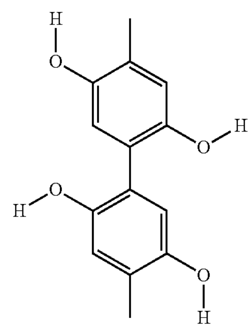 [SMILES: Cc1cc(O)c(-c2cc(O)c(C)cc2O)cc1O] | NSC 2805<br>2-(2,5-dihydroxy-4-methylphenyl)-5-methylbenzene-1,4-diol |
| 41 | 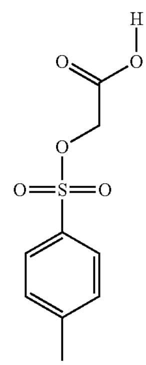 | NSC 16555<br>2-(4-methylphenyl)sulfonyloxyacetic acid |
| 42 | 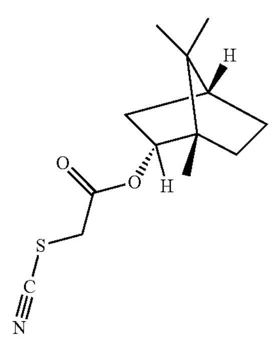 [SMILES: CC1(C)[C@@H]2CC[C@]1(C)[C@H](OC(=O)CSC#N)C2] | NSC 3535<br>[(1S,4R,6R)-1,7,7-trimethyl-6-bicyclo[2.2.1]heptanyl] 2-thiocyanatoacetate |
| 43 | 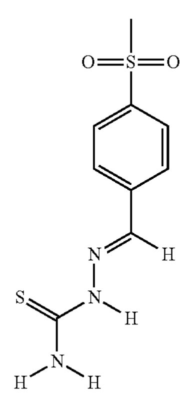 [SMILES: CS(=O)(=O)c1ccc(/C=N/NC(N)=S)cc1] | NSC 27063<br>[(E)-(4-methylsulfonylphenyl)methylideneamino]thiourea |

TABLE 1-continued

BIOACTIVE SMALL MOLECULES

| Compound | Structure | NSC Number/Nomenclature |
|---|---|---|
| 44 | 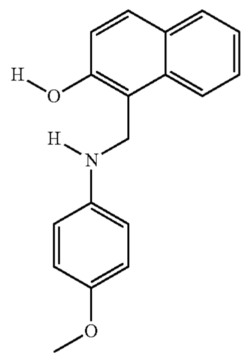 [SMILES: COc1ccc(NCc2c(O)ccc3ccccc23)cc1] | NSC 47924<br>1-[(4-methoxyanilino)methyl]naphthalen-2-ol |
| 45 | 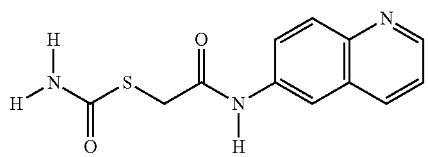 [SMILES: NC(=O)SCC(=O)Nc1ccc2ncccc2c1] | NSC 36738<br>S-[2-oxo-2-(quinolin-6-ylamino)ethyl] carbamothioate |
| 46 | 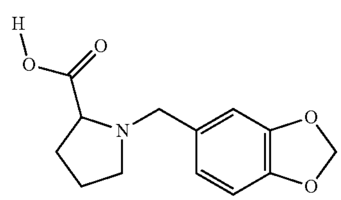 [SMILES: O=C(O)C1CCCN1Cc1ccc2c(c1)OCO2] | NSC 108895<br>1-(1,3-benzodioxol-5-ylmethyl)pyrrolidine-2-carboxylic acid |
| 47 | 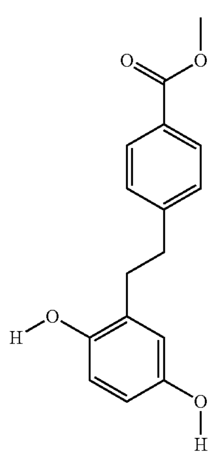 | NSC 681152<br>methyl 4-[2-(2,5-dihydroxyphenyl)ethyl]benzoate |

TABLE 1-continued

BIOACTIVE SMALL MOLECULES

| Compound | Structure | NSC Number/Nomenclature |
|---|---|---|
| 48 | 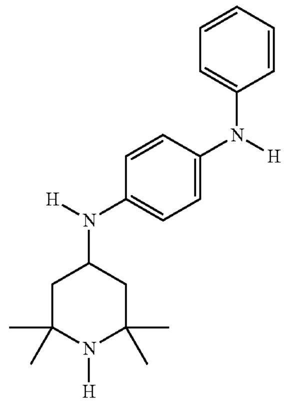 [SMILES: CC1(C)CC(Nc2ccc(Nc3ccccc3)cc2)CC(C)(C)N1] | NSC 632536<br>4-N-phenyl-1-N-(2,2,6,6-tetramethylpiperidin-4-yl)benzene-1,4-diamine |
| 49 | 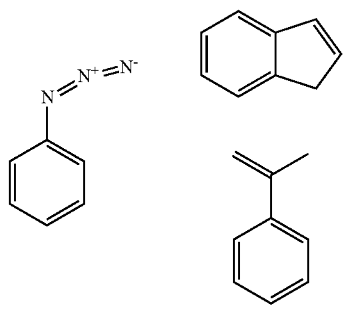 | NSC 122351<br>azidobenzene; 1H-indene; prop-1-en-2-ylbenzene |
| 50 | 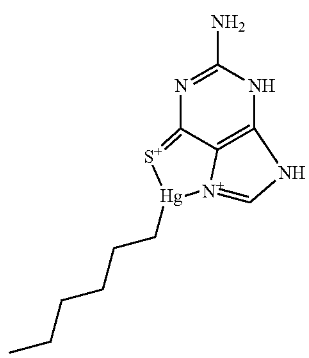 | NSC 268879<br>(2-aminopurin-9-id-6-yl)sulfanyl-hexylmercury |
| 51 | 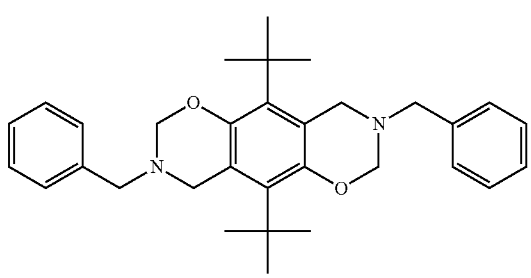 [SMILES: CC(C)(C)c1c2c(c(C(C)(C)C)c3c1OCN(Cc1ccccc1)C3)OCN(Cc1ccccc1)C2] | NSC 48458<br>3,8-dibenzyl-5,10-ditert-butyl-2,4,7,9-tetrahydro-[1,3]oxazino[6,5-g][1,3]benzoxazine |

TABLE 1-continued

BIOACTIVE SMALL MOLECULES

| Compound | Structure | NSC Number/Nomenclature |
|---|---|---|
| 52 | 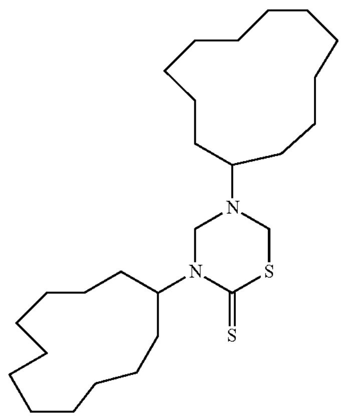 [SMILES: S=C1SCN(C2CCCCCCCCCCC2)CN1C1CCCCCCCCCCC1] | NSC 209910<br>3,5-di(cyclododecyl)-1,3,5-thiadiazinane-2-thione |
| 53 | 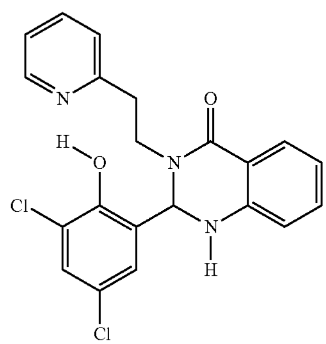 [SMILES: O=C1c2ccccc2NC(c2cc(Cl)cc(Cl)c2O)N1CCc1ccccn1] | NSC 328087<br>2-(3,5-dichloro-2-hydroxyphenyl)-3-(2-pyridin-2-ylethyl)-1,2-dihydroquinazolin-4-one |
| 54 | 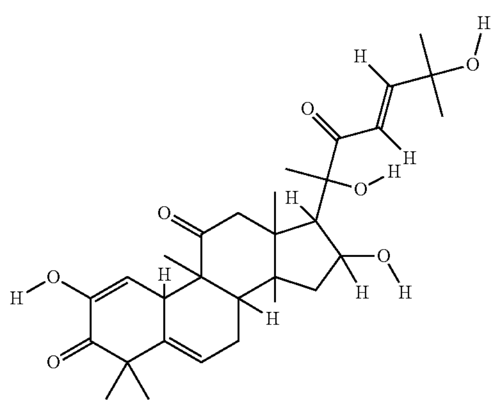 [SMILES: CC(C)(O)/C=C/C(=O)C(C)(O)C1C(O)CC2(C)C3CC=C4C(C=C(O)C(=O)C4(C)C)C3(C)C(=O)CC12C] | NSC 521777<br>17-[(E)-2,6-dihydroxy-6-methyl-3-oxohept-4-en-2-yl]-2,16-dihydroxy-4,4,9,13,14-pentamethyl-8,10,12,15,16,17-hexahydro-7H-cyclopenta[a]phenanthrene-3,11-dione |
| 55 | 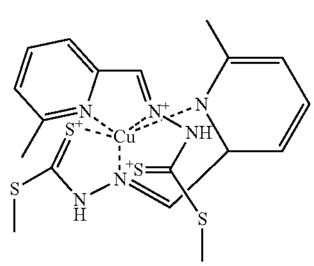 | NSC 310551<br>copper; [(6-methylpyridin-2-yl)methylidene-amino]-[methylsulfanyl(sulfoniumylidene)-methyl]azanide |

TABLE 1-continued

BIOACTIVE SMALL MOLECULES

| Compound | Structure | NSC Number/Nomenclature |
|---|---|---|
| 56 | 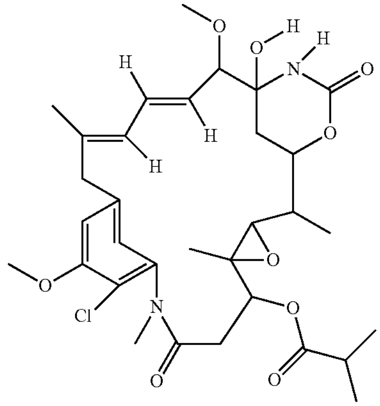 [SMILES: COc1cc2cc(c1Cl)N(C)C(=O)CC(OC(=O)C(C)C)C1(C)OC1C(C)C1CC(O)(NC(=O)O1)C(OC)/C=C/C=C(\C)C2] | NSC 292222<br>Maytansinol isobutyrate or 4,24-Dioxa-9,22-diazatetracyclo[19.3.1.110,14.03,5]hexacosane, maytansine deriv. |
| 57 | 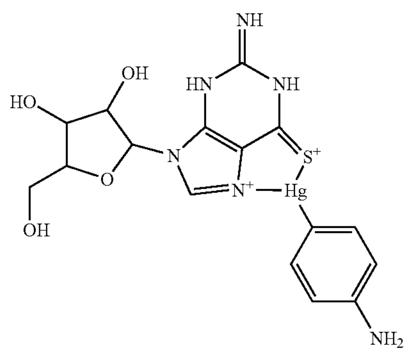 | NSC 321237<br>Mercury, (4-aminophenyl)(6-thioguanosinato-N7,S6)- |
| 58 | 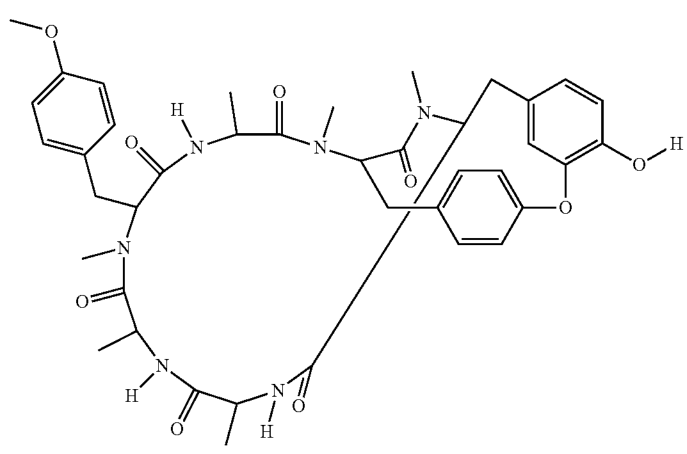 [SMILES: COc1ccc(CC2C(=O)NC(C)C(=O)N(C)C3Cc4ccc(cc4)Oc4cc(ccc4O)CC(C(=O)NC(C)C(=O)NC(C)C(=O)N2C)N(C)C3=O)cc1] | NSC 259969<br>Deoxybouvardin or 24-hydroxy-10-(4-methoxybenzyl)-4,7,9,13,15,29-hexamethyl-22-oxa-3,6,9,12,15,29-hexaazatetracyclo-[14.12.2.2~18,21~.1~23,27~]tritriaconta-18,20,23(31),24,26,32-hexaene-2,5,8,11,14,30-hexone |

TABLE 1-continued

BIOACTIVE SMALL MOLECULES

| Compound | Structure | NSC Number/Nomenclature |
|---|---|---|
| 59 | 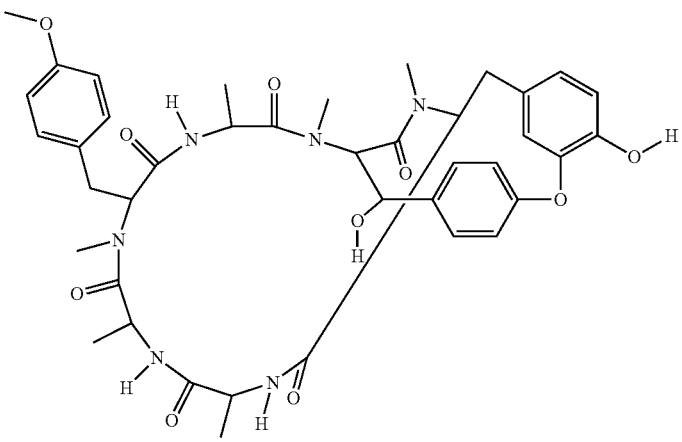 [SMILES: COc1ccc(CC2C(=O)NC(C)C(=O)N(C)C3C(=O)N(C)C(Cc4ccc(O)c(c4)Oc4ccc(cc4)C3O)C(=O)NC(C)C(=O)NC(C)C(=O)N2C)cc1] | NSC 259968<br>Bouvardin or 17,24-dihydroxy-10-(4-methoxybenzyl)-4,7,9,13,15,29-hexamethyl-22-oxa-3,6,9,12,15,29-hexaazatetracyclo-[14.12.2.2~18,21~.1~23,27~]tritriaconta-18,20,23(31),24,26,32-hexaene-2,5,8,11,14,30-hexone |
| 60 | 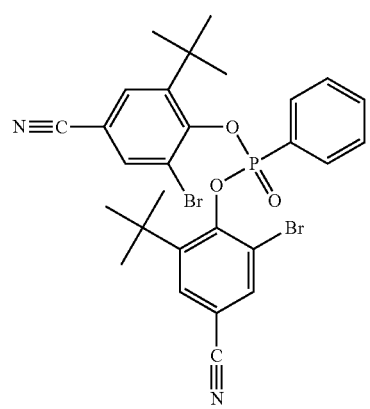 [SMILES: CC(C)(C)c1cc(C#N)cc(Br)c1OP(=O)(Oc1c(Br)cc(C#N)cc1C(C)(C)C)c1ccccc1] | NSC 203328<br>3-bromo-4-[(2-bromo-6-tert-butyl-4-cyanophenoxy)-phenylphosphoryl]oxy-5-tert-butylbenzonitrile |
| 61 | 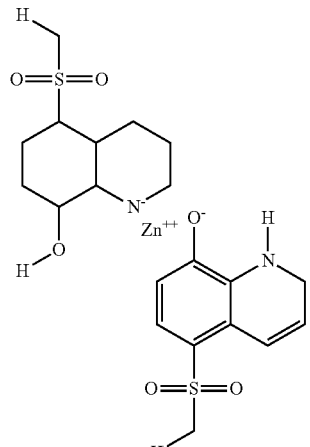 | NSC 166687<br>zinc; 8-hydroxy-3,4,4a,5,6,7,8,8a-octahydro-2H-quinolin-1-ide-5-sulfonic acid; 5-sulfo-1,2-dihydroquinolin-8-olate |

TABLE 1-continued

BIOACTIVE SMALL MOLECULES

| Compound | Structure | NSC Number/Nomenclature |
|---|---|---|
| 62 | 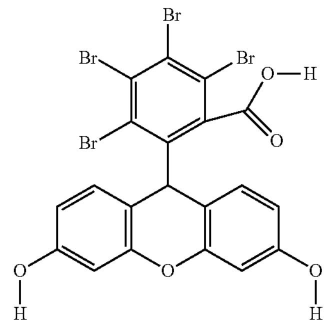 [SMILES: O=C(O)c1c(Br)c(Br)c(Br)c(Br)c1C1c2ccc(O)cc2Oc2cc(O)ccc21] | NSC 119889<br>2,3,4,5-tetrabromo-6-(3,6-dihydroxy-9H-xanthen-9-yl)benzoic acid |
| 63 | 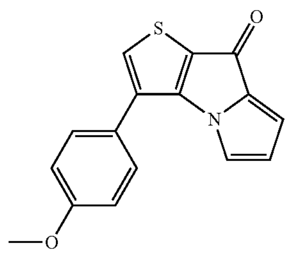 [SMILES: COc1ccc(-c2csc3c2-n2cccc2C3=O)cc1] | NSC 676693<br>3-(4-methoxyphenyl)thieno[2,3-b]pyrrolizin-8-one |
| 64 | 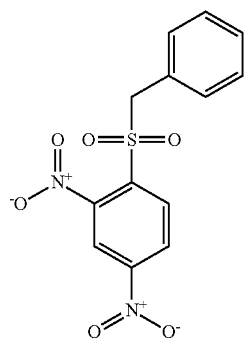 | NSC 122657<br>1-benzylsulfonyl-2,4-dinitrobenzene |
| 65 | 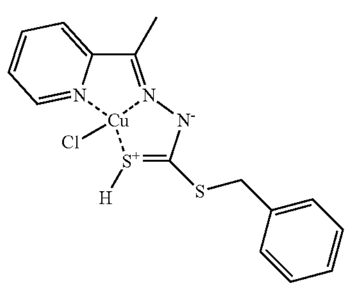 | NSC 295642<br>[benzylsulfanyl(sulfoniumylidene)methyl]-(1-pyridin-2-ylethylideneamino)azanide; chlorocopper |
| 66 | 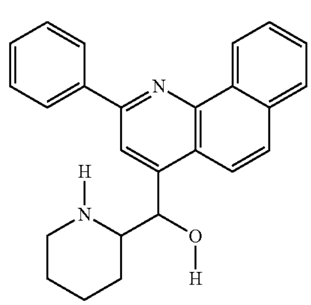 [SMILES: OC(c1cc(-c2ccccc2)nc2c1ccc1ccccc12)C1CCCCN1] | NSC 13480<br>(2-phenylbenzo[h]quinolin-4-yl)-piperidin-2-ylmethanol |

TABLE 1-continued

BIOACTIVE SMALL MOLECULES

| Compound | Structure | NSC Number/Nomenclature |
|---|---|---|
| 67 | 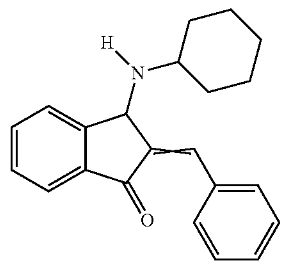 [SMILES: O=C1C(=Cc2ccccc2)C(NC2CCCCC2)c2ccccc21] | NSC 150117<br>2-benzylidene-3-(cyclohexylamino)-3H-inden-1-one chloride |
| 68 | 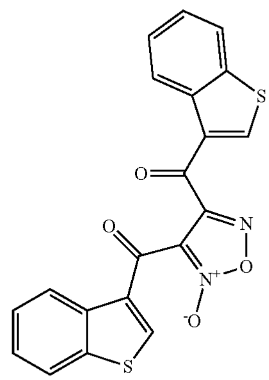 [SMILES: O=C(c1no[n+]([O-])c1C(=O)c1csc2ccccc12)c1csc2ccccc12] | NSC 18877<br>[4-(1-benzothiophene-3-carbonyl)-2-oxide-1,2,5-oxadiazol-2-ium-3-yl]-(1-benzothiophen-3-yl)methanone |
| 69 | 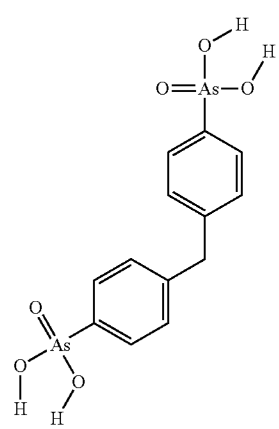 | NSC 48300<br>[4-[(4-arsonophenyl)methyl]phenyl]arsonic acid |
| 70 | 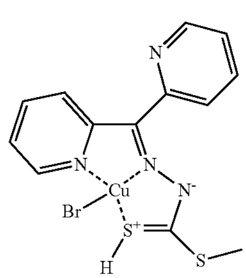 | NSC 321206<br>bromocopper; (dipyridin-2-ylmethylideneamino)-[methylsulfanyl(sulfoniumylidene)methyl]azanide |

TABLE 1-continued

BIOACTIVE SMALL MOLECULES

| Compound | Structure | NSC Number/Nomenclature |
|---|---|---|
| 71 | 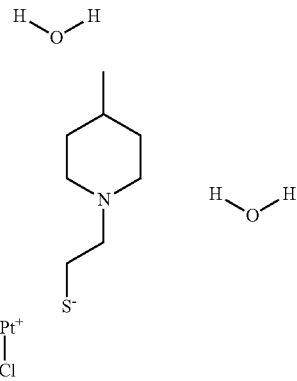 | NSC 292596<br>chloroplatinum(1+); 2-(4-methylpiperidin-1-yl)ethanethiolate; dihydrate |
| 72 | 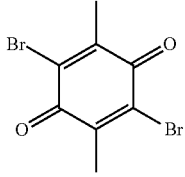 | NSC 112200<br>2,5-dibromo-3,6-dimethylbenzene-1,4-diol; 2,5-dibromo-3,6-dimethylcyclohexa-2,5-diene-1,4-dione |
| 73 | 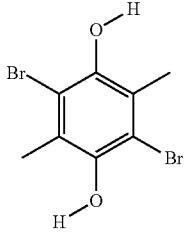 | NSC 274547<br>gold(1+); 1-(2,3,4-triaza-5-azanidacyclopenta-1,3-dien-1-yl)-2,3,4-triaza-5-azanidacyclopenta-1,3-diene; triphenylphosphane |
| 74 | 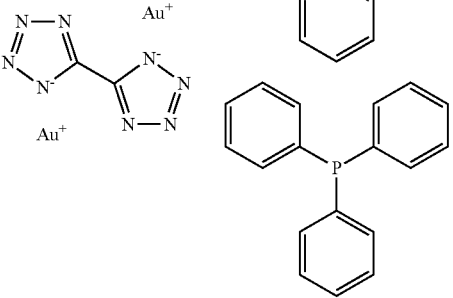 | NSC 4265<br>1,10-phenanthroline hydrochloride |

TABLE 1-continued

BIOACTIVE SMALL MOLECULES

| Compound | Structure | NSC Number/Nomenclature |
|---|---|---|
| 75 | 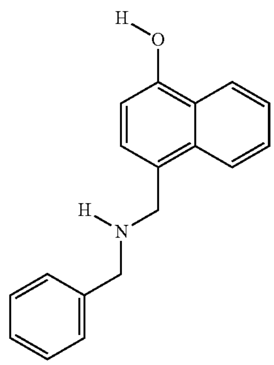 [SMILES: Oc1ccc(CNCc2ccccc2)c2ccccc12] | NSC 130830<br>5-[(benzylamino)methyl]quinolin-8-ol |
| 76 | 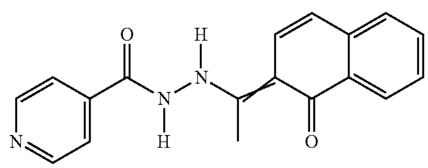 [SMILES: CC(NNC(=O)c1ccncc1)=C1C=Cc2ccccc2C1=O] | NSC 54044<br>N'-[1-(1-oxonaphthalen-2-ylidene)ethyl]pyridine-4-carbohydrazide |
| 77 | 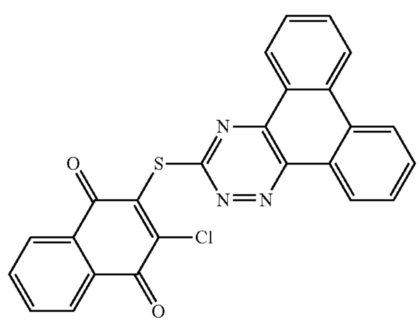 [SMILES: O=C1C(Cl)=C(Sc2nnc3c4ccccc4c4ccccc4c3n2)C(=O)c2ccccc21] | NSC 327705<br>2-chloro-3-phenanthro[9,10-e]-[1,2,4]triazin-3-ylsulfanylnaphthalene-1,4-dione |

V. Potentially Active Related Structures

Additional potentially active compounds can be predicted by comparing the structure of any of Compounds 1-77 to the structures of other known compounds (or newly-derived compounds) and determining the similarity through structure-activity relationship (SAR) or quantitative structure-activity relationship (QSAR) analysis. There are several known methods for SAR and QSAR analysis, including Tanimoto's algorithm (Dogra, "Script for computing Tanimoto coefficient," QSARWorld, available on-line at qsarworld.com/virtual-workshop.php, Jul. 5, 2007) and LeadScope's clustering algorithm (Leadscope Inc., Columbus, Ohio). SAR and QSAR methods compare molecular structures and determine structural features shared by the molecules.

Because Compounds 1-77 (shown in TABLE 1) were derived from a diversity set of small molecules, most of the active compounds are determined not to be structurally related when using Tanimoto's algorithm. However, clustering using LeadScope's algorithm has been used successfully to determine structural similarities between some of the compounds in TABLE 1 and other known compounds. For instance, many compounds in Diversity Set I have family members (which are related by structure) that are not included in Diversity Set I. Such family members and other compounds can be evaluated using LeadScope's algorithm, which searches for (1) large, commonly occurring substructures; (2) substructures that discriminate for a biological response; or (3) substructures that discriminate for membership in a set of compounds (Cross et al., *J. Med. Chem.*, 46:4770-4775, 2003).

Two prediction models were built based on bioactive Compounds 1-77: one for compounds that inhibit endothelial cell growth and another for compounds that inhibit tube formation. The models were built using LeadScope software, and were based on logistic regression. To develop a predictive model for small molecules that inhibit growth of endothelial cells, a total of 70 compounds with known growth inhibitory activity and 76 compounds with no inhibitory effect were used. The predictive model accurately predicted 70/70 positive compounds and accurately predicted 76/77 negative compounds, producing a concordance of 99.3% with 98.6% sensitivity and 100.0% specificity. Concordance is a measure of the overall model accuracy, i.e., 76/77=99.3%. Sensitivity is a measure of how well the model predicts true positives. Sensitivity is calculated using the equation: sensitivity=TP/(TP+FN), where TP is the number of true positives and FN is the number of false negatives. Specificity is a measure of how well the model predicts true negatives. Specificity is calculated using the equation: specificity=TN/(TN+FP), where TN is the number of true negatives and FP is the number of false positives. The concordance for a test set of molecules was 98.0%, with 69 true positives, 1 false positive, 75 true negatives, and 2 false negatives. The sensitivity was 97.2% with 98.7% specificity. Each molecule in the training and test sets was tested in an endothelial cell growth assay to assess the accuracy of the prediction.

A predictive model for small molecules that inhibit tube formation was also developed. Concordance for the training set was 100.0%, with 100.0% sensitivity and specificity. A test set of molecules produced 71.0% concordance, with 12 true positives, 8 false positives, 32 true negatives, and 10 false negatives. The sensitivity was 54.5% with 80.0% specificity. Each molecule in the training and test sets was tested in a tube formation assay to assess the accuracy of the prediction.

These predictive models were applied to various databases, including the NCI small molecule database (dtp.nci.nih.gov/), DrugBank (drugbank.ca), LeadScope (leadscope.com), and PubChem (pubchem.ncbi.nlm.nih.gov/). Based on the models, several hundred small molecules have been predicted to inhibit endothelial cell growth and tube formation. For example, several substructures ("scaffolds") were identified in Compounds 1-77 that are predicted to produce endothelial cell growth inhibition or tube formation inhibition.

The scaffolds were identified using LeadScope software. The software calculates a "z-score" for each compound and activity. The z-score compares the mean activity of a subset to its expected value:

$$z = (\bar{x}_1 - \bar{x}_0)\sqrt{\frac{n_1 n_0}{s_0^2(n_0 - n_1)}}$$

(Cross et al., *J. Med. Chem.*, 46:4770-4775, 2003) After performing clustering analysis, each cluster contains a plurality of small molecules having a common scaffold, each molecule having a z-score value. A low z-score value indicates low values for the defined activity, e.g., growth or tube formation. Thus, a small molecule with a low z-score for growth results in less growth than a molecule with a higher z-score. An average z-score value is associated with the cluster, based on the individual z-score values of the small molecules. A cluster with a low z-score value is likely to contain small molecules with individual low z-score values. In the present embodiments, only scaffolds included in clusters with an average z-score of less than −2 were considered. For example, molecules in clusters having an average growth z-score of less than −2 are predicted to be potential growth inhibitors. These identified scaffolds have predictive value for both growth inhibition and/or tube formation inhibition.

Several representative clusters of molecules having scaffolds predicted to inhibit endothelial cell growth are shown below in TABLES 2-6. Additional molecule clusters having scaffolds predicted to inhibit tube formation are shown in TABLES 7-9.

TABLE 2

CLUSTER 368

Common Scaffold: [structure]

| Compound | Structure | NSC Number/Nomenclature |
|---|---|---|
| 55 | [structure] | NSC 310551 copper; [(6-methylpyridin-2-yl)methylidene-amino]-[methylsulfanyl(sulfoniumylidene)-methyl]azanide |
| 65 | [structure] | NSC 295642 [benzylsulfanyl(sulfoniumylidene)methyl]-(1-pyridin-2-ylethylideneamino)azanide; chlorocopper |
| 70 | [structure] | NSC321206 bromocopper; (dipyridin-2-yl-methylideneamino)-[methylsulfanyl-(sulfoniumylidene)methyl]azanide |

TABLE 3

CLUSTER 71

Common Scaffold: 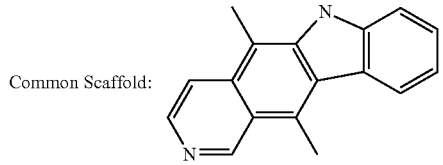 [SMILES: Cc1c2ccncc2c(C)c2c1[nH]c1ccccc12]

| Compound | Structure | NSC Number/Nomenclature |
|---|---|---|
| 30 | 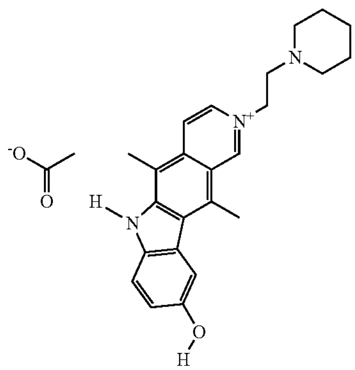 | NSC 311153 5,11-dimethyl-2-(2-piperidin-1-ylethyl)-6H-pyrido[4,3-b]carbazol-2-ium-9-ol acetate |
| 30-A | 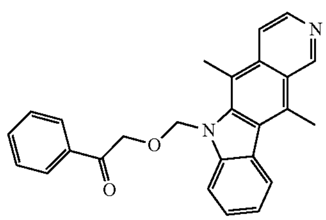 [SMILES: Cc1c2cnccc2c(C)c2c1c1ccccc1n2COCC(=O)c1ccccc1] | NSC 163443 2-(5,11-dimethylpyrido[4,3-b]carbazol-6-yl)ethyl benzoate |
| 30-B | 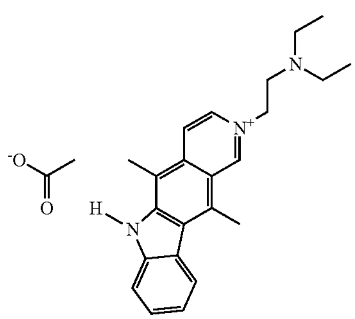 | NSC 359449 2-(5,11-dimethyl-6H-pyrido[4,3-b]carbazol-2-ium-2-yl)-N,N-diethyl-ethanamine acetate |
| 30-C | 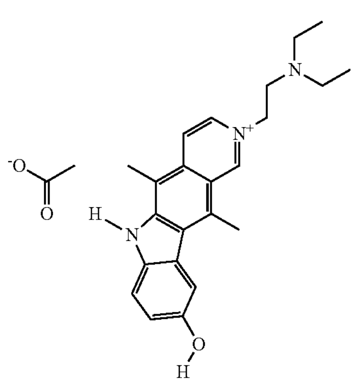 | NSC 311152 2-(2-diethyl-aminoethyl)-5,11-dimethyl-6H-pyrido[4,3-b]carbazol-2-ium-9-ol acetate |

TABLE 3-continued

CLUSTER 71

Common Scaffold: 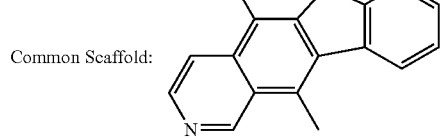

| Compound | Structure | NSC Number/Nomenclature |
|---|---|---|
| 30-D | 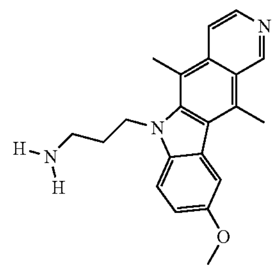 [SMILES: COc1ccc2c(c1)c1c(C)c3cnccc3c(C)c1n2CCCN] | NSC 176327 3-(9-methoxy-5,11-dimethylpyrido[4,3-b]carbazol-6-yl)propan-1-amine (Same NSC # as 26, but not the chloride salt.) |

TABLE 4

CLUSTER 358

Common Scaffold:

| Compound | Structure | NSC Number/Nomenclature |
|---|---|---|
| 34 | 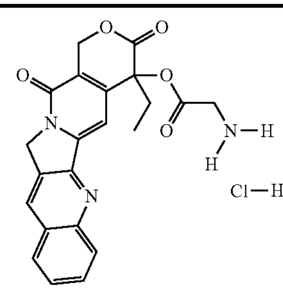 | NSC 606985 4-Ethyl-3,14-dioxo-3,4,12,14-tetrahydro-1H-pyrano[3',4':6,7]indolizino[1,2-b]quinolin-4-yl aminoacetate hydrochloride |
| 34-A | 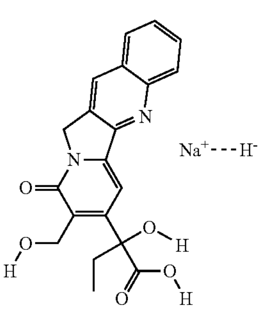 | NSC 100880 sodium; hydride; 2-hydroxy-2-[8-(hydroxy-methyl)-9-oxo-11H-indolizino[1,2-b]quinolin-7-yl]butanoic acid |

TABLE 4-continued

CLUSTER 358

Common Scaffold: 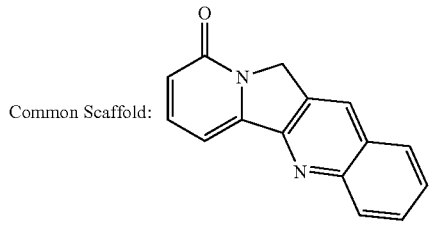 [SMILES: O=c1cccc2n1Cc1cc3ccccc3nc1-2]

| Compound | Structure | NSC Number/Nomenclature |
|---|---|---|
| 34-B | (structure) | NSC 609699 Topotecan, Hycamtin, or 10-((dimethylamino)methyl)-4-ethyl-4,9-dihydroxy-1H-pyrano[3',4':6,7]-indolizino[1,2-b]quinoline-3,14(4H,12H)-dione hydrochloride |
| 34-C | 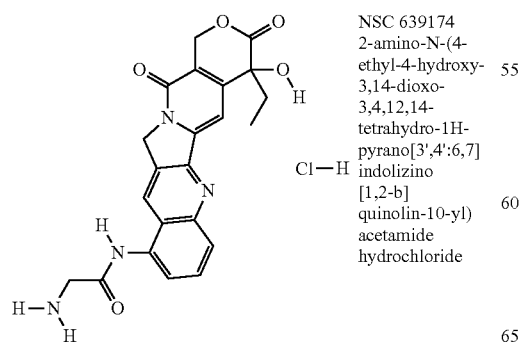 | NSC 639174 2-amino-N-(4-ethyl-4-hydroxy-3,14-dioxo-3,4,12,14-tetrahydro-1H-pyrano[3',4':6,7]indolizino[1,2-b]quinolin-10-yl)acetamide hydrochloride |

TABLE 5

CLUSTER 337

Common Scaffold: 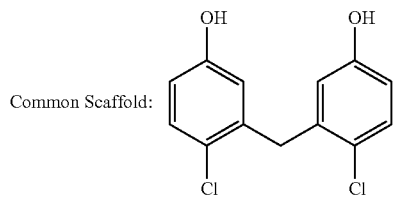 [SMILES: Oc1ccc(Cl)c(Cc2cc(O)ccc2Cl)c1]

| Compound | Structure | NSC Number/Nomenclature |
|---|---|---|
| 17 | (structure) | NSC 5857 6-tert-butyl-2-[(3-tert-butyl-5-chloro-2-hydroxy-6-methylphenyl)methyl]-4-chloro-3-methylphenol |
| 25 | 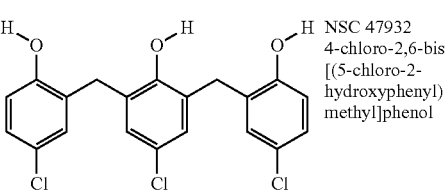 | NSC 47932 4-chloro-2,6-bis[(5-chloro-2-hydroxyphenyl)methyl]phenol |

TABLE 6

CLUSTER 479

Common Scaffold: [4-nitrophenyl benzyl sulfone structure]

| Compound | Structure | NSC Number/Nomenclature |
|---|---|---|
| 64 | [2,4-dinitrophenyl benzyl sulfone structure] | NSC 122657<br>1-benzylsulfonyl-2,4-dinitrobenzene |
| 64-A | [7-benzylsulfonyl-4-nitro-2,1,3-benzoxadiazole structure] | NSC 228148<br>7-benzylsulfonyl-4-nitro-2,1,3-benzoxadiazole |

TABLE 7

Common Scaffold: [purine-Hg-S scaffold structure]

| Compound | Structure | NSC Number/Nomenclature |
|---|---|---|
| 50 | [(2-aminopurin-9-id-6-yl)sulfanyl-hexylmercury structure] | NSC 268879<br>(2-aminopurin-9-id-6-yl)sulfanyl-hexylmercury |
| 57 | [Mercury, (4-aminophenyl)(6-thioguanosinato-N7,S6)- structure] | NSC 321237<br>Mercury, (4-aminophenyl)(6-thioguanosinato-N7, S6)- |

TABLE 8
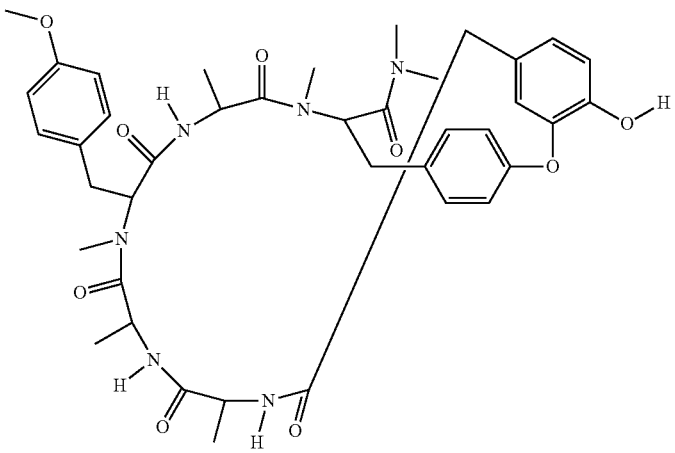 [SMILES: COc1ccc(CC2C(=O)NC(C)C(=O)N(C)C(C(=O)N(C)C)Cc3ccc(cc3)Oc3cc(ccc3O)CC(=O)NC(C)C(=O)NC(C)C(=O)N2C)cc1]
Common Scaffold:
| Compound | Structure | NSC Number/Nomenclature |
|---|---|---|
| 58 | 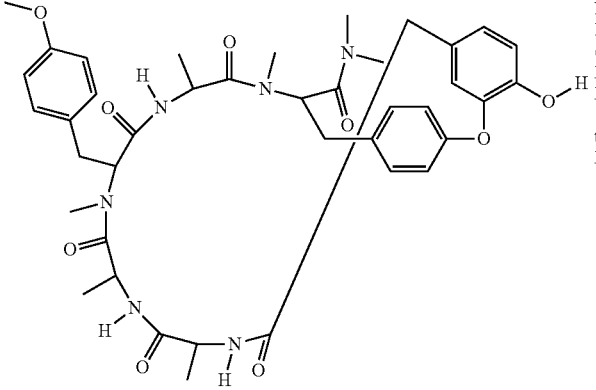 | NSC 259969<br>Deoxybouvardin or 24-hydroxy-10-(4-methoxybenzyl)-4,7,9,13,15,29-hexamethyl-22-oxa-3,6,9,12,15,29-hexaazatetracyclo-[14.12.2.2~18,21~.1~23,27~]tritriaconta-18,20,23(31),24,26,32-hexaene-2,5,8,11,14,30-hexone |
| 59 | 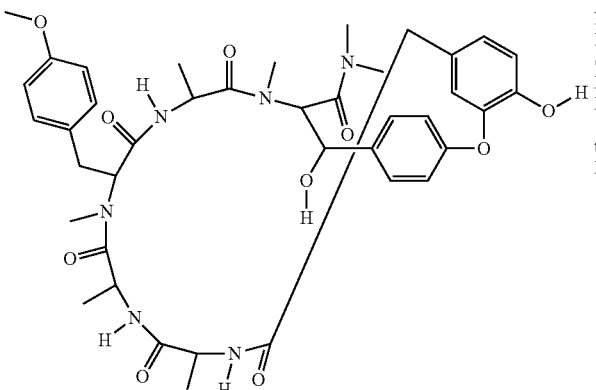 | NSC 259968<br>Bouvardin or 17,24-dihydroxy-10-(4-methoxybenzyl)-4,7,9,13,15,29-hexamethyl-22-oxa-3,6,9,12,15,29-hexaazatetracyclo-[14.12.2.2~18,21~.1~23,27~]tritriaconta-18,20,23(31),24,26,32-hexaene-2,5,8,11,14,30-hexone |

TABLE 9

Common Scaffold: [structure: methylbenzene-1,4-diol]

| Compound | Structure | NSC Number/ Nomenclature |
|---|---|---|
| 38 | [structure] | NSC 4972 2-tert-butylbenzene-1,4-diol |
| 40 | [structure] | NSC 2805 2-(2,5-dihydroxy-4-methylphenyl)-5-methylbenzene-1,4-diol |
| 47 | [structure] | NSC 681152 methyl 4-[2-(2,5-dihydroxyphenyl)ethyl]benzoate |

VI. Bioactivity Tests

Once a new compound has been identified as a potential antiangiogenic compound based on comparison to one of Compounds 1-77, or the compounds additionally listed in any of TABLES 2-9, or any derivative thereof, the identified potential therapeutic compound can be tested for bioactivity. By way of example, any of the methods described herein can be used. The following list provides a description of representative but non-limiting example bioactivity assays. Additional assays will be known to those of ordinary skill; for instance, additional assays are described in U.S. application Ser. No. 12/060,752 (published as US 2009/0088341 on Apr. 2, 2009; incorporated herein by reference in its entirety).

i. Fluorescence-Based Growth Assay

A real time growth assay has been applied to mono- or multiple-cell cultures (co-culture). The fluorescence signal emitted by a culture of the disclosed fluorescent cell-lines is proportional to the number of fluorescent cells present in the culture. In other words, the fluorescence signal, for example measured as the intensity of the emission maxima, from a population of fluorescent cells of one type in a culture will double as the number of fluorescent cells of that type in the culture doubles. Conversely, the fluorescence signal, for example measured as the intensity of the emission maxima, from a population of cells of one type in a culture will be reduced to half if the number of cells of that type in the culture is divided in half. These properties can be used to measure the effect of an exogenous agent, such as one or more additional cell-lines, or a test agent (such as a bioactive SM), on the fluorescent cells in culture. At some point the total fluorescence of a culture may reach signal saturation, such that the signal reaches a plateau as a function of cell number. The effect of an additional cell-line (for example a different cell-line) on a first fluorescent cell-line can be determined (this can be extended to multiple cell-lines and even one or more fluorescent cell-lines, or combinations thereof, for example in a multiplex assay or 3-dimensional co-culture).

The difference between the fluorescence signal (such as the intensity of the fluorescence signal at a particular wavelength, for example the emission maxima of the fluorescence signal) attributable to the fluorescent cell-line of interest grown in co-culture with one or more additional cell-lines relative to a control in some instances will be at least about 10%, meaning that the growth rate of the cell-line of interest is either reduced or increased by at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. The difference may be a statistically significant difference. Thus, the presence of a bioactive SM with or without one or more additional cell-lines can induce a statistically significant difference in the growth rate of a fluorescent cell-line of interest, as compared to the control, such as a value indicative of the basal rate of growth of the fluorescent cell-line, or the fluorescent cell-line of interest grown in the absence of the SM and/or other cells or cell-lines, for example grown in mono-culture. The at least one SM and/or additional cell-line (or additional cell-lines) will in some instances have a negative impact on the first fluorescent cell-line, such that the number of cells of the first fluorescent cell-line is reduced as a function of time relative to a control. In other examples, the at least one SM and/or additional cell-line (or additional cell-lines) will have a positive impact on the first fluorescent cell-line, such that the number of cells of the first fluorescent cell-line present in a cell culture increases as a function of time relative to a control. It is also contemplated that the fluorescent cell-line of interest can be co-cultured with primary cells, such as primary cells obtained from a subject, for example tumor cells, and the effect of the primary cells on the growth rate of the fluorescent cell-line of interest determined. Such co-cultures may be established in 2 or 3 dimensions.

The effect of each fluorescent cell-line on other fluorescent cell-line(s) present in co-culture can be determined, for example in a multiplex assay. For example, using appropriate filters or FACS analysis among other techniques, fluorescent cell-lines expressing different fluorescent proteins, such as red, green, yellow, cyan and the like fluorescent proteins can be discriminated and the fluorescent signal attributable to the different cell-lines determined. Thus, the growth rates of individual fluorescent cell-lines can be determined from a mono-culture and/or a co-culture of two or more fluorescent cell-lines. Such analysis greatly enhances the information that can be obtained about the individual fluorescent cell-lines.

As described herein, in addition to determining the effect of cell-lines on a fluorescent cell-line of interest, the growth assays can be used to determine if an exogenous agent, such as a test agent, for example a chemical agent (for instance a derivative of one of Compounds 1-77, or a structurally related compound), affects the growth of a fluorescent cell-line of interest. This can also be extended to multiple cell-lines (either fluorescent or not grown in co-culture, for example in a multiplex assay). For instance, the growth assay can be used to determine if an exogenous agent, such as a test agent (for example a potential modulator of angiogenesis, such as a potential inhibitor of angiogenesis such as one of Compounds 1-77 or derivatives thereof), growth factor, patient sample, etc. affects the growth rate of a fluorescent cell-line of interest, such as one or more of the fluorescent cell-lines disclosed herein. In addition, the differential effect of the exogenous agent on the different cell-lines can be determined, as can the combinatorial effect of the exogenous agent and the cells on a cell-line of interest.

A fluorescent cell-line of interest can be contacted with an exogenous agent and the impact of the exogenous agent on the growth of the fluorescent cell-line of interest can be determined. For example, a difference between the fluorescence signal of the fluorescent cell-line of interest and a control indicates that the exogenous agent, such as a test agent (for example a potential modulator of angiogenesis, such as a potential inhibitor of angiogenesis), growth factor, patient sample, different cell-line, etc. is a modulator (such as an inhibitor) of angiogenesis. Thus, in several embodiments, one or more of the disclosed fluorescent cell-lines growing in culture are contacted with a test agent (or test agents) to determine if the test agent is a modulator of angiogenesis. Exemplary test agents include compounds that are structurally related to any one of Compounds 1-77 (TABLE 1), structurally related to the scaffolds presented in any one of TABLES 2-9, derivatives or fragments of any of the compounds described herein, and so forth. Following contact with the test agent, the fluorescence of the culture can be measured versus time and/or concentration to determine the impact of the exogenous agent on the one or more fluorescent cell-lines present in the culture. For example, the fluorescence signal generated by a fluorescent cell-line of interest (such as the intensity of the fluorescence signal at a particular wavelength, for example the emission maxima of the fluorescence signal) can be measured to determine if the fluorescence signal attributable to the fluorescent cell-line of interest (such as the intensity of the fluorescence signal at a particular wavelength, for example the emission maxima of the fluorescence signal) is increasing as a function of concentration of the exogenous agent, time, or both, for example by comparison with a control, such as a value indicative of the basal rate of growth of the fluorescent cell-line of interest or the fluorescent cell-line of interest not contacted with the exogenous agent. In several embodiments, the control is a known value indicative of normal growth of the fluorescent cell-line of interest, for example the doubling time of cellular number. In some embodiments, the control is the fluorescence signal of a culture of cells (typically, but not necessarily, a culture of the fluorescent cell-line of interest) not contacted with the exogenous agent.

In some embodiments, an exogenous agent, such as a test agent, decreases the growth rate of the fluorescent cell-line of interest. A test agent exhibiting such an activity is identified as a potential inhibitor of angiogenesis (that is, having antiangiogenic activity) and would be of use in treating a disease or condition in which normal angiogenesis is increased, for example cancer. In some embodiments, a decrease in the growth rate of the fluorescent cell-line of interest relative to a control is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease. Because the fluorescence signal attributable to a fluorescent cell-line of interest is proportional to the number of cells of the cell-line of interest present, the percentage decrease can be measured as a percentage decrease in the fluorescence signal, for example the fluorescence intensity at a particular wavelength, such as the emission maxima, attributable to the cell-line of interest. In additional embodiments, the decrease is a statistically significant decrease as compared to a control.

ii. Fluorescence-Based Tubule Formation Assay

Cultures of fluorescent cell-lines expressing different fluorescent proteins, such as the fluorescent cell-lines disclosed herein and in U.S. application Ser. No. 12/060,752 (published as US 2009/0088341 on Apr. 2, 2009; incorporated herein by reference in its entirety) can be applied to tubule formation assays. Formation of new blood vessels is fundamental to angiogenesis and is the focus of many drug screening and cell signaling studies. Blood vessel development is a significant event in the development and growth of solid tumors, and is involved in wound healing, retinopathy and macular degeneration. Fluorescent cell-lines, and in particular the disclosed endothelial fluorescent cell-lines, are ideal for use in assays for assessing the degree of blood vessel formation using in vitro cell culture assays (see for example Auerbach et al. *Clinical Chemistry* 49:1, 32-40, 2003; Taraboletti and Giavazzi, *EJC* 40, 881-889, 2004). Because no fluorescent/colorimetric staining is needed, the tubule formation assay can be followed over time and can be directly visualized used in existing instrumentation, such as the BD Pathway™ Bioimager (BD Bioscience, San Jose, Calif.). This allows for the study of the interaction between different cells types, or between a SM(s) of interest and/or one or more cell types, in this angiogenesis in vitro assay. In addition, the effects of SMs on tubule formation potential can also be determined for a co-culture of a fluorescent cell-line of interest with primary cells, such as primary cells obtained from a subject, for example tumor cells. Such co-cultures can be established as 2-dimensional or 3-dimensional co-cultures, such as those described in U.S. patent application Ser. No. 12/802,666.

Tubule formation assays are typically based on the ability of endothelial cells, such as fluorescent endothelial cells (stably-transfected to express a fluorescent protein), to form distinct blood-vessel-like tubules in an extracellular matrix (such as BD Matrigel™ Matrix available from BD Bioscience, BME available from Trevigen, or GELTREX™ available from Invitrogen®, and the like). The cells are visualized by microscopy, such as fluorescence microscopy in the case of fluorescent cells, and the ability of one or more compounds of interest to affect the ability of a fluorescent cell-line of interest to form tubules (also called the tubule formation potential) is determined. The determination of tubule formation can be performed by manual tracing or by automated confocal imaging system, for example using a BD Pathway™ Bioimager in conjunction with AngioApplication™. Using fluorescent cell-lines, tubule formation assays can be performed on live cells, for example to avoid artifacts that may arise from fixation of cells, such as the disruption of tubules. Several parameters can be measured in tubule formation assays, such as the total area of the tubules, the total number of tubules, number of nodes, number of branch points, the number of tubes per node, and/or node area. In some embodiments, the tubule formation potential is determined by a computer implemented method, for example using the program AngioApplication™.

Fluorescent cell-lines can be used to determine the effects of an exogenous agent, such as cell-lines and test agents, on tubule formation. In particular examples, a test agent is one or more compounds that are structurally related to any one of Compounds 1-77 (TABLE 1), structurally related to the scaffolds presented in any one of TABLES 2-9, derivatives or fragments of any of the compounds described herein, and so forth. In some embodiments, multiple fluorescent cell-lines are grown in co-culture. Thus, the effect of each fluorescent cell-line on the other fluorescent cell-line(s) present can be determined, or the differential effect of an exogenous agent, such as a test agent, or patient sample, on the different cell-lines can be assessed in a multiplex assay. For example using appropriate filters, the fluorescent signal from fluorescent cell-lines expressing different fluorescent proteins, such as red, green, yellow, cyan fluorescent proteins can be discriminated and the fluorescent signal attributable from the different fluorescent cell-lines determined. Thus, the tubule formation potential of individual cell-lines can be determined from a mono-culture or even a co-culture, for example a co-culture of more than one fluorescent cell-line.

When grown in co-culture, a difference between the tubule formation potential of the fluorescent cell-line of interest from a control, such a mono-culture of the fluorescent cell-line of interest indicates that the other cell-line(s) is a modulator of angiogenesis, as evidenced by the difference in tubule formation potential. In some embodiments, the difference between the tubule formation potential, for example as measured by the number of least one of the total area of the tubules, the total number of tubules, number of nodes, number of branch points, the number of tubes per node, or node area formed in the co-culture of the fluorescent cell-line of interest relative to a control is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, the difference is a statistically significant difference. Thus, a cell-line can induce a statistically significant difference in the tubule formation potential of a fluorescent cell-line of interest, such as one of the disclosed fluorescent cell-lines. Taking a combinatorial approach the impact of multiple different cell-lines either alone or in combination on the tubule formation potential of the fluorescent cell-line of interest can be determined. In some examples, the presence of one or more additional cell-lines decreases the tubule formation potential of the fluorescent cell-line of interest, for example as measured by the total area of the tubules, the total number of tubules, number of nodes, number of branch points, the number of tubes per node, or node area formed by the fluorescent cell-line of interest. These cell-lines would be identified as negative regulators of angiogenesis.

Utilizing fluorescent cell-lines, tubule formation assays can also be used to screen for a biological effect of a test agent, such as the effect of potential modulators of angiogenesis, for example compounds that are structurally related to any one of Compounds 1-77 (TABLE 1), structurally related to the scaffolds presented in any one of TABLES 2-9, derivatives or fragments of any of the compounds described herein, and so forth. In some embodiments, a fluorescent cell-line of interest (or multiple cell-lines of interest in a multiplex assay) is contacted with an exogenous agent, such as a cell-line or test agent, and the impact of the exogenous agent on tubule formation potential can be determined. Exemplary test agents are provided herein. For example using the difference between the total area of the tubules, the total number of tubules, number of nodes, number of branch points, the number of tubes per node, and/or node area between a fluorescent cell-line of interest and a control are used to determine if an exogenous agent, such as a test agent, impacts the ability of a fluorescent cell-line of interest to form tubules. A difference between the tubule formation potential of a fluorescent cell-line of interest contacted with an exogenous agent and a control (such as a control culture exposed to the exogenous agent) indicates that the exogenous agent is a modulator of angiogenesis. In some embodiments, the difference between the tubule formation potential of the fluorescent cell-line contacted with an exogenous agent relative to a control is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, the difference is a statistically significant difference. Thus, an exogenous agent can induce a statistically significant difference in the tubule formation potential of the fluorescent cell-line of interest contacted with the test agent, as compared to the control, such as the fluorescent cell-line of interest not contacted with the exogenous agent.

In one embodiment, the exogenous agent decreases the ability of a fluorescent cell-line of interest to form tubules. A test agent exhibiting such an activity is identified as a potential inhibitor of angiogenesis and would be of use in treating a disease or condition in which normal angiogenesis is increased, for example cancer. Such agents could be used alone, or in combination with other agents (such as, but not limited to a SM, peptide or antibody) known to inhibit angiogenesis by a similar or complementary mechanism (such as at a different step in the angiogenesis pathway). In some embodiments, a decrease in the tubule formation potential of the fluorescent cell-line of interest is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease as compared to control. In additional embodiments, the decrease is a statistically significant decrease as compared to a control.

iii. Fluorescence-Based Migration Assay

Another assay that can be used is a cellular migration assay. These assays assess cellular migration in a controlled environment, such as a differential migration of the cell-line, (or multiple cell-lines in a multiplex assay) as determined by fluorescent signals (such as the intensity of a fluorescent signal of a particular color, or at a particular wavelength, such as the emission maxima of a particular fluorescent protein) in a location that is associated with migration to a particular location.

A cellular migration assay can be used to determine the ability of cells to migrate up or down a chemical gradient. Migration "up" a chemical gradient refers to migration from a region of lower chemical concentration of a chemical to a region of higher chemical concentration (for example migration toward a higher concentration of a chemical attractant or away from a lower concentration of the chemical attractant), while migration "down" a chemical gradient refers to migration from a region of higher chemical concentration to a region of lower chemical concentration (for example migration away from a higher concentration of a chemical repellent toward a lower concentration of the chemical repellent). Such migration is typically referred to as chemotaxis. Cells, such as fluorescent cell-lines, respond to chemical signals in their environment by the stimulation of concerted movement either toward a chemical attractant or away from a chemical repellent. In mammalian cells, such as fluorescent cell-lines, typical chemo-attractants include factors excreted by cells, for example factors found in serum, such as growth factors and the like.

Fluorescent cells (such as those described in U.S. application Ser. No. 12/060,752 (published as US 2009/0088341 on Apr. 2, 2009)) can be used in any cell migration assay format, such as the ChemoTx™ system (NeuroProbe, Rockville, Md.), transwell system or any other suitable device or system. In some examples, a cell migration assay is carried out as follows: A culture of a fluorescent cell-line of interest is placed into a first chamber of a cell migration apparatus, and an exogenous agent (such as a chemoattractant) is placed in a second chamber that is adjacent to and in communication with the first chamber of the cell migration apparatus, so that cellular migration from the first chamber to the second chamber can be detected. The chambers may be separated by a membrane or filter that permits passage of cells from one chamber to the other chamber. The membrane or filter is configured such that the passive diffusion of the cells across the membrane or filter is minimized. In one example, the first chamber is the upper chamber of the apparatus and the second chamber is the lower chamber of the apparatus. In some examples the upper chamber is omitted and the cells are placed directly on a membrane or filter in communication with the lower chamber. The ability of a fluorescent cell-line such as the fluorescent cell-lines used in the assays described herein to be stimulated to migrate can be determined. Typical migration assays have "unknown" sites (with cell suspension above the filter and a solution containing the chemotactic factor below it) and "negative control" sites (with cell suspension above the filter and suspension media, but no chemotactic factor, below). Random migration of unstimulated cells will account for some of the cells that pass through the filter. Migrated cells at the negative control sites show the extent of unstimulated random migration, which can then be differentiated from chemotactic migration, or chemotaxis. Cells that stably express a fluorescent protein, such as the disclosed fluorescent cells can be read in a microplate with a fluorescence microplate reader. Thus, the number of fluorescent cells present in either the upper chamber, lower chamber, or both chambers can be determined, for example as a function of time.

Migration assays can be used to determine if an exogenous agent, such as a test agent, affects or differentially affects the migration of one or more of the fluorescent cell-line of interest. A fluorescent cell-line of interest can be contacted with exogenous agent and the impact of the exogenous agent on the migration of the fluorescent cell-line of interest can be determined. For example, a difference between the number of cells that migrate between a fluorescent cell-line of interest contacted with an exogenous agent and a control indicates that the exogenous agent, such as a test agent, cell-line, growth factor, etc., is a modulator of cellular migration. In other embodiments, differences in migration among different cell-lines in the migration assay provide an indication of differential migration of the different cell-lines in response to the exogenous agent. In some embodiments, the difference between the number of cells that migrate of the fluorescent cell-line contacted with an exogenous agent relative to a control, (for example as measured by the fluorescence intensity of a fluorescent protein stably and constitutively expressed by the cells) is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, the difference is a statistically significant difference. Thus, an exogenous agent can induce a statistically significant difference in the migration of a fluorescent cell-line of interest contacted with the exogenous agent, as compared to the control, such as the fluorescent cell-line of interest not contacted with the exogenous agent or a different cell-line that has been mixed with the cell-line of interest.

In one embodiment, the exogenous agent, such as a test agent, decreases the ability of a fluorescent cell-line of interest to migrate. A test agent with such an activity is identified as a potential inhibitor of angiogenesis and would be of use in treating a disease or condition in which normal angiogenesis is increased, for example cancer. In some embodiments, a decrease in migration of the fluorescent cell-line of interest is at least about a 30%, at least about a 40%, at least about a 50%, at least about a 60%, at least about a 70%, at least about a 80%, at least about a 90%, at least about a 100%, at least about a 150%, at least about a 200%, at least about a 250%, at least about a 300%, at least about a 350%, at least about a 400%, at least about a 500% decrease as compared to control. In additional embodiments, the decrease is a statistically significant decrease as compared to a control.

iv. Fluorescence-Based Cell Viability Assay

Another example of an assay is a cell viability assay. Such assays are based on the release of fluorescent protein from the cytoplasm of fluorescent cell-lines that constitutively express fluorescent protein that occurs when the integrity of the cell membrane of the cells is compromised, for example when the cell dies, such as when the cell is exposed to a cytotoxic agent, such as a test agent that is cytotoxic to the cell. Upon exposure to a cytotoxic agent the fluorescent protein is liberated to the culture media and it can be measured, for example using a fluorimeter. The greater the amount of fluorescent protein liberated from the cells present in the culture, the greater the intensity of the fluorescence present in the media. The measured fluorescence in the media corresponds to number of dead cells.

In some embodiments, the cell viability assay is used to determine if an exogenous agent, such as a test agent, is cytotoxic to one or more of the fluorescent cell-lines of interest, such as one or more of the fluorescent cell-lines disclosed herein. A fluorescent cell-line of interest can be contacted with exogenous agent and the impact of the exogenous agent on the death of the fluorescent cell-line of interest can be determined. For example, an increase in the relative florescence present in the media of between a fluorescent cell-line of interest contacted with an exogenous agent and a control indicates that the exogenous agent, such as a test agent, cell-line, growth factor, etc., is cytotoxic to the cell-line of interest. In other embodiments, differential cytotoxicity of an exogenous agent to different cell-lines in the cell viability assay provides an indication that a specific exogenous agent is preferentially cytotoxic to one cell-line but not other cell-lines present in the culture. Such information is useful for screening agents that are preferentially or differentially cytotoxic to a specific cell-type, for example to the exclusion of other cell types. For example, in a mixed cell population a test agent could be screened to determine if it was cytotoxic (for example differentially cytotoxic) to diseased cells (such as tumor cells) present in the mixed cell population, but not normal cells present in the mixed cell population.

In some embodiments, the difference between the fluorescence of the media of a fluorescent cell-line contacted with an exogenous agent relative to a control, (for example as measured by the fluorescence intensity of a fluorescent protein liberated from the cell-line into the media) is at least about 10%, such as at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%. In some embodiments, the difference is a statistically significant difference. Thus, an exogenous agent, such as a test agent, can induce a statistically significant difference in the number of cells that die as a the migration of a fluorescent cell-line of interest contacted with the exogenous agent, as compared to the control, such as the fluorescent cell-line of interest not contacted with the exogenous agent or a different cell-line that has been mixed with the cell-line of interest.

v. Additional Angiogenesis Assays

The following descriptions provide additional examples of angiogenic assays, which may be useful in measurements of the angiogenic (or antiangiogenic) activity of a test compound, such as a compound structurally related to one of Compounds 1-77 (TABLE 1), or a scaffold shown in any of TABLES 2-9, and derivatives thereof. In particular examples, these assays can also be used to measure the antiangiogenic activity of combinations of at least two SMs from Compounds 1-77 or combinations of at least one SM from Compounds 1-77 and an additional known or potential angiogenesis inhibitor. One of ordinary skill in the art will recognize that other angiogenic assays also can be used.

Corneal Pocket Assay:

This is the "gold standard" method for following the effect of defined substances to promote neovascularization of the normally avascular cornea. This assay has the advantage that new blood vessels are easily detected and essentially must be newly formed blood vessels in the normally avascular cornea. Agents to be tested for angiogenic or anti-angiogenic activity are immobilized in a slow release form in an inert hydron pellet of approximately 1-2 µl volume. That pellet is implanted into the corneal epithelium of an anesthetized C57BL mouse (or a rabbit) in a pocket created by microdissection. Over a five to seven day period angiogenic factors stimulate the ingrowth of vessels from the adjacent vascularized corneal limbus. A photographic record is created by slit lamp photography. The appearance, density and extent of these vessels are evaluated and scored. In some cases, the time course of the progression is followed in anesthetized animals, prior to sacrifice. Vessels are evaluated for length, density and the radial surface of the limbus from which they emanate (expressed as clock-faced hours).

Intradermal Sponge Angiogenesis Assay:

Inert biopolymer sponges impregnated with defined amounts of test reagents are implanted subcutaneously through a transdermal incision, into a pocket created in the subcutaneous tissue. Sponges are then removed following a defined periods ranging from five to fifteen days and the new vessel formation quantitated by a number of biochemical and histomorphometric parameters. Portions of a sponge can be extracted and analyzed by Western blot for endothelial restricted gene product such as VE cadherin, FLK-1 receptors, and others. Frozen section portions of that same sample are evaluated by immunohistochemistry for similar antigens to confirm that expression levels reflect endothelial cell proteins contained within new vessels that have invaded the sponge. In conjunction with the mouse corneal pocket assay, systemic administration of putative angiogenesis inhibitors by intraperitoneal or intravenous routes permits evaluation and comparison of the local effects of those inhibitors on angiogenic stimuli in different microvascular beds.

Chick Chorioallantoic Membrane (CAM) Assay:

Another assay involves the use of chicken chorioallantoic membrane (the CAM assay; see Wilting et al., *Anat. Embryol.* 183: 259, 1991). The CAM assay permits the quantitation of angiogenesis and anti-angiogenesis in the chick embryo chorioallantoic membrane (CAM). Briefly, chicken eggs are windowed on day two or three of incubation and the windows are sealed with tape, wax, glass slides, or PARAFILM® wrapper. On day eight of incubation, the windows are opened, and small sponges or pieces of gelatin are placed on top of the growing CAM.

After implantation, the sponges are treated with at least one stimulator or inhibitor (for example, any of Compounds 1-77) of blood vessel formation. Blood vessels growing vertically into the sponge and at the boundary between sponge and surrounding CAM mesenchyme are counted by a morphometric method on day twelve. Factors that increase the number of blood vessels growing into the sponge are considered angiogenic, whereas factors that inhibit blood vessel growth into the sponge are considered antiangiogenic. Quantification of the number of new vessels yields a measure of angiogenicity. Thus, this technique facilitates the characterization of agonists or antagonists of angiogenesis. (For more information, see Ribatti et al., *J. Vasc. Res.* 1997, 34:455-463).

Directed In Vivo Angiogenesis Assay (DIVAA):

Yet another angiogenesis assay is termed a Directed in vivo Angiogenesis Assay (DIVAA; Guedez et al., *American Journal of Pathology* 162(5):1431-9, 2003). Silicone tubes (0.15 mm outside diameter, New Age Industries, Southampton, Pa.) are cut to 1 cm in length, and one end of each tube is closed with liquid silicone and dried for 24 hours, then autoclaved. A dilution of test substances is prepared in matrigel in sterile cold Eppendorf tubes. Tubes are filled with a Hamilton syringe. Nude mice are anesthetized, and a pocket is made in the dorsal skin of each animal. The tubes are then implanted with the open end first and the wounds are sealed.

After nine to eleven days, the tail veins are injected with FITC-dextran to visualize the blood vessels, and the dye is allowed to distribute throughout the vasculature for about 20 minutes. Mice are then euthanized with $CO_2$ and the skin pockets are removed.

Skin is then dissected, keeping the vessels near the mouth of the tube. The matrigel is then displaced from the tube, incubated at 37° C. in the presence of dispase, then vortexed, centrifuged, and matrigel aliquots are transferred into 96-well plates for fluorescent emission. Fluorescence is read in a fluorimeter.

VII. Pharmaceutical Compositions and Modes of Administration

The compounds described herein (such as Compounds 1-77), and derivatives thereof, are particularly useful for inhibiting or reducing angiogenesis in a subject, such as a subject suffering from a disease or condition accompanied by deregulated angiogenesis. The methods of inhibiting or reducing angiogenesis include administering to a subject a therapeutically effective amount of at least one agent identified as one that inhibits or reduces angiogenesis (e.g., any of Compounds 1-77, as described herein). Thus in some embodiments, the pharmaceutical composition containing a bioactive compound that decreases angiogenesis is administered to a subject, such as a subject with cancer or another disease or condition which would be treated by reducing angiogenesis. In some embodiments, the subject is a human subject. It is also contemplated that the pharmaceutical compositions containing at least one bioactive compound that decreases angiogenesis can be administered with known conventional treatments, for instance treatments for cancer, such as in conjunction with a therapeutically effective amount chemotherapeutic agent.

In particular embodiments, the pharmaceutical composition comprises at least one of 2-benzylidene-3-(cyclohexylamino)-3H-inden-1-one chloride (NSC 150117), deoxybouvardin (NSC 259969), (2,5-dioxopyrrol-1-yl)methyl propanoate (NSC 19630), 1-benzylsulfonyl-2,4-dinitrobenzene (NSC 122657), maytansinol isobutyrate (NSC 292222), chloroplatinum(1+); 2-(4-methylpiperidin-1-yl)ethanethiolate; dehydrate (NSC 292596), or a pharmaceutically acceptable salt thereof. The composition can also comprise any combination of two, three, four, five, or six of these compounds. In other particular embodiments, any of the described compositions further comprise [4-[(4-arsonophenyl)methyl]phenyl]arsonic acid (NSC 48300), or a pharmaceutically-acceptable salt thereof. The combinations of the compounds can be determined based in part on the differential effect of each of the SMs in the combination on expression of angiogenesis genes, as described in greater detail in Example 5.

Therapeutic compound(s) can be administered directly to a subject for example a human subject. Administration is by any of the routes normally used for introducing a compound into ultimate contact with the tissue to be treated. The compounds are administered in any suitable manner, optionally with pharmaceutically acceptable carrier(s). Suitable methods of administering therapeutic compounds are available and well known to those of skill in the art, and although more than one route can be used to administer a particular composition, a particular route can often provide a more immediate and more effective reaction than another route.

When the antiangiogenic compound is to be used as a pharmaceutical, it is placed in a form suitable for therapeutic administration. The test agent (antiangiogenic compound) may, for example, be included in a pharmaceutically acceptable carrier such as excipients and additives or auxiliaries, and administered to a subject. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, nontoxic excipients, including salts, preservatives, buffers and the like, as described, for instance, in *Remington's Pharmaceutical Sciences,* 15th ed., Easton: Mack Publishing Co., 1405-1412, 1461-1487, 1975, and The National Formulary XIV, 14th ed., Washington: American Pharmaceutical Association, 1975). The pH and exact concentration of the various components of the pharmaceutical composition are adjusted according to routine skills in the art. See *Goodman and Gilman The Pharmacological Basis for Therapeutics,* 7th ed.

The pharmaceutical compositions are in general administered topically, intravenously, orally or parenterally or as implants. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampoule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science,* 249:1527-1533, 1990, which is incorporated herein by reference.

For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units, and also by multiple administrations of subdivided doses at specific intervals.

A therapeutically effective dose is the quantity of a compound according to the disclosure necessary to prevent, to cure or at least partially ameliorate the symptoms of a disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al., eds., *Goodman and Gilman: the Pharmacological Bases of Therapeutics,* 8th ed., Pergamon Press, 1990; and *Remington's Pharmaceutical Sciences,* 17th ed., Mack Publishing Co., Easton, Pa., 1990. Effectiveness of the dosage can be monitored by any method.

The antiangiogenic compounds described herein may be formulated in a variety of ways depending on the location and type of disease to be treated or prevented. Pharmaceutical compositions are thus provided for both local use at or near an affected area and for systemic use (in which the agent is administered in a manner that is widely disseminated via the cardiovascular system). This disclosure includes within its scope pharmaceutical compositions including at least one antiangiogenic compound, formulated for use in human or veterinary medicine.

Pharmaceutical compositions that include at least one antiangiogenic compound as described herein as an active ingredient, or that include both an antiangiogenic compound and an additional anti-angiogenic agent, may be formulated with an appropriate solid or liquid carrier, depending upon the particular mode of administration chosen. Additional active ingredients include, for example, anti-angiogenic agents, such as inhibitors of bFGF or VEGF.

A suitable administration format may best be determined by a medical practitioner for each subject individually. Various pharmaceutically acceptable carriers and their formulation are described in standard formulation treatises, for example, *Remington's Pharmaceutical Sciences* by E. W. Martin. See also Wang and Hanson, *J. Parenteral Sci. Technol.,* Technical Report No. 10, Supp. 42: 2S, 1988.

The dosage form of the pharmaceutical composition will be determined by the mode of administration chosen. For instance, in addition to injectable fluids, inhalational, topical, ophthalmic, peritoneal, and oral formulations can be employed. Inhalational preparations can include aerosols, particulates, and the like. In general, the goal for particle size for inhalation is about 1 µm or less in order that the pharmaceutical reach the alveolar region of the lung for absorption. Oral formulations may be liquid (for example, syrups, solutions, or suspensions), or solid (for example, powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intra-articular injection or infusion, or by sublingual, oral, topical, intra-nasal, ophthalmic, or transmucosal administration, or by pulmonary inhalation. When antiangiogenic compounds are provided as parenteral compositions, for example, for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Antiangiogenic compounds are also suitably administered by sustained-release systems. Suitable examples of sustained-release formulations include suitable polymeric materials (such as, for example, semi-permeable polymer matrices in the form of shaped articles, for example, films, or mirocapsules), suitable hydrophobic materials (for example as an emulsion in an acceptable oil) or ion exchange resins, and sparingly soluble derivatives (such as, for example, a sparingly soluble salt). Sustained-release antiangiogenic compounds may be administered by intravascular, intravenous, intra-arterial, intramuscular, subcutaneous, intra-pericardial, or intra-coronary injection. Administration can also be oral, rectal, parenteral, intracisternal, intravaginal, intraperitoneal, topical (as by powders, ointments, gels, drops or transdermal patch), buccal, or as an oral or nasal spray.

Preparations for administration can be suitably formulated to give controlled release of antiangiogenic compounds. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features that allow a controlled release of the active substance. See, for example, U.S. Pat. No. 5,700,486.

In some embodiments, antiangiogenic compounds are delivered by way of a pump (see Sefton, CRC Crit. Ref. Biomed. Eng. 14:201, 1987; Buchwald et al., Surgery 88:507, 1980; Saudek et al., N. Engl. J. Med. 321:574, 1989) or by continuous subcutaneous infusions, for example, using a mini-pump. An intravenous bag solution may also be employed. The key factor in selecting an appropriate dose is the result obtained, as measured by increases or decreases in angiogenesis, or by other criteria for measuring control or prevention of disease, as are deemed appropriate by the practitioner. Other controlled release systems are discussed in the review by Langer (Science 249:1527-1533, 1990).

In another aspect of the disclosure, antiangiogenic compounds are delivered by way of an implanted pump, described, for example, in U.S. Pat. No. 6,436,091; U.S. Pat. No. 5,939,380; and U.S. Pat. No. 5,993,414. Implantable drug infusion devices are used to provide subjects with a constant and long term dosage or infusion of a drug or any other therapeutic agent. Essentially, such device may be categorized as either active or passive.

Active drug or programmable infusion devices feature a pump or a metering system to deliver the drug into the patient's system. An example of such an active drug infusion device currently available is the Medtronic SynchroMed™ programmable pump. Such pumps typically include a drug reservoir, a peristaltic pump to pump the drug out from the reservoir, and a catheter port to transport the pumped out drug from the reservoir via the pump to a patient's anatomy. Such devices also typically include a battery to power the pump, as well as an electronic module to control the flow rate of the pump. The Medtronic SynchroMed™ pump further includes an antenna to permit the remote programming of the pump.

Passive drug infusion devices, in contrast, do not feature a pump, but rather rely upon a pressurized drug reservoir to deliver the drug. Thus, such devices tend to be both smaller as well as cheaper as compared to active devices. An example of such a device includes the Medtronic IsoMed™. This device delivers the drug into the patient through the force provided by a pressurized reservoir applied across a flow control unit.

The implanted pump can be completely implanted under the skin of a subject, thereby negating the need for a percutaneous catheter. These implanted pumps can provide the patient with antiangiogenic compounds at a constant or a programmed delivery rate. Constant rate or programmable rate pumps are based on either phase-change or peristaltic technology. When a constant, unchanging delivery rate is required, a constant-rate pump is well suited for long-term implanted drug delivery. If changes to the infusion rate are expected, a programmable pump may be used in place of the constant rate pump system. Osmotic pumps may be much smaller than other constant rate or programmable pumps, because their infusion rate can be very low. An example of such a pump is described listed in U.S. Pat. No. 5,728,396.

For oral administration, the pharmaceutical compositions can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring, and sweetening agents as appropriate.

For administration by inhalation, the compounds for use according to the present disclosure are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

For topical administration, the compounds for use are, for example, mixed with ethanol, methanol, propylene glycol, or dimethyl sulfoxide, which act as a vehicle to facilitate uniform distribution of the compound to a target area of the subject's body, such as a wound or decubitus ulcer.

Pharmaceutical compositions that comprise an antiangiogenic compound as described herein as an active ingredient will normally be formulated with an appropriate solid or liquid carrier, depending upon the particular mode of administration chosen. The pharmaceutically acceptable carriers and excipients useful in this disclosure are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, antiangiogenic compounds can be formulated generally by mixing them at the desired degree of purity, in a unit dosage injectable form (solution, suspension, or emulsion), with a pharmaceutically acceptable carrier, for instance, one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the antiangiogenic compounds each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise an antiangiogenic compound, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of antiangiogenic compound will be dependent on the specific compound utilized, the subject being treated, the severity and type of the affliction, and the manner of administration.

VII. Therapeutic Uses

Methods are disclosed herein for inhibiting angiogenesis in a subject (or in an area in a subject) who has or is at risk for developing, for instance, a tumor (whether malignant or benign), retinopathy, psoriasis, endometriosis, arthritis, or any other disease for which it would be beneficial to inhibit angiogenesis. The methods include introducing a therapeutically effective amount of an antiangiogenic compound (e.g., one of Compounds 1-77) to the area (or systemically), thereby inhibiting angiogenesis in the subject.

In one embodiment, the angiogenesis inhibitory compound is administered locally. For subjects with a tumor, administration may be, for example, by intra-arterial injection to the tumor's arterial supply, or by direct injection into the tumor. Other routes of administration will be determined by the tumor location. Ovarian tumors are, for example, treated by intraperitoneal washing with the inhibitor. A brain tumor is, for example, treated by intra-arterial or intrathecal injection, by intranasal administration, by direct injection of affected brain areas, or by intravenous or intra-arterial injection following osmotic disruption of the blood brain barrier (see, for example, U.S. Pat. No. 5,124,146). Lung cancer is treated, for example, by direct injection of the tumor, by inhalation, or infusion into the lobar circulation of an affected lobe of the lung. Efficacy of the treatment is determined, for example, by monitoring tumor burden, or is indicated, for example, by a lessening of symptoms, such as pain.

For subjects with retinopathy, administration is, for example, by intra-ocular injection (for example, into the posterior chamber of the eye), or by topical ophthalmic administration. Alternatively, the agent may be administered intravascularly, for example into the vascular supply for the retinal artery. Efficacy of the treatment is determined, for example, by an improvement in vision, by a stabilization of vision, by a lack of new blood vessel formation in the retina, or by failure of the disease to progress.

For subjects with psoriasis, administration is, for example, by subcutaneous or intravenous injection, or by topical application. Efficacy of the treatment is determined, for example, by an abatement of psoriasis symptoms. For subjects with arthritis, administration is, for example, by intra-articular injection. Efficacy of the treatment is monitored, for example, by detecting an improvement in mobility, or a lessening of joint pain. For subjects with endometriosis, administration is, for example, by direct injection of the endometrial growths, or by intraperitoneal washing with the antiangiogenic compound. Efficacy of the treatment is shown, for example, by an improvement in mobility, or a lessening of pelvic pain.

Administration of the angiogenesis inhibitor may begin whenever a subject has developed, or is at risk for developing a tumor, retinopathy, psoriasis, or endometriosis, or when symptoms of inappropriate neovascularization are present.

Also disclosed are methods for treating undesirable angiogenesis and angiogenesis dependent or associated diseases, in a subject. The method includes administering one or more of the presently described compounds, or a combination of one or more of the compounds and one or more other pharmaceutical agents, to the subject in a pharmaceutically compatible carrier. The administration is made in an amount effective to inhibit the development or progression of angiogenesis and diseases associated with the same. Although the treatment can be used prophylactically in any patient in a demographic group at significant risk for such diseases, subjects can also be selected using more specific criteria, such as a definitive diagnosis of the condition.

The vehicle in which the drug is delivered can include pharmaceutically acceptable compositions of the drugs, using methods well known to those with skill in the art. Any of the common carriers, such as sterile saline or glucose solution, can be utilized with the drugs disclosed herein. Routes of administration include but are not limited to oral and parenteral routes, such as intravenous (iv), intraperitoneal (ip), rectal, topical, ophthalmic, nasal, and transdermal.

The drug may be administered in a suitable manner now known or later developed, e.g., orally or intravenously, in any conventional medium. For example, intravenous injection may be by an aqueous saline medium. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. A more complete explanation of parenteral pharmaceutical carriers can be found in *Remington: The Science and Practice of Pharmacy* (19$^{th}$ Edition, 1995) in chapter 95.

Examples of other pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions.

The compounds illustrated herein are ideally administered as soon as possible after unwanted angiogenesis is detected. For example, once unwanted angiogenesis has been confirmed or the presence of a tumor has been identified, a therapeutically effective amount of the drug is administered. The compound(s) can be administered in a single dose, or in multiple doses, for example daily, weekly, every two weeks, or monthly during a course of treatment.

Therapeutically effective doses of the presently described compounds can be determined by one of skill in the art, with a goal of achieving a desired level of antiangiogenesis as illustrated in the foregoing examples. In one embodiment, an antiangiogenic effective amount is an amount sufficient to achieve a statistically significant inhibition of angiogenesis compared to a control. Angiogenesis can be readily assessed using an assay, e.g., any of the assays described herein. Alternatively, angiogenesis can be determined in another assay or by direct or indirect signs of angiogenesis in a patient.

The relative toxicities of the compounds make it possible to administer in various dosage ranges. An example of such a dosage range is from about 0.5 to about 50 mg/kg body weight orally in single or divided doses. Another example of a dosage range is from about 1.0 to about 25 mg/kg body weight orally in single or divided doses. For oral administration, the compositions are, for example, provided in the form of a tablet containing from about 25 to about 500 mg of the active ingredient, particularly 100 mg of the active ingredient for the symptomatic adjustment of the dosage to the subject being treated.

The specific dose level and frequency of dosage for any particular subject may be varied and will depend upon a variety of factors, including the activity of the specific compound, the extent of existing angiogenic activity, the age, body weight, general health, sex, diet, mode and time of administration, rate of excretion, drug combination, and severity of the condition of the host undergoing therapy.

The pharmaceutical compositions containing at least one of the antiangiogenic SMs described herein can be used in the treatment of a variety of diseases mediated by angiogenesis. Examples of such angiogenesis-dependent diseases include all types of cancer, ocular neovascular disease, tumor formation and metastasis in tumors such as myeloma, rhabdomyosarcomas, retinoblastoma, Ewing sarcoma, neuroblastoma, osteosarcoma, colon, prostate, head and neck, breast, bladder, liver, pancreatic, lung, CNS, and blood-born tumors such as leukemia, also diseases such as hemangioma, ulcerative colitis, Crohn's disease, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eale's disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Also disclosed herein are combinations of one or more of the presently described compounds with one or more of various other angiogenesis inhibitor compounds. For example, the presently described compounds may be administered in combination with effective doses of other antiangiogenic agents. The term "administration in combination" refers to both concurrent and sequential (in either order) administration of the active agents. Non-limiting examples of antiangiogenic agents that can be used in combination with the compounds indentified herein are TNP-470, carbonic anhydrase inhibitors, endostatin, angiostatin, 2-methoxyestradiol, IMiD (Immune-modulating inhibitor drug) CC5013, matrix metalloproteinase inhibitors, and COL-3, as well as bFGF or VEGF inhibitor, such as SU5416, which is a specific VEGF-R antagonist, and SU6668 which blocks the receptors for VEGF, bFGF, and PDGF (see, for example, Liu et al., *Seminars in Oncology* 29 (Suppl 11): 96-103, 2002; Shepherd et al., *Lung Cancer* 34:S81-S89, 2001). In addition, the presently described compounds may be used in combination with other forms of cancer therapy (e.g., chemotherapy, radiation therapy, hormonal therapy) or other therapies known for use with angiogenesis-related disorders and diseases.

ADDITIONAL REFERENCES

1. Blower et al., Comparison of methods for sequential screening of large compound sets. *Comb Chem High Throughput Screen* 9(2):115-22, 2006
2. Blower et al., Systematic analysis of large screening sets in drug discovery. *Curr Drug Discov Technol* 1(1):37-47, 2004
3. Cross et al., Finding discriminating structural features by reassembling common building blocks. *J Med Chem* 46(22):4770-5, 2003
4. Gagarin et al., Using clustering techniques to improve hit selection in high-throughput screening. *J Biomol Screen* 11(8):903-14, 2006
5. Hopkins, Network pharmacology: the next paradigm in drug discovery. *Nat Chem Biol* 4(11):682-90, 2008
6. Makarenkov et al., HTS-Corrector: software for the statistical analysis and correction of experimental high-throughput screening data. *Bioinformatics* 22(11):1408-9, 2006

7. Makarenkov et al., An efficient method for the detection and elimination of systematic error in high-throughput screening. *Bioinformatics* 23(13):1648-57, 2007
8. Malo et al., Statistical practice in high-throughput screening data analysis. *Nat Biotechnol* 24(2):167-75, 2006
9. Yang et al., Building predictive models for protein tyrosine phosphatase 1B inhibitors based on discriminating structural features by reassembling medicinal chemistry building blocks. *J Med Chem* 47(24):5984-94, 2004
10. Zhang et al., A Simple Statistical Parameter for Use in Evaluation and Validation of High Throughput Screening Assays. *J Biomol Screen* 4(2):67-73, 1999

EXAMPLES

Example 1

Antiangiogenic Small Molecule Signatures

This example describes the identification and initial characterization of antiangiogenic small molecules using cell-based HTS methodology.

The present disclosure relates to the discovery of a new set of antiangiogenic small molecules. The antiangiogenic small molecules were identified through a combination of cell-based high throughput screening (HTS) together with chemoinformatic tools. This approach differs from the one taken by previous studies and pharmaceutical companies, in that the HTS is not targeted to a single subcellular molecule but instead targets a whole cellular process. In particular, two cell based assays have been developed which represent the two most important steps in angiogenesis: endothelial cell growth and tube formation.

Using the cell-based HTS screen, a new set of antiangiogenic small molecules have been discovered. Structure-activity-relationship (SAR) studies have shown that most of these new bioactive SMs are not related to known antiangiogenic SMs (FDA marketed; SMs currently in clinical trials; SMs annotated as antiangiogenic in chemical databases such as LeadScope, DrugBank, PubChem, etc.).

Overview of High Throughput Screen

The small molecule library screened was the NCI Diversity Set I (available on-line at dtp.nci.nih.gov/branches/dscb/diversity_explanation.html). The library was obtained from DTP/NCI (available on-line at dtp.nci.nih.gov/). This library contains 1974 small molecules (SMs) which are representative members of the same number of structural families each containing a variable number of members. The SMs included in the NCI Diversity Set I were selected to summarize the structural diversity found in a library of approximately 72,000 SMs. The library was obtained in 96-well plates and plate-to-plate DMSO dilutions were prepared at a stock concentration of 200 µM.

Figure 1:
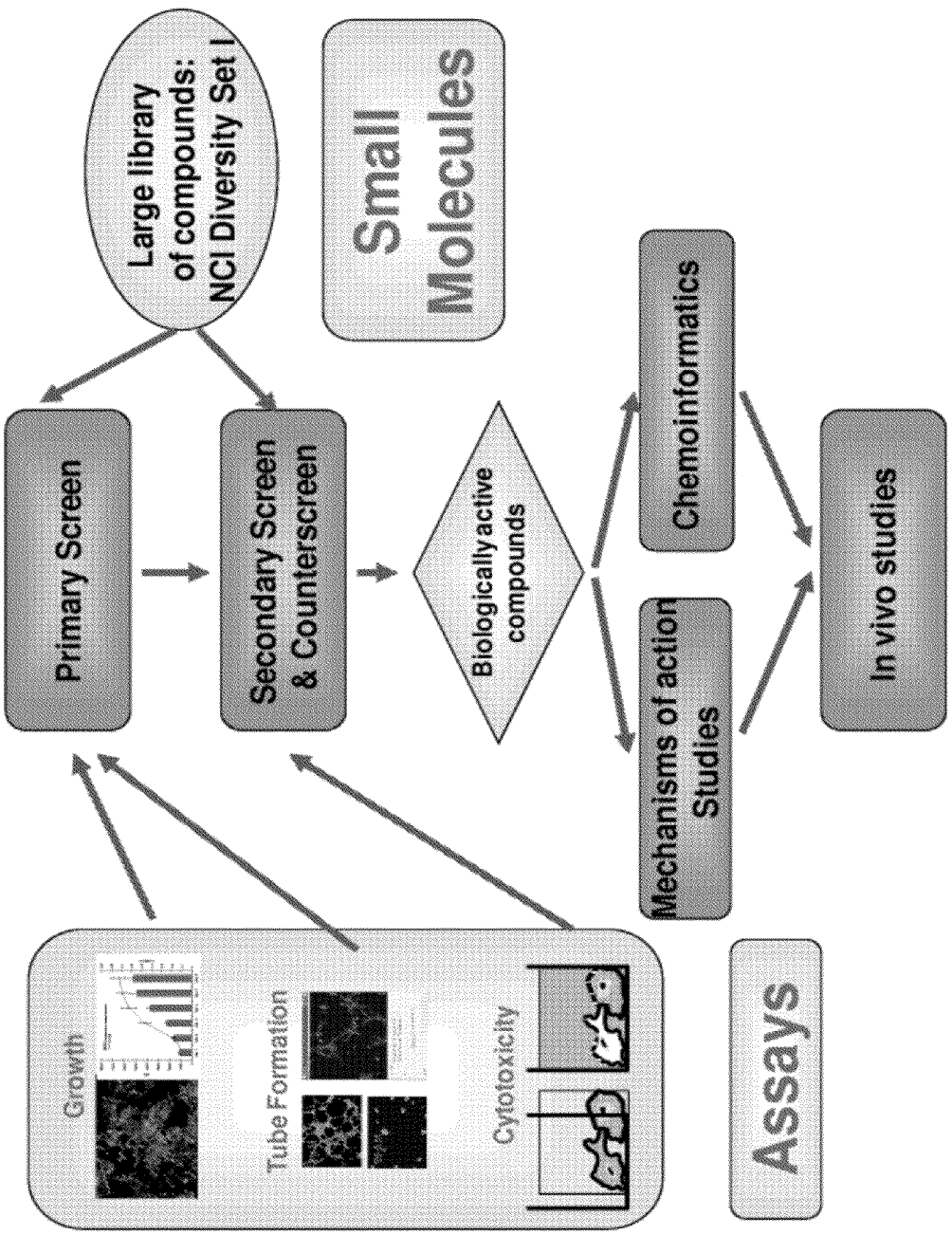
FIG. 1 shows a summarized workflow utilized for the identification of the new set of antiangiogenic SMs described herein. Additional details are provided in Example 1.

Two different cell-based HTS assays were developed which mimic the two main steps of the angiogenesis process: (1) a growth assay and (2) a tube formation assay (see below for more detail on assay protocols). The primary goal of the two HTSs was to find SMs which block either growth or tube formation of endothelial cells. These two assays comprised the primary screening which defined a first group of "bioactive compounds" which were then evaluated with secondary screening. See FIG. 1.

The secondary screening included two steps: (1) a cytotoxicity assay (described below) which was designed to discriminate cytotoxic compounds and (2) calculation of IC50 for every of the compounds identified in the primary screening. This secondary screening was also designed to eliminate putative false positives found in the primary screening and to evaluate the potency of the bioactive compounds. See FIG. 1.

The set of biologically active compounds obtained after the secondary screening was then used in a number of chemoinformatic studies as well as in in vitro studies in order to partially characterize their mechanism of action as well as compare them with existing antiangiogenic small molecules currently approved by the FDA, or in development by pharmaceutical companies.

Based on the compiled results of the HTS and other in vitro assays, a small set of compounds was chosen for in vivo studies. These studies included primarily xenograft experiments (See Example 2) and were designed to confirm the antiangiogenic activity of the compounds of interest, as well as test innovative anti-tumor/anti-angiogenic drug-combination regimens.

Experimental Design for HTS

Figure 2:
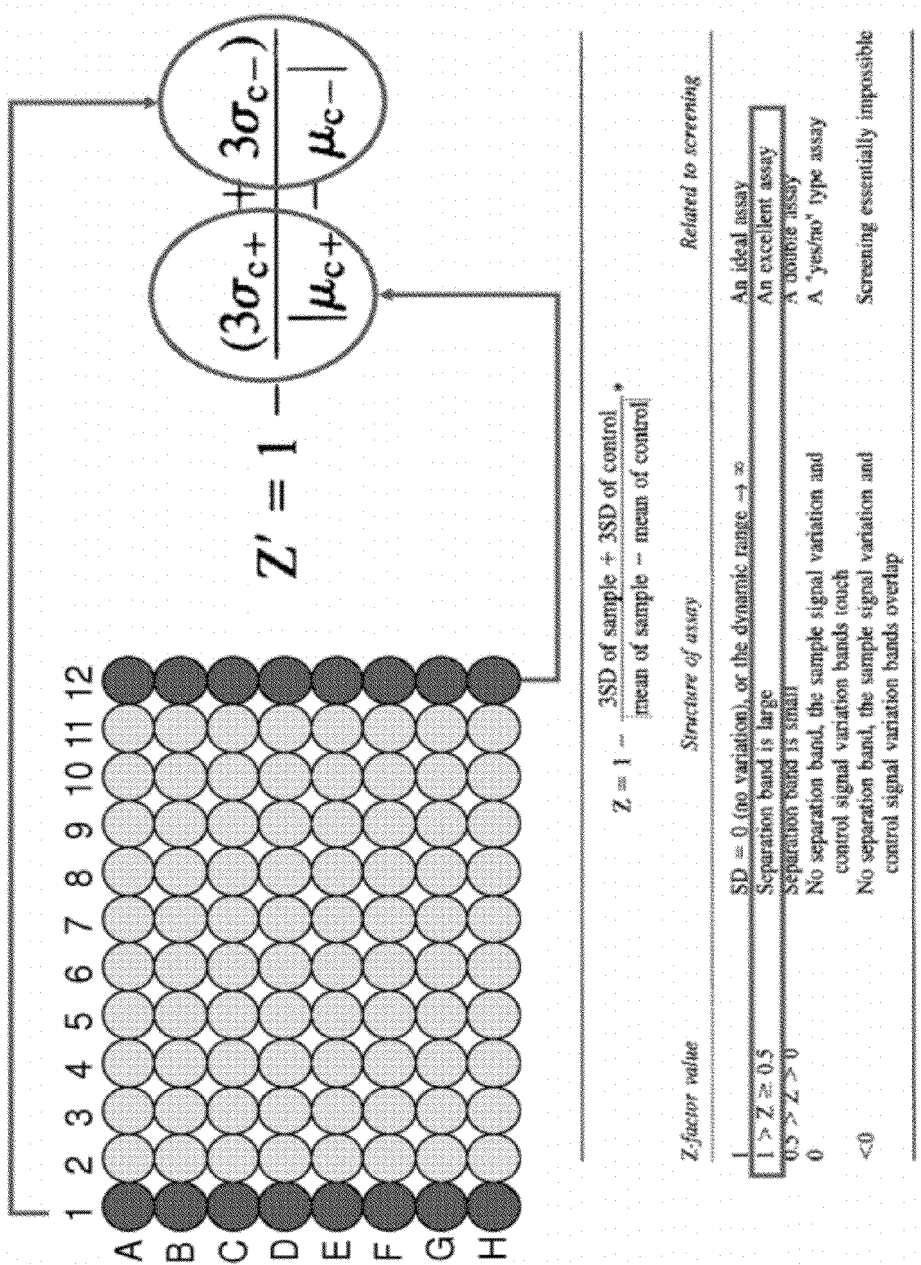
FIG. 2 shows the basic experimental design for the growth and tube formation HTS assays.

FIG. 2 illustrates the basic experimental design for all HTS assays; the same scheme was applied to both growth and tube formation assays. All assays were performed in clear bottom black 96-well plates. The plates were always arranged to include a column for negative controls (column 1), a column for positive controls (column 12), and 10 columns for evaluation of 80 compounds. In order to increase stringency and avoid false positives in the HTS assays, all compounds were tested at a low final concentration of 1 µM.

Both HTS assays (growth and tube formation) were based on the use of fluorescent reporter cell lines, essentially as described in U.S. application Ser. No. 12/060,752 (published as US 2009/0088341 on Apr. 2, 2009; incorporated herein by reference in its entirety). In summary, the cell lines porcine aortic endothelial cell (PAE), BEC (a human microvascular endothelial cell line), HMEC-1 (human microvascular endothelial cell line), A549 (human adenocarcinoma from the lung) and MCF7 (breast cancer cell line), among others, were stably transfected with different fluorescent proteins (green fluorescent protein -GFP-, yellow fluorescent protein -YFP-, red fluorescent protein -RFP-, and blue fluorescent protein -BFP-). Details on the production of these cell lines are described in U.S. application Ser. No. 12/060,752, which published as US 2009/0088341 on Apr. 2, 2009.

Growth HTS:

Previously, we demonstrated that there is a linear correlation between the fluorescence emission of the reporter cell lines and their number in culture. In summary, 1,000 cells/well were seeded in the 96-well plates described above. Cells in columns 2-12 were seeded in 10% FBS and cells in column 1 (negative control) were seeded in 0% FBS Small molecules (80 per plate) were added in columns 2-11 at a final concentration of 1 µM (both positive and negative controls were exposed to the same percentage of DMSO in wells containing test compounds). The fluorescence emitted by every well was measured spectrophotometrically (Infinite M200, TECAN®, Mannedorf, Switzerland) every 24 hours for 5-7 days. The assay quality was evaluated y calculating the Z' score (Zhang et al., *J. Biomol. Screen* 4(2):67-73, 1999) for every plate (only plates with Z'>0.5 were considered).

Tube Formation HTS:

In summary, 20,000 cells/well were seeded on top of 50 µl of pre-gelled GELTREX® gel matrix (Invitrogen, Carlsbad, Calif.). All cells were seeded in 10% FBS. Cells in column 1 (negative control) were exposed to 25 µM of suramine (an antiangiogenic factor known to be an inhibitor of endothelial tube formation). Small molecules (80 per plate) were added to columns 2-11 at a final concentration of 1 µM (both positive and negative controls were exposed to the same percentage of DMSO in wells containing test compounds). Plates were incubated for 5-7 hours and automatically imaged with the help of an epifluorescence microscope (Axiovert® 200M, Zeiss) equipped with a motorized stage and AxioVision® (Zeiss) software. Images were analyzed with the AngioApplication™ software (see below).

Hit Detection:

Data obtained from both the growth and tube formation HTSs were processed with the HTS Corrector software (Makarenkov et al., *Bioinformatics* 23(11):1408-0409, 2007). Data were normalized using "well correction" (Makarenkov et al., *Bioinformatics* 23(13):1648-1657, 2007) and hit identification was achieved using clustering by "sum of the average squared inside-cluster distances" (Gagarin et al., *J. Biomol. Screen* 11(8):903-914, 2006). For hit detection, a stringent threshold (sigma 3.5) was applied to avoid false positives.

Results of HTS Growth Assay

Figure 3:
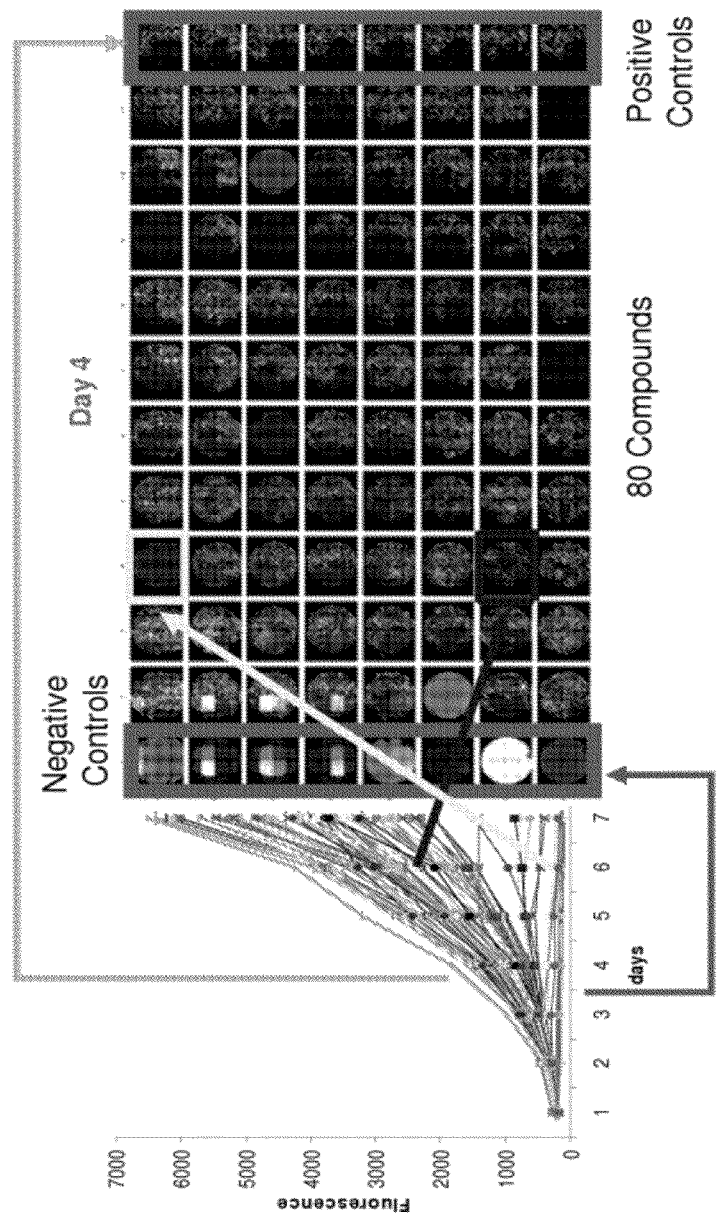
FIG. 3 shows the results on one of the plates (4143-11) included in the growth HTS using porcine aortic endothelial (PAE) cells. The plot represents fluorescence emission of all 96 wells over 7 days; as expected, fluorescence values increase over time although different wells show different fluorescence values. A composite image of all 96 wells is also shown (at day 4 of growth). Positive controls are shown in the far right column of wells; as expected, these controls show maximum values of fluorescence (in the plot) and high density of cells in the wells. A negative control is shown in the left column of wells; these show low fluorescence values in the plot and low cell density in the wells. Additionally, an example of a compound which blocks growth of PAE is shown in the first row, fourth column from the left, with low fluorescence values and few cells in the well. Furthermore, an example of a compound which does not inhibit the growth of PAE is shown in the seventh row, fourth column. In this case, high fluorescence values are shown in the plot together with a high number of cells in the well.

FIG. 3 shows the results on one the plates (4143-11) included in the growth HTS using PAE cells. The plot represents fluorescence emission of all 96 wells over 7 days. As expected, fluorescence values increase over time although different wells show different fluorescence values. A composite image of all 96 wells is also shown (at day 4 of growth). Positive controls are shown in the far right column of wells; as expected, these controls show maximum values of fluorescence (in the plot) and high density of cells in the wells. A negative control is shown in the left column of wells; these show low fluorescence values in the plot and low cell density in the wells. Additionally, an example of a compound which blocks growth of PAE is shown in the first row, fourth column from the left, with low fluorescence values and few cells in the well. Furthermore, an example of a compound which does not inhibit the growth of PAE is shown in the seventh row, fourth column. In this case, high fluorescence values are shown in the plot together with a high number of cells in the well.

Growth HTS Summary

Following the same protocol, HTS growth experiments were performed for PAE, BEC, A549 and MCF7 cells. These experiments were designed to explore the specificity of SMs with inhibitory activity in endothelial cells as compared to tumor cells from different anatomical origins.

FIG. 4 shows a heatmap that summarizes obtained results. The heatmap was constructed using the function heatmap.2 of the package gplots of the R statistical software. Clustering was performed using Euclidean distance matrix. The X axis shows the 1974 SM tested and the Y axis represents some of the growth HTS experiments performed. For all experiments measurements obtained in different days have been included and as expected show a high degree of consistency. Dark blue cells in the heatmap represent SM with strongest growth inhibitory activity and green and yellow SM with no activity on growth.

As expected, a small percentage of the SMs in the library had an inhibitory effect on the different cell lines. Interestingly, the majority of SMs shown to block growth of endothelial cells also inhibited the growth of tumor cells. Statistical analysis of these data identified 48 SMs which consistently inhibited the growth of endothelial cells (see TABLE 10).

Comparison of Growth Inhibitory Activity in Endothelial Cells vs. Tumor Cells

In the heatmap shown in FIG. 4, it is difficult to distinguish the SMs which preferentially inhibit the growth of endothelial cells or tumor cells. In order to study this possibility, average growth activity values for endothelial cells and tumor cells were compared in a bivariate scatterplot. Most of the SMs do not have an effect in growth in any of the cell lines tested and cluster in the center of the scatterplot (indicated within the middle-sized oval at the center of the plot). Also, most SMs with growth inhibitory activity affected with similar potency to tumor cells and endothelial cells and cluster in the lower left quadrant (indicated within the largest oval). Interestingly, a few SMs showed growth inhibitory activity in tumor cells but not in endothelial cells (small oval; see also TABLE 10). Growth activity of these small molecules is shown in the adjacent plot (small molecules are identified by their position in the plate; TABLE 10 correlates plate position to NSC number). No SMs were found with specific inhibitory activity for endothelial cells.

Specificity in the growth inhibitory activity of SMs is an important feature in the context of combinatorial drug therapy. In the treatment of angiogenesis-dependent tumors it is likely important to first deliver drugs that inhibit tumor growth but do not affect endothelial cells in order to not damage the vasculature which serves as drug delivery conduit to effectively reach the tumor. Therefore, drugs like the ones found in this study with the ability of specifically inhibit tumor growth but not endothelial cell growth would be of great value. Once the tumor has been significantly reduced, drugs with inhibitory activity in both tumor cells and endothelial cells would be preferred since both tumor cells and endothelial cells need to be targeted. A number of such drugs have also been found in this study (see TABLE 10).

Half Maximal Inhibitory Concentration ($IC_{50}$) in PAE

Dose response curves were constructed for all the SM of interest using PAE cells.

Data were fitted to non-linear sigmoid curves using GraphPad Prism (GraphPad software, Inc.). This assay was designed as a multipurpose experiment aimed to: (1) confirm bioactivity of SMs of interest, (2) confirm dose response of the growth inhibitory activity, and (3) calculate the half maximal inhibitory concentration (IC50). Since the initial screening was performed using a final SM concentration of 1 µM, IC50 form most compounds were confirmed to be in the range of $10^{-12}$ to $10^{-9}$ M (FIG. 6). This confirms that all the SMs discovered in this project show high growth inhibitory potency in endothelial cells (see TABLE 10).

Cytotoxicity Assay

Evaluation of the results obtained in the HTS growth assay does not provide information on whether the identified bioactive compounds inhibit growth through cell toxicity. Cytotoxicity is a common problem associated with non-peptidic small molecule drugs. In order to explore the cytotoxic potential of the SMs of interest, a novel high throughput cytotoxicity assay was previously developed (U.S. application Ser. No. 12/060,752; published as US 2009/0088341 on Apr. 2, 2009). The assay is based on the fact that cytotoxicity involves damage to the cell membrane which results in release of cytoplasmic content to the cell milieu. Since the reporter fluorescent cells used herein constitutively synthesize fluorescent proteins which are present in the cytoplasm, liberation of fluorescence to the medium can be used as an assessment of cytotoxicity.

FIG. 7 shows two different hypothetical outcomes of the cytotoxicity assay. In the lower area of the diagram, fluorescent cells are exposed to a cytotoxic substance, which results in the liberation of florescence to the cell culture medium. Both the fluorescence in the medium and the remaining fluorescence in the cells can be quantitated and used to determine percentage of cytotoxicity using the formula in the lower are of the figure. The plot shows the expected dose response curve when Triton X is used as cytotoxic agent on PAE cells.

FIG. 8 shows an example of four compounds with growth inhibitory activity from which two present a strong and moderate cytotoxic activity respectively. Using this cytotoxicity assay four compounds were identified as cytotoxic (see TABLE 10). Although these cytotoxic compounds may be of clinical interest, they were excluded from consideration for subsequent in vivo experiments.

Tube Formation

A HTS tube formation assay was also used for evaluation of antiangiogenic compounds. After being seeded, the endothelial cells are homogeneously distributed on the matrigel. Over time, cells migrate and interact with other endothelial cells to form tube-like structures which mimic the vasculature in vivo. Tube formation recapitulates several key steps of the angiogenic process: endothelial cell activation, cell migration, matrix degradation, cell polarization, cell to cell interaction and tube formation (among others).

Data Analysis using AngioApplication™

The major obstacle that was encountered in adapting the tube formation assay to a HTS format was performing a morphological quantitative analysis of the tube formation. For that purpose, an image analysis program named AngioApplication™ was developed (described in detail in U.S. application Ser. No. 12/060,752; published as US 2009/0088341 on Apr. 2, 2009). This software (FIG. 9) is able to rapidly assess a variety of metrics in images of tube formation including (but not limited to) tube length, node area, branching points, fractal dimension and lacunarity.

In order to understand which one of those metrics better explained the variability of the HTS tube formation assay data, a principal component analysis (PCA) was run. The PCA showed that branching index (the number of branches which converge in each node) and lacunarity (the average area of the empty spaces left by the tubes in the images) explain 53.8% and 45.0% respectively of the variability of the data (components C1 and C2 in the plots below) (see FIG. 10), making them the most appropriate metrics to measure tube formation.

Both emptiness (C1) and branching index (C2) were plotted in a bivariate scatter plot for every SM tested. The Euclidean distance between the average of the positive controls and every SM was used as metric to define anti-tube formation activity (calculations were done separately for every plate). In essence, compounds which are further away from the positive controls are more likely to be antiangiogenic. FIG. 11 illustrates the results from all the SMs in one test plates. As expected, most of the compounds (small squares clustered in center of graph) are located closely to the positive controls (large squares clustered near center of graph); this cluster is due to the fact that most small molecules do not have an effect on tube formation and therefore show similar branching index and emptiness values. In contrast, the negative controls (large squares clustered in lower right corner of graph) are positioned farther away from the positive controls. Representative images of the positive and negative controls are shown. Tube formation inhibitory compounds are detected as being located at an intermediate distance between the positive controls and the negative controls. A representative image of an active SM is shown (FIG. 11).

35 out of the 1974 compounds in the library (1.75%) were found to statistically significantly inhibit tube formation (see TABLE 10).

Dose Response of NSC 119889 in Tube Formation Assay

IC50 were calculated for all tube formation inhibitor SMs. As expected, most IC50 were in the range of $10^{-9}$ to $10^{-12}$M, making these compounds highly effective tube formation inhibitors. FIG. 12 shows an example of the dose response generated with compound NSC 119889.

Results of Screen and Analysis

FIG. 13 summarizes the results obtained in the growth and tube formation HTS for endothelial cells (for information on specific compounds, see TABLE 10). 2.4% (48) of the compounds were growth inhibitors and 1.75% (35) were tube formation inhibitors. Interestingly, 0.5% (11) of the compounds showed both growth and tube formation inhibitory activity. These SMs are especially interesting from the perspective of network pharmacology. It has been suggested that exquisitely selective compounds, compared with multitarget drugs, may exhibit lower than desired clinical efficacy (Hopkins, *Nat. Chem. Biol.* 4(11):682-690, 2008). However, it is challenging to design multitarget drugs while maintaining their drug-like properties. Here we have identified 11 SMs which show both growth and tube formation inhibitory activity (see TABLE 10).

Structure-Based Analysis

The structures of the antiangiogenic SMs identified herein were compared with annotated compounds in available annotated SM databases such as PubChem, DrugBank, LeadScope and FDA Marketed Drugs among others. Structural classifications were performed with LeadScope software. Only a few of our SMs were structurally related to annotated compounds in other databases (numbers in parenthesis in FIG. 14). This can be explained by the novel drug discovery methodology utilized in this project, which, as expected, results in novel SARs discoveries. Particularly interesting is the fact that none of the antiangiogenic SMs discovered herein are structurally related to any of the known antiangiogenic SMs. This supports the novelty of these newly-discovered antiangiogenic SMs and emphasizes that new SARs will result in exploitation of new cellular antiangiogenic pathways.

One of the areas for future work in this project is the identification of specific mechanisms of action for the newly-discovered antiangiogenic SMs. Some progress has already been achieved by applying Tanimoto's similarity algorithm (40-80% similarity) to compare the SMs described herein with SMs with known mechanism of action (Fligner et al., *Technomet*, 110-19, 2002. The structure of 12 compounds was found to be compatible with a potential mechanism of action (noted in parenthesis in "Mechanism of Action" in TABLE 10).

TABLE 10

| | | | BIOACTIVE SMALL MOLECULES | | | | |
|---|---|---|---|---|---|---|---|
| Compound | Location in Plate | NSC Numbers | Bioactivity | Cytotoxicity (%) | Growth IC50 (M) in PAE | Apoptosis PAE (RFU) | Mechanism of Action |
| 1 | 4125_G10 | 329226 | 1 | 7.564570142 | 3.719E-10 | 2.63432836 | |
| 2 | 4127_D3 | 15234 | 1 | 7.734030998 | 1.106E-10 | 0.70335821 | |
| 3 | 4127_E3 | 15226 | 1 | 9.013157895 | >1.00E-06 | 0.81599813 | |
| 4 | 4127_E6 | 24076 | 1 | 7.346874506 | >1.00E-06 | 0.6823694 | |
| 5 | 4127_E11 | 26081 | 1 | 7.103315772 | >1.00E-06 | 0.67490672 | |
| 6 | 4130_D6 | 133896 | 1 | 6.968579807 | 5.77E-10 | 0.68983209 | |
| 7 | 4131_C11 | 675865 | 1 | 7.322550338 | 1.118E-11 | 1.63945896 | |

TABLE 10-continued

BIOACTIVE SMALL MOLECULES

| Compound | Location in Plate | NSC Numbers | Bioactivity | Cytotoxicity (%) | Growth IC50 (M) in PAE | Apoptosis PAE (RFU) | Mechanism of Action |
|---|---|---|---|---|---|---|---|
| 8 | 4131_E10 | 10460 | 1 | 8.512827087 | >1.00E−06 | 0.85797575 | |
| 9 | 4132_D9 | 207895 | 1 | 7.69900465 | 2.297E−10 | 0.98763993 | Tubulin Binder (80) |
| 10 | 4133_H4 | 99445 | 1 | 6.79005243 | >1.00E−06 | 1.05550373 | DNA synthesis inhibitor (80) |
| 11 | 4133_H10 | 88903 | 1 | 18.69722406 | 2.366E−11 | 0.90298507 | |
| 12 | 4134_A8 | 177407 | 1 | 6.734835623 | 3.016E−10 | 1.66487873 | |
| 13 | 4135_D8 | 123111 | 1 | 7.062612517 | 1.65E−11 | 0.96338619 | Alkylating agent (40) |
| 14 | 4136_F10 | 329261 | 1 | 6.510813456 | 1.885E−09 | 0.93913246 | |
| 15 | 4137_C5 | 13316 | 1 | 7.93334652 | 6.552E−10 | 0.93516791 | |
| 16 | 4137_G3 | 5844 | 1 | 6.779904279 | >1.00E−06 | 0.90578358 | |
| 17 | 4138_C3 | 5857 | 1 | 7.344979376 | 3.979E−10 | 2.10704291 | |
| 18 | 4138_E2 | 656202 | 1 | 7.599327541 | 4.635E−10 | 1.5886194 | |
| 19 | 4138_G2 | 2186 | 1 | 6.564555483 | 9.626E−10 | 1.34001866 | |
| 20 | 4138_H7 | 97845 | 1 | 8.180294654 | 4.684E−09 | 0.94986007 | Tubulin binder (80) |
| 21 | 4139_H6 | 368891 | 1 | 6.565516968 | 2.291E−11 | 0.96805037 | |
| 22 | 4140_A3 | 126710 | 1 | 6.745211776 | 1.535E−12 | 1.22807836 | |
| 23 | 4140_C2 | 109836 | 1 | 7.015392379 | 1.207E−09 | 0.82649254 | |
| 24 | 4140_D11 | 67485 | 1 | 8.537374177 | >1.00E−06 | 1.37546642 | |
| 25 | 4140_E9 | 47932 | 1 | 9.566749391 | 2.267E−10 | 1.43283582 | Antifungal (60) |
| 26 | 4141_F2 | 176327 | 1 | 8.243912666 | 8.379E−11 | 2.6798041 | |
| 27 | 4141_F6 | 48630 | 1 | 7.89544627 | >1.00E−06 | 0.95895522 | |
| 28 | 4141_G8 | 71669 | 1 | 8.645721955 | 7.412E−11 | 1.34025187 | |
| 29 | 4142_E8 | 150289 | 1 | 9.782711919 | >1.00E−06 | 0.97504664 | |
| 30 | 4143_A4 | 311153 | 1 | 8.808756865 | 9.265E−10 | 0.63899254 | |
| 31 | 4143_A9 | 45238 | 1 | 7.617204067 | 0.0005062 | 1.23763993 | |
| 32 | 4143_C6 | 156305 | 1 | 6.821926473 | >1.00E−06 | 1.34981343 | Topoisomerase II inhibitor (40) |
| 33 | 4143_C9 | 62914 | 1 | 7.444298641 | 2.801E−10 | 2.06296642 | |
| 34 | 4143_C10 | 606985 | 1 | 10.19900361 | 9.919E−12 | 2.93703358 | Topoisomerase II inhibitor (80) |
| 35 | 4144_G7 | 254681 | 1 | 7.976999744 | 2.41E−11 | 3.30060634 | Topoisomerase II inhibitor (60) |
| 36 | 4145_D4 | 268665 | 1 | 7.657827234 | 2.453E−10 | 0.97737873 | DNA synthesis inhibitor (60) |
| 37 | 4145_G5 | 306698 | 1 | 7.923868435 | >1.00E−06 | 2.03708022 | |
| 38 | 4121_A6 | 4972 | 2 | 6.742820667 | | 0.70335821 | |
| 39 | 4121_A8 | 19630 | 2 | 8.537524348 | | 0.73997201 | |
| 40 | 4123_H10 | 2805 | 2 | 7.23286013 | | 0.6770056 | |
| 41 | 4124_E8 | 16555 | 2 | 7.591147773 | | 0.8048041 | |
| 42 | 4125_B6 | 3535 | 2 | 6.993009343 | | 0.84584888 | |
| 43 | 4127_G11 | 27063 | 2 | 6.439058017 | | 1.13456157 | |
| 44 | 4128_D5 | 47924 | 2 | 6.449536192 | | 0.89412313 | |
| 45 | 4129_D8 | 36738 | 2 | 6.610206089 | | 0.87290112 | |
| 46 | 4130_H10 | 108895 | 2 | 7.361554387 | | 0.86054104 | |
| 47 | 4131_H11 | 681152 | 2 | 6.856025461 | | 0.59864739 | |
| 48 | 4136_E6 | 632536 | 2 | 7.00534393 | | 0.80806903 | |
| 49 | 4140_G4 | 122351 | 2 | 6.968172168 | | 1.23507463 | |
| 50 | 4142_D8 | 268879 | 2 | 13.72791324 | | 3.10284515 | DNA synthesis inhibitor (40) |
| 51 | 4142_H2 | 48458 | 2 | 8.564443963 | | 1.66954291 | |
| 52 | 4143_E3 | 209910 | 2 | 9.581766236 | | 1.22504664 | |
| 53 | 4143_E10 | 328087 | 2 | 8.762714287 | | 1.21245336 | |
| 54 | 4144_D9 | 521777 | 2 | 9.262232258 | | 8.04127799 | |
| 55 | 4144_D11 | 310551 | 2 | 28.17915266 | | 0.92863806 | |
| 56 | 4144_E2 | 292222 | 2 | 7.520592126 | | 3.41907649 | Tubulin Binder (60) |
| 57 | 4144_G11 | 321237 | 2 | 7.377240696 | | 1.14552239 | DNA synthesis inhibitor (40) |
| 58 | 4144_H2 | 259969 | 2 | 11.1918293 | | 5.61497201 | |
| 59 | 4144_H5 | 259968 | 2 | 9.793991594 | | 6.21501866 | |
| 60 | 4145_C4 | 203328 | 2 | 6.947818406 | | 1.26096082 | |
| 61 | 4145_E6 | 166687 | 2 | 7.901324787 | | 1.84071828 | |
| 62 | 4145_H6 | 119889 | 2 | 13.63421931 | | 1.26888993 | |
| 63 | 4132_F3 | 676693 | 3 | 7.48119818 | 1.546E−11 | 1.44776119 | **** |
| 64 | 4135_D7 | 122657 | 3 | 7.092535262 | 2.79E−10 | 0.78941231 | **** |
| 65 | 4138_B4 | 295642 | 3 | 13.74937928 | 1.085E−11 | 2.22714552 | |
| 66 | 4139_B8 | 13480 | 3 | 13.10907474 | 4.117E−10 | 1.04967351 | |
| 67 | 4139_B11 | 150117 | 3 | 7.776786651 | 9.16E−11 | 0.67537313 | **** |

TABLE 10-continued

BIOACTIVE SMALL MOLECULES

| Compound | Location in Plate | NSC Numbers | Bioactivity | Cytotoxicity (%) | Growth IC50 (M) in PAE | Apoptosis PAE (RFU) | Mechanism of Action |
|---|---|---|---|---|---|---|---|
| 68 | 4139__C8 | 18877 | 3 | 19.12681814 | 1.404E−10 | 1.3542444 | |
| 69 | 4141__B4 | 48300 | 3 | 8.261734079 | 3.837E−10 | 1.1354944 | **** |
| 70 | 4142__A2 | 321206 | 3 | 38.52519823 | 6.112E−12 | 1.02122201 | |
| 71 | 4142__B6 | 292596 | 3 | 9.501696674 | 7.577E−11 | 2.30573694 | **** |
| 72 | 4144__G4 | 112200 | 3 | 13.88370945 | 1.386E−10 | 1.36847015 | |
| 73 | 4145__D5 | 274547 | 3 | 15.66300644 | 3.579E−10 | 0.90625 | |
| 74 | 4123__B6 | 4265 | 4 | | | | |
| 75 | 4130__G5 | 130830 | 4 | | | | |
| 76 | 4133__D11 | 54044 | 4 | | | | |
| 77 | 4143__A5 | 327705 | 4 | | | | |

Bioactivity
1 Endothelial Cell Growth Inhibitor
2 Tube Formation Inhibitor
3 Growth Inhibitor + Tube Formation Inhibitor
4 Specific Tumor Cell Growth Inhibitor
**** Compounds with both growth and tube formation inhibitory activities and no significant cytotoxicity.

Example 2

In Vivo Inhibition of Angiogenesis in Xenograft Tumors

This example shows the in vivo inhibition of angiogenesis in tumor xenografts by administration of selected small molecules described herein.

Methods

For generation of mouse xenografts, female athymic nude mice were injected with $5 \times 10^6$ A549 or SK-ML-1 cells (100 µl/mouse) in the left hindquarters. The resulting tumors were measured three times a week and body weight was measured twice a week. 14 days following tumor cell injection, mice with tumor burdens greater than 100 mm$^3$ or less than 50 mm$^3$ were eliminated from the study. The remaining mice were randomized into groups (10 animals per group) and treated three times a week (Mon/Wed/Fri) for four weeks with 100 of 10 µM sterile drug solutions (stored at 4° C.) that were administered via IP injection. Tumors were measured three times per week (Mon/Wed/Fri) for four additional weeks and mice weighed twice weekly (Tues/Thu) for an additional four weeks. On week six or when tumors exceeded 2 cm, the mice were euthanized. A full necropsy was performed and any abnormal tissues were snap frozen (−80° C.). Tumors were excised and bisected into four parts. Two parts were fixed in 2% formalin overnight at 4° C., rinsed in cold PBS and prepared for paraffin embedding. The other two parts were snap frozen on dry ice or liquid nitrogen and stored at −80° C.

Results 7 of the 77 SMs described above were chosen for in vivo xenograft experiments. SMs were selected based on the type of inhibition (tube formation-NSC 19630, NSC 292222, NSC 259969; or tube formation+growth-NSC 122657, NSC 150117, NSC 48300, NSC 292596), percentage of inhibition, low cytotoxicity levels and availability. For the tumor xenografts, two different human cancer models were chosen. A549 is a lung carcinoma which induces almost exclusively peritumoral vasculature in subcutaneous tumors. In contrast, SK-ML-1 is a leiomyosarcoma which induces high levels of intratumoral angiogenesis. Every experiment included a negative PBS control as well as the known antiangiogenic drug AVASTIN® as a positive control. AVASTIN® was previously shown to significantly inhibit the growth of both A549 as well as SK-ML-1.

As shown in FIG. 15, all the small molecules inhibited tumor growth to varying degrees. In general, and as expected, the small molecules more strongly inhibited the growth of the angiogenic tumor SK-ML-1 (bottom panels) in comparison to the less angiogenic tumor A549 (top panels). Of the SMs tested, the strongest inhibitors of tumor growth were NSC 48300, NSC 150117 and NSC 259969, all of which showed potencies similar to AVASTIN® in the SK-ML-1 model.

Example 3

Tubulin Binding Potential of Antiangiogenic Small Molecules

Many known antiangiogenic drugs bind to tubulin and interfere with its polymerization. Likewise, it has also been shown that molecules which interfere with tubulin polymerization are potentially antiangiogenic. In contrast, the above-described SAR analysis predicted that none of the seven small molecules shown in Example 2 to be antiangiogenic in xenograft assays would inhibit tubulin polymerization. This example confirms this prediction.

The tubulin binding activity of the small molecules studied in vivo was characterized using a fluorescence-based, tubulin polymerization assay from Cytoskeleton (Denver, Colo.; Cat. # BK011P), according to the manufacturer's instructions. As predicted by the SAR analysis, none of the small molecules studied interfered with tubulin polymerization (FIG. 16).

Example 4

Effect of SMs on Receptor Tyrosine Kinase Activity

Most of the currently FDA approved antiangiogenic therapies (such as AVASTIN® or sunitinib) target receptor tyrosine kinase (RTK) activity. It has recently been proposed by independent groups (Pàez-Ribes et al., *Cancer Cell,* 15: 220-231, 2009; Ebos et al., *Cancer Cell,* 15: 232-239, 2009) that RTK inhibitors have deleterious collateral effects, including stimulation of metastasis and alternative angiogenesis pathways other than those inhibited by the drugs. This example shows the characterization of the RTK inhibitory activity of a subset of the small molecules described herein.

To characterize the RTK inhibitory activity of the antiangiogenic SMs described herein, 36 compounds were chosen and screened using Invitrogen's SelectScreen® kinase activity profiling service (described on-line at tools.invitrogen.com/content.cfm?pageid=10413#selection). VEGFR1 and FGFR2 RTK inhibitory activities were studied. The results of the screen are detailed in Table 11. The % inhibition (and mean % inhibition) of RTK activity from two independent trials is shown Of the seven SMs tested in vivo in Example 2, only NSC 19630 and NSC 48300 showed RTK inhibitory activity, and only for for the VEGFR2 receptor. Overall, a small minority of the SMs tested had any substantial kinase inhibitory activity. This observation supports a mechanism of antiangiogenic action other than RTK inhibition for most of the SMs described herein.

TABLE 11

KINASE INHIBITION

| Comp. NSC# | Kinase Activity Tested | % Inhibition | % Inhibition | Mean % Inhibition |
|---|---|---|---|---|
| 4972 | FGFR1 | 3 | −7 | −2 |
| 4972 | KDR(VEGFR2) | 2 | 11 | 7 |
| *19630* | *FGFR1* | *2* | *−2* | *0* |
| *19630* | *KDR(VEGFR2)* | *90* | *91* | *90* |
| 2805 | FGFR1 | 1 | 10 | 6 |
| 2805 | KDR(VEGFR2) | 42 | 52 | 47 |
| 16555 | FGFR1 | 3 | 3 | 3 |
| 16555 | KDR(VEGFR2) | 11 | 11 | 11 |
| 3535 | FGFR1 | −1 | −3 | −2 |
| 3535 | KDR(VEGFR2) | 10 | 5 | 8 |
| 27063 | FGFR1 | −3 | −2 | −3 |
| 27063 | KDR(VEGFR2) | 12 | 11 | 11 |
| 47924 | FGFR1 | 1 | 3 | 2 |
| 47924 | KDR(VEGFR2) | 21 | 18 | 19 |
| 36738 | FGFR1 | −1 | 4 | 1 |
| 36738 | KDR(VEGFR2) | 16 | 17 | 16 |
| 108895 | FGFR1 | 4 | 4 | 4 |
| 108895 | KDR(VEGFR2) | 5 | 6 | 6 |
| 681152 | FGFR1 | 4 | 3 | 3 |
| 681152 | KDR(VEGFR2) | 10 | 8 | 9 |
| 676693 | FGFR1 | 4 | 3 | 3 |
| 676693 | KDR(VEGFR2) | 1 | 8 | 5 |
| *122657* | *FGFR1* | *−3* | *−3* | *−3* |
| *122657* | *KDR(VEGFR2)* | *14* | *14* | *14* |
| 632536 | FGFR1 | 1 | 1 | 4 |
| 632536 | KDR(VEGFR2) | 15 | 16 | 16 |
| 295642 | FGFR1 | 2 | 9 | 6 |
| 295642 | KDR(VEGFR2) | 19 | 17 | 18 |
| *150117* | *FGFR1* | *2* | *7* | *5* |
| *150117* | *KDR(VEGFR2)* | *28* | *24* | *26* |
| 13480 | FGFR1 | 5 | 10 | 8 |
| 13480 | KDR(VEGFR2) | 4 | 2 | 3 |
| 18877 | FGFR1 | −3 | 0 | −2 |
| 18877 | KDR(VEGFR2) | 10 | 4 | 7 |
| 122351 | FGFR1 | −1 | 4 | 1 |
| 122351 | KDR(VEGFR2) | 4 | 4 | 4 |
| *48300* | *FGFR1* | *8* | *10* | *9* |
| *48300* | *KDR(VEGFR2)* | *76* | *78* | *77* |
| 321206 | FGFR1 | 5 | 5 | 5 |
| 321206 | KDR(VEGFR2) | 52 | 45 | 49 |
| *292596* | *FGFR1* | *4* | *4* | *4* |
| *292596* | *KDR(VEGFR2)* | *9* | *18* | *14* |
| 268879 | FGFR1 | 3 | −2 | 1 |
| 268879 | KDR(VEGFR2) | 40 | 38 | 39 |
| 48458 | FGFR1 | 5 | 8 | 6 |
| 48458 | KDR(VEGFR2) | 13 | 9 | 11 |
| 328087 | FGFR1 | 3 | 5 | 4 |
| 328087 | KDR(VEGFR2) | 9 | 9 | 9 |
| 209910 | FGFR1 | 2 | 5 | 4 |
| 209910 | KDR(VEGFR2) | 9 | 10 | 10 |
| 310551 | FGFR1 | −5 | −1 | −3 |
| 310551 | KDR(VEGFR2) | 21 | 18 | 20 |
| 521777 | FGFR1 | 1 | 0 | 1 |
| 521777 | KDR(VEGFR2) | 10 | 8 | 9 |
| *292222* | *FGFR1* | *2* | *5* | *3* |
| *292222* | *KDR(VEGFR2)* | *8* | *7* | *7* |
| 321237 | FGFR1 | 1 | 5 | 6 |
| 321237 | KDR(VEGFR2) | 105 | 104 | 105 |
| 112200 | FGFR1 | 9 | 5 | 7 |
| 112200 | KDR(VEGFR2) | 100 | 99 | 99 |
| *259969* | *FGFR1* | *3* | *3* | *3* |
| *259969* | *KDR(VEGFR2)* | *0* | *9* | *5* |
| 259968 | FGFR1 | 5 | 2 | 3 |
| 259968 | KDR(VEGFR2) | 8 | 9 | 8 |
| 203328 | FGFR1 | 4 | 4 | 4 |
| 203328 | KDR(VEGFR2) | 9 | 7 | 8 |
| 274547 | FGFR1 | 4 | 7 | 6 |
| 274547 | KDR(VEGFR2) | 14 | 12 | 13 |
| 166687 | FGFR1 | 21 | 22 | 22 |
| 166687 | KDR(VEGFR2) | 9 | 6 | 8 |
| 119889 | FGFR1 | 96 | 95 | 96 |
| 119889 | KDR(VEGFR2) | 103 | 104 | 103 |

SMs that inhibited kinase activity 40% or more are indicated in bold.
SMs also characterized for in vivo activity are italicized.

Example 5

Effect of Antiangiogenic SMs on Gene Expression During Endothelial Tube Formation This example shows the effect of anti-angiogenic small molecules described herein on the expression of genes in the angiogenesis pathway.

Methods

For gene expression studies, three independent experiments were run for each SM tested. 90.000 cells/well (6 wells/treatment) of dermal microvascular endothelial cells (Lonza, Walkersville, Md.) were seeded on polymerized GELTREX™ gel matrix (Invitrogen, Carlsbad, Calif.) in 24 well plates. Wells were immediately treated with the same volume of 1 μM SM or PBS. After 24 hours incubation at 37° C. and 5% $CO_2$, cells were extracted using Cell Recovery Solution (BD Biosciences, San Jose, Calif., Cat. #354253). Total RNA was extracted with the RNeasy Mini Kit (Qiagen, Valencia, Calif., Cat. #74104), and retrotranscribed using SUPERSCRIPT® First-Strand reverse transcriptase (Invitrogen, Carlsbad, Calif., Cat. #11904-018). The real time PCR reactions were performed in an Opticon 2 cycler (MJ Research, Waltham, Mass.). Amplification was performed in a final volume of 25 μl, containing 2 μl cDNA (1:10 dilution from the reversed transcribed reaction) and 2 μl of primer mixture (10 μM each of forward and reverse primers). Samples were amplified as follows: after initial denaturation at 95 C for 2 minutes, reactions were run for 46 cycles at 95° C. for 30 seconds, 60° C. for 30 seconds, and 72° C. for 45 seconds. Fluorescence was measured in every cycle and a melting curve was run after the PCR by increasing temperature from 50 to 96° C. (in 0.5° C. increments). A defined single peak was obtained for all amplicons, thus confirming the specificity of the amplification.

Results

To better understand the mechanism of action of the seven small molecules used in the in vivo studies presented in Example 2, the effect of these molecules on the expression of angiogenesis genes in primary endothelial cells during tube formation was studied. The genes that were monitored were selected based on their relevance to the angiogenesis process. The genes assayed and primers used in the real-time PCR are presented in Tables 12 and 13. All experiments were done in triplicate. The results are shown in the volcano plots of FIG.

17. Log 2 fold-change is presented in the X-axis and log 10 P value in the Y-axis. These results are also summarized below in Table 14.

TABLE 12

GENES IN REAL TIME PCR ARRAYS

| Gene Symbol | GenBank Accession | NCBI Protein Accession | Coding DNA Length |
|---|---|---|---|
| AKT1 | NM_005163 | NP_005154 | 1443 |
| ANGPT1 | NM_001146 | NP_001137 | 1497 |
| ANGPT2 | AF187858 | AAF76526 | 1335 |
| ANGPTL3 | NM_014495 | NP_055310 | 1383 |
| ANGPTL4 | NM_016109 | NP_057193 | 1221 |
| ANPEP | NM_001150 | NP_001141 | 2904 |
| BAI1 | NM_001702 | NP_001693 | 4755 |
| CCL11 | NM_002986 | NP_002977 | 294 |
| CCL2 | NM_002982 | NP_002973 | 300 |
| CDH5 | NM_001795 | NP_001786 | 2355 |
| COL18A1 | NM_030582 | NP_085059 | 4551 |
| COL4A3 | NM_000091 | NP_000082 | 5013 |
| dll4 | NM_019074 | NP_061947 | 2058 |
| CXCL10 | NM_001565 | NP_001556 | 297 |
| CXCL3 | NM_002090 | NP_002081 | 321 |
| CXCL5 | NM_002994 | NP_002985 | 345 |
| CXCL6 | NM_002993 | NP_002984 | 345 |
| CXCL9 | NM_002416 | NP_002407 | 378 |
| TYMP | NM_001953 | NP_001944 | 1449 |
| S1PR1 | NM_001400 | NP_001391 | 1149 |
| EFNA1 | NM_182685 | NP_872626 | 552 |
| EFNA3 | NM_004952 | NP_004943 | 717 |
| EFNB2 | NM_004093 | NP_004084 | 1002 |
| EGF | NM_001963 | NP_001954 | 3624 |
| ENG | NM_000118 | NP_000109 | 1878 |
| EPHB4 | NM_004444 | NP_004435 | 2964 |
| EREG | NM_001432 | NP_001423 | 510 |
| FGF1 | NM_000800 | NP_000791 | 468 |
| FGF2 | NM_002006 | NP_001997 | 633 |
| FGFR3 | NM_000142 | NP_000133 | 2421 |
| FIGF | NM_004469 | NP_004460 | 1065 |
| FLT1 | NM_002019 | NP_002010 | 4017 |
| HAND2 | NM_021973 | NP_068808 | 654 |
| HGF | NM_000601 | NP_000592 | 2187 |
| HIF1A | NM_001530 | NP_001521 | 2481 |
| HPSE | NM_006665 | NP_006656 | 1632 |
| ID1 | NM_002165 | NP_002156 | 468 |
| ID3 | NM_002167 | NP_002158 | 360 |
| IFNA1 | NM_024013 | NP_076918 | 570 |
| IFNB1 | NM_002176 | NP_002167 | 564 |
| IFNG | NM_000619 | NP_000610 | 501 |
| IGF1 | NM_000618 | NP_000609 | 462 |
| IL1B | NM_000576 | NP_000567 | 810 |
| IL6 | NM_000600 | NP_000591 | 639 |
| IL8 | NM_000584 | NP_000575 | 300 |
| ITGAV | NM_002210 | NP_002201 | 3147 |
| ITGB3 | NM_000212 | NP_000203 | 2367 |
| JAG1 | NM_000214 | NP_000205 | 3657 |
| KDR | NM_002253 | NP_002244 | 4071 |
| LAMA5 | NM_005560 | NP_005551 | 11088 |
| LECT1 | NM_007015 | NP_008946 | 1005 |
| LEP | NM_000230 | NP_000221 | 504 |
| MDK | NM_002391 | NP_002382 | 432 |
| MMP2 | NM_004530 | NP_004521 | 1983 |
| MMP9 | NM_004994 | NP_004985 | 2124 |
| Notch4 | NM_004557 | NP_004548 | 6009 |
| NRP1 | NM_003873 | NP_003864 | 2772 |
| NRP2 | NM_003872 | NP_003863 | 2781 |
| PDGFA | NM_002607 | NP_002598 | 636 |
| PECAM1 | NM_000442 | NP_000433 | 2217 |
| PGF | NM_002632 | NP_002623 | 513 |
| PLAU | NM_002658 | NP_002649 | 1296 |
| PLG | NM_000301 | NP_000292 | 2433 |
| PLXDC1 | NM_020405 | NP_065138 | 1503 |
| PROK2 | NM_021935 | NP_068754 | 327 |
| PTGS1 | NM_000962 | NP_000953 | 1800 |
| SERPINF1 | NM_002615 | NP_002606 | 1257 |
| SPHK1 | NM_021972 | NP_068807 | 1197 |
| STAB1 | NM_015136 | NP_055951 | 7713 |
| TEK | NM_000459 | NP_000450 | 3375 |
| TGFA | NM_003236 | NP_003227 | 483 |
| TGFB1 | NM_000660 | NP_000651 | 1176 |
| TGFB2 | NM_003238 | NP_003229 | 1245 |
| TGFBR1 | NM_004612 | NP_004603 | 1512 |
| THBS1 | NM_003246 | NP_003237 | 3513 |
| THBS2 | NM_003247 | NP_003238 | 3519 |
| TIMP1 | NM_003254 | NP_003245 | 624 |
| TIMP2 | NM_003255 | NP_003246 | 663 |
| TIMP3 | NM_000362 | NP_000353 | 636 |
| TNF | NM_000594 | NP_000585 | 702 |
| TNFAIP2 | NM_006291 | NP_006282 | 1965 |
| VEGFA | NM_003376 | NP_003367 | 648 |
| VEGFC | NM_005429 | NP_005420 | 1260 |
| CD248 | NM_020404 | NP_065137 | 2274 |
| GPR124 | AB040964 | BAA96055 | 3621 |
| PLXDC1 | NM_020405 | NP_065138 | 1503 |
| ANTXR1 | NM_032208 | NP_115584 | 1695 |
| RASD2 | NM_014310 | NP_055125 | 801 |
| ARHGEF17 | NM_014786 | NP_055601 | 6192 |
| TNS3 | AL833845 | CAD38705 | 2714 |
| DKK3 | NM_015881 | NP_056965 | 1053 |
| MMP11 | NM_005940 | NP_005931 | 1467 |
| NID1 | BC045606 | AAH45606 | 3345 |
| THY1 | NM_006288 | NP_006279 | 486 |
| CST4 | NM_001899 | NP_001890 | 426 |
| MRC2 | NM_006039 | NP_006030 | 4440 |
| TNS1 | AK001785 | BAA91910 | 1197 |
| BMP1 | AF318323 | AAL55830 | 933 |
| COMT | NM_000754 | NP_000745 | 816 |
| PTPRCAP | NM_005608 | NP_005599 | 621 |
| 57722 | AB046848 | BAB13454 | 2943 |
| EXTL3 | NM_001440 | NP_001431 | 2760 |
| vWF | NM_000552 | NP_000543 | 8442 |
| PNMT | NM_002686 | NP_002677 | 849 |
| 58488 | BC005112 | AAH05112 | 582 |
| ltbp4 | AK074499 | BAC11024 | 1911 |
| 23001 | AK055806 | BAB71020 | 2169 |
| 4247 | NM_002408 | NP_002399 | 1344 |
| Sdc4 | NM_002999 | NP_002990 | 597 |
| Ralb | NM_002881 | NP_002872 | 621 |
| DGKG | NM_001346 | NP_001337 | 2376 |
| TRA2B | AK098191 | BAC05256 | 759 |
| CLIC1 | NM_001288 | NP_001279 | 726 |
| 90780 | NM_138300 | NP_612157 | 1221 |
| 5569 | NM_181839 | NP_862822 | 231 |
| 151516 | NM_152792 | NP_690005 | 1032 |
| CALD1 | AF247820 | AAF69498 | 1446 |
| DUT | AF018432 | AAB71393 | 759 |
| copa | BC038447 | AAH38447 | 3702 |
| PDCD2 | NM_144781 | NP_659005 | 687 |
| 151516 | NM_152792 | NP_690005 | 1032 |
| VGLL4 | D50911 | BAA09470 | 891 |
| APOE | NM_000041 | NP_000032 | 954 |
| 8131 | NM_012075 | NP_036207 | 1710 |
| 10988 | AK091730 | BAC03733 | 1368 |
| 9569 | NM_005685 | NP_005676 | 2835 |
| Acvrl1 | NM_000020 | NP_000011 | 1512 |
| Adcy4 | NM_139247 | NP_640340 | 3234 |
| Calcrl | NM_005795 | NP_005786 | 1386 |
| Caskin2 | NM_020753 | NP_065804 | 3609 |
| Ccbp2 | NM_001296 | NP_001287 | 1155 |
| Cldn5 | BC019290 | AAH19290 | 801 |
| 01839 | NM_001945 | NP_001936 | 627 |
| Egfl7 | NM_016215 | NP_057299 | 822 |
| Ehd4 | NM_139265 | NP_644670 | 1626 |
| Entpd1 | AJ133134 | CAB41887 | 921 |
| Epas1 | BC015869 | AAH15869 | 306 |
| Erg | NM_004449 | NP_004440 | 1389 |
| ESAM1 | NM_138961 | NP_620411 | 1173 |
| Fgd5 | BX640820 | CAE45896 | 3387 |
| Gpr116 | AL050295 | CAB43394 | 1855 |
| Hspa12b | NM_052970 | NP_443202 | 2061 |
| Icam1 | NM_000201 | NP_000192 | 1599 |
| Icam2 | NM_000873 | NP_000864 | 828 |
| Kifc1 | BC000712 | AAH00712 | 2180 |

TABLE 12-continued

GENES IN REAL TIME PCR ARRAYS

| Gene Symbol | GenBank Accession | NCBI Protein Accession | Coding DNA Length |
|---|---|---|---|
| Lats2 | NM_014572 | NP_055387 | 3267 |
| Lrrk1 | AB058693 | BAB47419 | 4112 |
| Mmrn2 | NM_024756 | NP_079032 | 2850 |
| Myo1b | AJ001381 | CAA04712 | 1310 |
| PALD | AB033100 | BAA86588 | 2586 |
| NM_023516 | BC015770 | AAH15770 | 1446 |
| 55332 | BC018435 | AAH18435 | 717 |
| CTTNBP2NL | NM_018704 | NP_061174 | 1920 |
| CENTD3 | NM_022481 | NP_071926 | 4635 |
| C1orf54 | NM_024579 | NP_078855 | 396 |
| 134265 | AK074185 | BAB85011 | 2381 |
| Npr3 | NM_000908 | NP_000899 | 1623 |
| Pltp | NM_182676 | NP_872617 | 1326 |
| Ptprb | BC051329 | AAH51329 | 2316 |
| Ptprm | NM_002845 | NP_002836 | 4359 |
| GRRP1 | BC025658 | AAH25658 | 816 |
| stard9 | AB037721 | BAA92538 | 5464 |
| Ramp2 | NM_005854 | NP_005845 | 528 |
| Rasip1 | BC042111 | AAH42111 | 1567 |
| Robo4 | AK074163 | BAB84989 | 2109 |
| Sdpr | NM_004657 | NP_004648 | 1278 |
| Slc43a3 | AP118070 | AAF22014 | 318 |
| Slc9a3r2 | U82108 | AAB53042 | 981 |
| Slco2a1 | BC041140 | AAH41140 | 2035 |
| B2M | NM_004048 | NP_004039 | 360 |
| HPRT1 | NM_000194 | NP_000185 | 657 |
| RPL13A | NM_012423 | NP_036555 | 612 |
| GAPDH | NM_002046 | NP_002037 | 1008 |
| ACTB | NM_001101 | NP_001092 | 1128 |

TABLE 13

REAL TIME PCR PRIMERS

| Gene | PrimerBank ID | Forward Primer | Reverse Primer |
|---|---|---|---|
| AKT1 | 4885061a1 | GCACAAACGAGGGGAGTACAT (SEQ ID NO: 1) | CCTCACGTTGGTCCACATC (SEQ ID NO: 2) |
| ANGPT1 | 20532340a1 | CTCGCTGCCATTCTGACTCAC (SEQ ID NO: 3) | GACAGTTGCCATCGTGTTCTG (SEQ ID NO: 4) |
| ANGPT2 | 8570647a1 | TCTTGGCCGCAGCCTATAAC (SEQ ID NO: 5) | TGCTGGACCTGATATTGCTTCT (SEQ ID NO: 6) |
| ANGPTL3 | 7656888a1 | CTTCAATGAAACGTGGGAGAACT (SEQ ID NO: 7) | GCCAGTAATCGCAACTAGATGT (SEQ ID NO: 8) |
| ANGPTL4 | 21536396a1 | TCCTGGGACGAGATGAATGTC (SEQ ID NO: 9) | CTGAGCCTTGAGTTGTGTCTG (SEQ ID NO: 10) |
| ANPEP | 4502095a1 | GCACAATCATCGCACTGTCAG (SEQ ID NO: 11) | CGCTTTACTTTGGTCCAAGGT (SEQ ID NO: 12) |
| BAI1 | 4502355a1 | GCGGCGCTACACTCTCTAC (SEQ ID NO: 13) | AGCACCTCGTCGAAGCTCT (SEQ ID NO: 14) |
| CCL11 | 4506827a1 | ATACCCCTTCAGCGACTAGAG (SEQ ID NO: 15) | GCTTTGGAGTTGGAGATTTTTGG (SEQ ID NO: 16) |
| CCL2 | 4506841a1 | CAGCCAGATGCAATCAATGCC (SEQ ID NO: 17) | TGGAATCCTGAACCCACTTCT (SEQ ID NO: 18) |
| CDH5 | 4502727a1 | GATCAAGTCAAGCGTGAGTCG (SEQ ID NO: 19) | AGCCTCTCAATGGCGAACAC (SEQ ID NO: 20) |
| COL18A1 | 13385620a1 | GCTGAACCTGAACTGGCTTTG (SEQ ID NO: 21) | GACACCGGCAATGTTCTCCTC (SEQ ID NO: 22) |
| COL4A3 | 10835113a1 | CAGCTCTGATGCCAATGAACA (SEQ ID NO: 23) | TTGCACGTTCCTCTTCCATGA (SEQ ID NO: 24) |
| dll4 | 9506545a1 | TCCAACTGCCCTTCAATTTCAC (SEQ ID NO: 25) | CTGGATGGCGATCTTGCTGA (SEQ ID NO: 26) |
| CXCL10 | 4504701a1 | GTGGCATTCAAGGAGTACCTC (SEQ ID NO: 27) | GCCTTCGATTCTGGATTCAGACA (SEQ ID NO: 28) |
| CXCL3 | 4504157a1 | CGCCCAAACCGAAGTCATAG (SEQ ID NO: 29) | GCTCCCCTTGTTCAGTATCTTT (SEQ ID NO: 30) |
| CXCL5 | 4506849a1 | GAGAGCTGCGTTGCGTTTG (SEQ ID NO: 31) | TTTCCTTGTTTCCACCGTCCA (SEQ ID NO: 32) |
| CXCL6 | 4506851a1 | AGAGCTGCGTTGCACTTGTT (SEQ ID NO: 33) | GCAGTTTACCAATCGTTTTGGGG (SEQ ID NO: 34) |

TABLE 13-continued

REAL TIME PCR PRIMERS

| Gene | PrimerBank ID | Forward Primer | Reverse Primer |
|---|---|---|---|
| CXCL9 | 4505187a1 | CCAGTAGTGAGAAAGGGTCGC (SEQ ID NO: 35) | TGGGGCAAATTGTTTAAGGTCTT (SEQ ID NO: 36) |
| TYMP | 4503445a1 | AGCTGGAGTCTATTCCTGGATT (SEQ ID NO: 37) | GGCTGCATATAGGATTCCGTC (SEQ ID NO: 38) |
| S1PR1 | 13027636a1 | CTTGCTGACCATTTGGAAAACC (SEQ ID NO: 39) | CTGTGTAGGCTACTCCTGCC (SEQ ID NO: 40) |
| EFNA1 | 33359680a1 | CGGAGAAGCTGTCTGAGAAGT (SEQ ID NO: 41) | CTGAGGACTGTGAGAGATGTAGT (SEQ ID NO: 42) |
| EFNA3 | 4826708a1 | TCTCTGGGCTACGAGTTCCAC (SEQ ID NO: 43) | ACGTTGATCTTCACATTGGGG (SEQ ID NO: 44) |
| EFNB2 | 4758250a1 | ACTGCTGGGGTGTTTTGATGG (SEQ ID NO: 45) | TGTGGGTATAGTACCAGTCCTTG (SEQ ID NO: 46) |
| EGF | 4503491a1 | AAGGTACTCTCGCAGGAAATGG (SEQ ID NO: 47) | ACATACTCTCTCTTGCCTTGACC (SEQ ID NO: 48) |
| ENG | 4557555a1 | AGCCCCACAAGTCTTGCAG (SEQ ID NO: 49) | GCTAGTGGTATATGTCACCTCGC (SEQ ID NO: 50) |
| EPHB4 | 32528301a1 | CGGCAGCCTCACTACTCAG (SEQ ID NO: 51) | TCCCATTTTGATGGCCCGAAG (SEQ ID NO: 52) |
| EREG | 4557567a1 | CTGCCTGGGTTTCCATCTTCT (SEQ ID NO: 53) | GCCATTCATGTCAGAGCTACACT (SEQ ID NO: 54) |
| FGF1 | 4503697a1 | ACACCGACGGGCTTTTATACG (SEQ ID NO: 55) | CCCATTCTTCTTGAGGCCAAC (SEQ ID NO: 56) |
| FGF2 | 15451898a1 | AGAAGAGCGACCCTCACATCA (SEQ ID NO: 57) | ACTGCCCAGTTCGTTTCAGTG (SEQ ID NO: 58) |
| FGFR3 | 4503711a1 | TCCTTGCACAACGTCACCTTT (SEQ ID NO: 59) | GCAGAGTGATGAGAAAACCCAA (SEQ ID NO: 60) |
| FIGF | 4758378a1 | ACAGAGAGTGGGTAGTGGTGA (SEQ ID NO: 61) | GTTCCTCCAAACTAGAAGCAGC (SEQ ID NO: 62) |
| FLT1 | 4503749a1 | CTGTCATGCTAATGGTGTCCC (SEQ ID NO: 63) | TGCTGCTTCCTGGTCCTAAAATA (SEQ ID NO: 64) |
| HAND2 | 12545384a1 | ATGAGTCTGGTAGGTGGTTTTCC (SEQ ID NO: 65) | CATACTCGGGGCTGTAGGACA (SEQ ID NO: 66) |
| HGF | 33859835a1 | TACAGGGGCACTGTCAATACC (SEQ ID NO: 67) | GGATACTGAGAATCCCAACGC (SEQ ID NO: 68) |
| HIF1A | 4504385a1 | GGCGCGAACGACAAGAAAAAG (SEQ ID NO: 69) | CCTTATCAAGATGCGAACTCACA (SEQ ID NO: 70) |
| HPSE | 5729873a1 | TCCTGCGTACCTGAGGTTTG (SEQ ID NO: 71) | CAACCGTAACTTCTCCTCCAC (SEQ ID NO: 72) |
| ID1 | 31317299a1 | ACGAGCAGCAGGTAAACGTG (SEQ ID NO: 73) | GAAGGTCCCTGATGTAGTCGAT (SEQ ID NO: 74) |
| ID3 | 32171182a1 | AGTCCCGAGAGGCACTCAG (SEQ ID NO: 75) | GCTCCTTTTGTCGTTGGAGATG (SEQ ID NO: 76) |
| IFNA1 | 13128950a1 | GCCTCGCCCTTTGCTTTACT (SEQ ID NO: 77) | CTGTGGGTCTCAGGGAGATCA (SEQ ID NO: 78) |
| IFNB1 | 4504603a1 | ATGACCAACAAGTGTCTCCTCC (SEQ ID NO: 79) | GCTCATGGAAAGAGCTGTAGTG (SEQ ID NO: 80) |
| IFNG | 10835171a1 | CTCTTGGCTGTTACTGCCAGG (SEQ ID NO: 81) | CTCCACACTCTTTTGGATGCT (SEQ ID NO: 82) |
| IGF1 | 11024682a1 | ATGCTCTTCAGTTCGTGTGTG (SEQ ID NO: 83) | GCACTCCCTCTACTTGCGTTC (SEQ ID NO: 84) |

TABLE 13-continued

REAL TIME PCR PRIMERS

| Gene | PrimerBank ID | Forward Primer | Reverse Primer |
|---|---|---|---|
| IL1B | 10835145a1 | CTCGCCAGTGAAATGATGGCT (SEQ ID NO: 85) | GTCGGAGATTCGTAGCTGGAT (SEQ ID NO: 86) |
| IL6 | 10834984a1 | AAATTCGGTACATCCTCGACGG (SEQ ID NO: 87) | GGAAGGTTCAGGTTGTTTTCTGC (SEQ ID NO: 88) |
| IL8 | 10834978a1 | TTTTGCCAAGGAGTGCTAAAGA (SEQ ID NO: 89) | AACCCTCTGCACCCAGTTTTC (SEQ ID NO: 90) |
| ITGAV | 4504763a1 | TCGGGACTCCTGCTACCTC (SEQ ID NO: 91) | CACGAGAAGAAACATCCGGGA (SEQ ID NO: 92) |
| ITGB3 | 4557677a1 | AGGATGACTGTGTCGTCAGAT (SEQ ID NO: 93) | GGTAGACGTGGCCTCTTTATACA (SEQ ID NO: 94) |
| JAG1 | 4557679a1 | TCGGGTCAGTTCGAGTTGGA (SEQ ID NO: 95) | AGGCACACTTTGAAGTATGTGTC (SEQ ID NO: 96) |
| KDR | 11321597a1 | GGCCCAATAATCAGAGTGGCA (SEQ ID NO: 97) | TGTCATTTCCGATCACTTTTGGA (SEQ ID NO: 98) |
| LAMA5 | 21264602a1 | CCCACCGAGGACCTTTACTG (SEQ ID NO: 99) | GGTGTGCCTTGTTGCTGTT (SEQ ID NO: 100) |
| LECT1 | 5901932a1 | GGTGGGACCTGATGACGTG (SEQ ID NO: 101) | AGCTCCCGAAATGAGGACCA (SEQ ID NO: 102) |
| LEP | 4557715a1 | GAACCCTGTGCGGATTCTTGT (SEQ ID NO: 103) | TCCATCTTGGATAAGGTCAGGAT (SEQ ID NO: 104) |
| MDK | 4505135a1 | CGCGGTCGCCAAAAAGAAAG (SEQ ID NO: 105) | CAGTCGGCTCCAAACTCCT (SEQ ID NO: 106) |
| MMP2 | 11342666a1 | CCGTCGCCCATCATCAAGTT (SEQ ID NO: 107) | CTGTCTGGGGCAGTCCAAAG (SEQ ID NO: 108) |
| MMP9 | 4826836a1 | TGGCAGAGATGCGTGGAGA (SEQ ID NO: 109) | GGCAAGTCTTCCGAGTAGTTTT (SEQ ID NO: 110) |
| Notch4 | 27894370a1 | GGGTGAGACGTGCCAGTTTC (SEQ ID NO: 111) | CTGGGTGTCAATGGAGAGGGA (SEQ ID NO: 112) |
| NRP1 | 4505457a1 | TGGGGCTCTCACAAGACCTT (SEQ ID NO: 113) | AGCTTGGGAATAGATGAAGTTGC (SEQ ID NO: 114) |
| NRP2 | 4505459a1 | GAAGGGAACATGCACTATGACA (SEQ ID NO: 115) | AGCGTTTTTACCGTGGGCTT (SEQ ID NO: 116) |
| PDGFA | 15208658a1 | CCAGCGACTCCTGGAGATAGA (SEQ ID NO: 117) | CTTCTCGGGCACATGCTTAGT (SEQ ID NO: 118) |
| PECAM1 | 21314617a1 | AACAGTGTTGACATGAAGAGCC (SEQ ID NO: 119) | TGTAAAACAGCACGTCATCCTT (SEQ ID NO: 120) |
| PGF | 20149543a1 | TGCTGCGGCGATGAGAATC (SEQ ID NO: 121) | GTCCTCCTTTCCGGCTT (SEQ ID NO: 122) |
| PLAU | 4505863a1 | GTGAGCGACTCCAAAGGCA (SEQ ID NO: 123) | GCAGTTGCACCAGTGAATGTT (SEQ ID NO: 124) |
| PLG | 4505881a1 | CAGGGGGCTTCACTGTTCAG (SEQ ID NO: 125) | GCCATTATCACACATTGTTGCTC (SEQ ID NO: 126) |
| PLXDC1 | 15011862a1 | CCTGGGCATGTGTCAGAGC (SEQ ID NO: 127) | GGTGTTGGAGAGTATTGTGTGG (SEQ ID NO: 128) |
| PROK2 | 17530787a1 | GTGACAAGGACTCCCAATGTG (SEQ ID NO: 129) | TCTTGACCCAGATACTGACAGC (SEQ ID NO: 130) |
| PTGS1 | 18104967a1 | CTCCCAGGAGTACAGCTACGA (SEQ ID NO: 131) | CCAGCAATCTGGCGAGAGA (SEQ ID NO: 132) |
| SERPINF1 | 34098938a1 | GCCCTGGTGCTACTCCTCT (SEQ ID NO: 133) | CAGCTTGTTCACGGGGACTTT (SEQ ID NO: 134) |

TABLE 13-continued

REAL TIME PCR PRIMERS

| Gene | PrimerBank ID | Forward Primer | Reverse Primer |
|---|---|---|---|
| SPHK1 | 21361088a1 | AGGCTGAAATCTCCTTCACGC (SEQ ID NO: 135) | GTCTCCAGACATGACCACCAG (SEQ ID NO: 136) |
| STAB1 | 12225240a1 | ACATCTGCTCGAACCCAAACA (SEQ ID NO: 137) | GACAGCGACATCTGGCAACA (SEQ ID NO: 138) |
| TEK | 4557869a1 | TGCCACCCTGGTTTTTACGG (SEQ ID NO: 139) | TTGGAAGCGATCACACATCTC (SEQ ID NO: 140) |
| TGFA | 4507461a1 | GGCCCTGGCTGTCCTTATC (SEQ ID NO: 141) | AGCAAGCGGTTCTTCCCTTC (SEQ ID NO: 142) |
| TGFB1 | 10863873a1 | GGCCAGATCCTGTCCAAGC (SEQ ID NO: 143) | GTGGGTTTCCACCATTAGCAC (SEQ ID NO: 144) |
| TGFB2 | 4507463a1 | CTGCATCTGGTCACGGTCG (SEQ ID NO: 145) | CCTCGGGCTCAGGATAGTCT (SEQ ID NO: 146) |
| TGFBR1 | 4759226a1 | ACGGCGTTACAGTGTTTCTG (SEQ ID NO: 147) | GCACATACAAACGGCCTATCT (SEQ ID NO: 148) |
| THBS1 | 4507485a1 | TGCCTGATGACAAGTTCCAAG (SEQ ID NO: 149) | CCAGAGTGGTCTTTCCGCTC (SEQ ID NO: 150) |
| THBS2 | 4507487a1 | ACAAAGACACGACCTTCGACC (SEQ ID NO: 151) | GACTTGCCGTCCTGCTTGA (SEQ ID NO: 152) |
| TIMP1 | 4507509a1 | CTTCTGCAATTCCGACCTCGT (SEQ ID NO: 153) | CCCTAAGGCTTGGAACCCTTT (SEQ ID NO: 154) |
| TIMP2 | 4507511a1 | AAGCGGTCAGTGAGAAGGAAG (SEQ ID NO: 155) | TCCTCTTGATAGGGTTGCCATA (SEQ ID NO: 156) |
| TIMP3 | 4507513a1 | CAACTCCGACATCGTGATCCG (SEQ ID NO: 157) | GAAGCCTCGGTACATCTTCATC (SEQ ID NO: 158) |
| TNF | 25952111a1 | ATGAGCACTGAAAGCATGATCC (SEQ ID NO: 159) | GAGGGCTGATTAGAGAGAGGTC (SEQ ID NO: 160) |
| TNFAIP2 | 26051240a1 | TCCCCGAGAGCGTCTTTCT (SEQ ID NO: 161) | ATGTCATTGGGGTAGAGGTTCT (SEQ ID NO: 162) |
| VEGFA | 30172564a1 | CAACATCACCATGCAGATTATGC (SEQ ID NO: 163) | GCTTTCGTTTTTGCCCCTTTC (SEQ ID NO: 164) |
| VEGFC | 4885653a1 | CACGGCTTATGCAAGCAAAGA (SEQ ID NO: 165) | TCCTTTCCTTAGCTGACACTTGT (SEQ ID NO: 166) |
| CD248 | 9966885a1 | TGCGAACACGAATGTGTGGA (SEQ ID NO: 167) | CAATCTGGCACTCATCTGTGTC (SEQ ID NO: 168) |
| GPR124 | 20521932a1 | TGAGCAATAACAAGATCACGGG (SEQ ID NO: 169) | TCGGAGGTGAGACAGCCAA (SEQ ID NO: 170) |
| PLXDC1 | 15011862a1 | CCTGGGCATGTGTCAGAGC (SEQ ID NO: 171) | GGTGTTGGAGAGTATTGTGTGG (SEQ ID NO: 172) |
| ANTXR1 | 14149904a1 | CGGTAGACGCCTCTTATTATGGT (SEQ ID NO: 173) | CCTTTTCCAACTTAGCACCTTCT (SEQ ID NO: 174) |
| RASD2 | 22027486a1 | CAGTGTGCCCGCCAAAAAC (SEQ ID NO: 175) | TGGGTGTGTACTGGTCCTCAA (SEQ ID NO: 176) |
| ARHGEF17 | 21361458a1 | CGACTCTGAATCCCCAGGAAC (SEQ ID NO: 177) | CCTGCGGTTGGGAGAAGATA (SEQ ID NO: 178) |
| TNS3 | 21739317a1 | GGCATTACCCCGTGAACAGT (SEQ ID NO: 179) | CACCCCGATGTCTCTGTGAT (SEQ ID NO: 180) |
| DKK3 | 27735014a1 | TGGGGTCACTGCACCAAAAT (SEQ ID NO: 181) | GAAGGTCGGCTTGCACACATA (SEQ ID NO: 182) |
| MMP11 | 5174581a1 | GAGGCCCTAAAGGTATGGAGC (SEQ ID NO: 183) | CCCTTCTCGGTGAGTCTTGG (SEQ ID NO: 184) |

TABLE 13-continued

REAL TIME PCR PRIMERS

| Gene | PrimerBank ID | Forward Primer | Reverse Primer |
|---|---|---|---|
| NID1 | 28374139a1 | CACATTGAGCCCTACACGGAG (SEQ ID NO: 185) | GCTGAGAGCATAGCGCAAGAT (SEQ ID NO: 186) |
| THY1 | 19923362a1 | TCGCTCTCCTGCTAACAGTCT (SEQ ID NO: 187) | CTCGTACTGGATGGGTGAACT (SEQ ID NO: 188) |
| CST4 | 4503109a1 | CCTCTGTGTACCCTGCTACTC (SEQ ID NO: 189) | CTTCGGTGGCCTTGTTGTACT (SEQ ID NO: 190) |
| MRC2 | 5174485a1 | CCGAAACCGGCTATTCAACCT (SEQ ID NO: 191) | CAGCGAAGATTCAGTGCTTCC (SEQ ID NO: 192) |
| TNS1 | 13624033a1 | TAGATGGGAGCCTGTATGCTAAG (SEQ ID NO: 193) | GTAGGACGTGTGGCATTAACA (SEQ ID NO: 194) |
| BMP1 | 18027738a1 | CTCTCTCGTTTCAGAAAAGAGGC (SEQ ID NO: 195) | TTCCTGAGTAACAAGGGGTCC (SEQ ID NO: 196) |
| COMT | 4502969a1 | TACTGCGAGCAGAAGGAGTG (SEQ ID NO: 197) | CCAGCGAAATCCACCATCC (SEQ ID NO: 198) |
| PTPRCAP | 5032005a1 | AGCTGGGGTCCACAGACAA (SEQ ID NO: 199) | GACGCCTCTCCACATTGCT (SEQ ID NO: 200) |
| 57722 | 10047333a1 | GCGAGCAGATCATCGGCTT (SEQ ID NO: 201) | TGCAAACTGGTATTCCACATTGT (SEQ ID NO: 202) |
| EXTL3 | 4503617a1 | CGCTCATCGCCCACTATTACC (SEQ ID NO: 203) | TGTTCAGCTCTTGGCGCTT (SEQ ID NO: 204) |
| vWF | 4507907a1 | AGCCTTGTGAAACTGAAGCAT (SEQ ID NO: 205) | GGCCATCCCAGTCCATCTG (SEQ ID NO: 206) |
| PNMT | 4505921a1 | GCAGACCGTAGCCCCAATG (SEQ ID NO: 207) | GCGTAGTTGTTGCGGAGGTA (SEQ ID NO: 208) |
| 58488 | 13477277a1 | CGGTGCCTCCAAGTGACTG (SEQ ID NO: 209) | AGGCTGAACTCCTGTGACCTT (SEQ ID NO: 210) |
| 1tbp4 | 22759983a1 | TATGCTGGTTCCCTGGCTGA (SEQ ID NO: 211) | GGCCTCATCACACTCGTTG (SEQ ID NO: 212) |
| 23001 | 16550629a1 | TCTTGCGGTGGAACAGAATAAG (SEQ ID NO: 213) | GCATAGCCCCAAGCAAAGTT (SEQ ID NO: 214) |
| 4247 | 4505163a1 | GTGCATAACCGGCCCGAATA (SEQ ID NO: 215) | AACCGGACAGAAATTCACCCC (SEQ ID NO: 216) |
| Sdc4 | 4506861a1 | GCTCTTCGTAGGCGGAGTC (SEQ ID NO: 217) | CCTCATCGTCTGGTAGGGCT (SEQ ID NO: 218) |
| ralb | 4506405a1 | GCCAACAAGAGTAAGGGCCAG (SEQ ID NO: 219) | CGTCATACATGAACTGAAGCGTC (SEQ ID NO: 220) |
| DGKG | 4503315a1 | GGTGAAGAACGGTGGGTCTC (SEQ ID NO: 221) | AATCGGCTCATGTGGGTCATA (SEQ ID NO: 222) |
| TRA2B | 21758154a1 | CCCCTGCAAAGTCTCGCTC (SEQ ID NO: 223) | AATCTCGACTGTAAGACCTGCTA (SEQ ID NO: 224) |
| CLIC1 | 14251209a1 | ACAACCGCAGGTCGAATTGTT (SEQ ID NO: 225) | GTGACTCCCTTGAGCCACA (SEQ ID NO: 226) |
| 90780 | 23510333a1 | CCAGAAAAGAAGCGAAGGAAGT (SEQ ID NO: 227) | TCCGAAGTCATCTTCAAAAGGG (SEQ ID NO: 228) |
| 5569 | 32483386a1 | GCCTTGAAATTAGCAGGTCTTGA (SEQ ID NO: 229) | CTGTAGAACTTCGTTGTGCATCT (SEQ ID NO: 230) |
| 151516 | 22758146a1 | TTCGAGAGGCCCCGTTTTC (SEQ ID NO: 231) | ATTGGCCCCATCAAAAGGTTC (SEQ ID NO: 232) |
| CALD1 | 13186201a1 | TTTGAGCGTCGCAGAGAACTT (SEQ ID NO: 233) | TGTCCCAAGGATTCTTCCTCC (SEQ ID NO: 234) |

TABLE 13-continued

REAL TIME PCR PRIMERS

| Gene | PrimerBank ID | Forward Primer | Reverse Primer |
|---|---|---|---|
| DUT | 2443580a1 | CGCCATTTCACCCAGTAAGC (SEQ ID NO: 235) | AGCCACTCTTCCATAACACCC (SEQ ID NO: 236) |
| copa | 23512328a1 | TCAGCTTTCACCCCAAAAGAC (SEQ ID NO: 237) | CACATCCGATAGTCCCATAACTG (SEQ ID NO: 238) |
| PDCD2 | 21735594a1 | CCGGCCTGCGAGTTTTTAG (SEQ ID NO: 239) | GGGGGAGGATTCTCAGAAGGT (SEQ ID NO: 240) |
| 151516 | 22758146a1 | TTCGAGAGGCCCCGTTTTC (SEQ ID NO: 241) | ATTGGCCCCATCAAAAGGTTC (SEQ ID NO: 242) |
| VGLL4 | 6633997a1 | AATATCGGCATTCTGTGCTACG (SEQ ID NO: 243) | GCAGGGTCTGTATTCTGGGT (SEQ ID NO: 244) |
| APOE | 4557325a1 | GTTGCTGGTCACATTCCTGG (SEQ ID NO: 245) | GGTAATCCCAAAAGCGACCCA (SEQ ID NO: 246) |
| 8131 | 6912302a1 | CAGCCCCATCAGCGTGATT (SEQ ID NO: 247) | GCGGCTTACTTGTCTGGGAC (SEQ ID NO: 248) |
| 10988 | 21750170a1 | AGACCCTCCCTCAGTTCCAAT (SEQ ID NO: 249) | GGGTATTCGCATTCTTGTCCTT (SEQ ID NO: 250) |
| 9569 | 15011924a1 | CTGCTCTTCAACACACGATACG (SEQ ID NO: 251) | CCCTCTCTTGACTATCCACGAT (SEQ ID NO: 252) |
| Acvrl1 | 4557243a1 | CCAACCTCCTTCGGAGCAG (SEQ ID NO: 253) | CTGTGGTGCAGTCACTGTCC (SEQ ID NO: 254) |
| Adcy4 | 24497587a1 | AGCTGACCTCAGACCCGAG (SEQ ID NO: 255) | CATACGCCGTGAAGATGACGA (SEQ ID NO: 256) |
| Calcr1 | 5031621a1 | AAGACCCCATTCAACAAGCAG (SEQ ID NO: 257) | CCAGTTTCCATCTTGGTCACAG (SEQ ID NO: 258) |
| Caskin2 | 24638431a1 | CTGATCCTCGCCGTCAAGAAT (SEQ ID NO: 259) | GTTCACGTTGAGCCTCTTTGT (SEQ ID NO: 260) |
| Ccbp2 | 13929467a1 | CTGAGGATGCCGATTCTGAGA (SEQ ID NO: 261) | TAACGGAGCAAGACCATGAGA (SEQ ID NO: 262) |
| Cldn5 | 17939486a1 | CTCTGCTGGTTCGCCAACAT (SEQ ID NO: 263) | CAGCTCGTACTTCTGCGACA (SEQ ID NO: 264) |
| 01839 | 4503413a1 | CCCTCCCACTGTATCCACG (SEQ ID NO: 265) | AGTGACTCTCAAAAGGTCCAGA (SEQ ID NO: 266) |
| Egfl7 | 7705889a1 | CAGCACCTACCGAACCATCTA (SEQ ID NO: 267) | CCCTCCTAGCACTGCATTCAT (SEQ ID NO: 268) |
| Ehd4 | 21264315a1 | CTGCTCTTTGACGCTCACAAG (SEQ ID NO: 269) | GTCGGCCTTATTCAGCACG (SEQ ID NO: 270) |
| Entpd1 | 4741547a1 | CAACTATCTGCTGGGCAAATTCA (SEQ ID NO: 271) | GGCAGGTCTGGATTGAGTTATAC (SEQ ID NO: 272) |
| Epas1 | 16198412a1 | TTTCACACGGCACATTTGGAC (SEQ ID NO: 273) | GTGGACGGGGTCACTATACC (SEQ ID NO: 274) |
| Erg | 4758300a1 | CCAGCAGCTCATATCAAGGAAG (SEQ ID NO: 275) | GTTCCGTAGGCACACTCAAAC (SEQ ID NO: 276) |
| ESAM1 | 20452464a1 | CCCCTGGTGACCAACTTGC (SEQ ID NO: 277) | TGGGATGAAGACACCTCCCC (SEQ ID NO: 278) |
| Fgd5 | 34365081a1 | AGCCCCTATGAGTTCTTCCCA (SEQ ID NO: 279) | GTGCCTGCTCTGATTCTAAACC (SEQ ID NO: 280) |
| Gpr116 | 4886491a1 | TGCACTGAACTGGAATTACGAG (SEQ ID NO: 281) | CAGCCGTAGGACTTTTTGTGG (SEQ ID NO: 282) |
| Hspa12b | 31317303a1 | CACCCTCGCAGTCTCCAAAA (SEQ ID NO: 283) | GAAAGCATAGCCACTAGACGTG (SEQ ID NO: 284) |

TABLE 13-continued

REAL TIME PCR PRIMERS

| Gene | PrimerBank ID | Forward Primer | Reverse Primer |
|---|---|---|---|
| Icam1 | 4557878a1 | TCTGTGTCCCCCTCAAAAGTC (SEQ ID NO: 285) | GGGGTCTCTATGCCCAACAA (SEQ ID NO: 286) |
| Icam2 | 4504557a1 | CGGATGAGAAGGTATTCGAGGT (SEQ ID NO: 287) | CACCCACTTCAGGCTGGTTAC (SEQ ID NO: 288) |
| Kifc1 | 33875771a1 | GAGCCGTGCGAGTTCTCTAC (SEQ ID NO: 289) | GGCCTTAATCAGAGGTCTCTTCA (SEQ ID NO: 290) |
| Lats2 | 18959200a1 | ACTTTTCCTGCCACGACTTATTC (SEQ ID NO: 291) | ATCCAGGGAAGTGTCACTGTT (SEQ ID NO: 292) |
| Lrrk1 | 14017797a1 | GCCCGACAACGACATCAAG (SEQ ID NO: 293) | GCCAAATAGGGTCGAGGAAGTA (SEQ ID NO: 294) |
| Mmrn2 | 13376091a1 | GGACCCCGTTGGACGTAAC (SEQ ID NO: 295) | CTTGACCTGGTACACTGGCTT (SEQ ID NO: 296) |
| Myo1b | 2764617a1 | TGGCCTCATTGGAAAGGACC (SEQ ID NO: 297) | CCAGGCGTTGCTTCCTCAG (SEQ ID NO: 298) |
| PALD | 20521820a1 | GGCTGCTGGCAGACTATGG (SEQ ID NO: 299) | TGGACTTGGCCTTGCTGTTAT (SEQ ID NO: 300) |
| NM_023516 | 16041779a1 | GCTGACCCTGCTTGGCTTAT (SEQ ID NO: 301) | CCCTCGCCATACCGATGTATTA (SEQ ID NO: 302) |
| 55332 | 22450862a1 | TGCTTCCTGAGGGGAATGG (SEQ ID NO: 303) | ATCGTGGCTGCACCAAGAAA (SEQ ID NO: 304) |
| CTTNBP2NL | 24308179a1 | AGCCTGAACTCCTGACACTAT (SEQ ID NO: 305) | TGCTTTTCGCCATCATTTTTCTC (SEQ ID NO: 306) |
| CENTD3 | 21264337a1 | GTATGCAGACACGTTCCGAC (SEQ ID NO: 307) | CAGGCGTAGAATGCGTTTCC (SEQ ID NO: 308) |
| C1orf54 | 13375758a1 | ACAGTCACCCCCAGTTATGAT (SEQ ID NO: 309) | ATCTGGACTAGGTTCCGTTGT (SEQ ID NO: 310) |
| 134265 | 18676718a1 | TGTGGGTGACAACTGTTCTACC (SEQ ID NO: 311) | AGAAGCCAATGATACGGGTGAT (SEQ ID NO: 312) |
| Npr3 | 4505441a1 | TGCTCACTTTCTCCCCGTG (SEQ ID NO: 313) | GGGCAGTAACACCAGCACC (SEQ ID NO: 314) |
| Pltp | 33356541a1 | TCACAGAGCTGCAACTGACAT (SEQ ID NO: 315) | AGGCATTGGTGATTTGAAGCA (SEQ ID NO: 316) |
| Ptprb | 30410925a1 | CATGGTGATTCTTACCTGCTTGA (SEQ ID NO: 317) | CCCACGACCACTTTCTCATTTT (SEQ ID NO: 318) |
| Ptprm | 18860904a1 | TCCAGCAAGAGTAATTCTCCTCC (SEQ ID NO: 319) | GTACGTGTTGGGTCTCCAGATA (SEQ ID NO: 320) |
| GRRP1 | 19343581a1 | TCAAGACGCACCAGGTGATAG (SEQ ID NO: 321) | CGGTAGAAGATGAGGGAATCAGG (SEQ ID NO: 322) |
| stard9 | 7242955a1 | CTCATGCTTATTCCTCCCATTCC (SEQ ID NO: 323) | AGGGTGGGTGGATAGTATGTG (SEQ ID NO: 324) |
| Ramp2 | 5032021a1 | CTGGGCGCTGTCCTGAATC (SEQ ID NO: 325) | CAATCTCGCAGGGTGCTATAAG (SEQ ID NO: 326) |
| Rasip1 | 27469793a1 | TCTGGTGAACGGAAGGAGG (SEQ ID NO: 327) | CGAAGAAGACTTGACAGAGGC (SEQ ID NO: 328) |
| Robo4 | 18676674a1 | GTGGGTGAGCAGTTTACTCTG (SEQ ID NO: 329) | GCCAGGGGTTTCCCATCTTTC (SEQ ID NO: 330) |
| Sdpr | 4759082a1 | CATCCGGGACAACTCACAGG (SEQ ID NO: 331) | CTCCAAACTGATCTGTCGCTG (SEQ ID NO: 332) |
| Slc43a3 | 6650786a1 | TCAGCCCCGAGGATGGTTT (SEQ ID NO: 333) | AAGGCTAAGTGCAAGGAGACA (SEQ ID NO: 334) |

TABLE 13-continued

REAL TIME PCR PRIMERS

| Gene | PrimerBank ID | Forward Primer | Reverse Primer |
|---|---|---|---|
| Slc9a3r2 | 2047328a1 | GCTCCGAAGCTGGCAAGAA (SEQ ID NO: 335) | GGGACTTGTCACTATGCAGGTT (SEQ ID NO: 336) |
| Slco2a1 | 26996627a1 | GGGCAGCGACACCTCTACTA (SEQ ID NO: 337) | TGGAAATGAGACCCGATGAAGAA (SEQ ID NO: 338) |
| B2M | 4757826a1 | GGCTATCCAGCGTACTCCAAA (SEQ ID NO: 339) | CGGCAGGCATACTCATCTTTTT (SEQ ID NO: 340) |
| HPRT1 | 4504483a1 | CCTGGCGTCGTGATTAGTGAT (SEQ ID NO: 341) | AGACGTTCAGTCCTGTCCATAA (SEQ ID NO: 342) |
| RPL13A | 6912634a1 | CGAGGTTGGCTGGAAGTACC (SEQ ID NO: 343) | CTTCTCGGCCTGTTTCCGTAG (SEQ ID NO: 344) |
| GAPDH | 7669492a1 | ATGGGGAAGGTGAAGGTCG (SEQ ID NO: 345) | GGGGTCATTGATGGCAACAATA (SEQ ID NO: 346) |
| ACTB | 4501885a1 | CATGTACGTTGCTATCCAGGC (SEQ ID NO: 347) | CTCCTTAATGTCACGCACGAT (SEQ ID NO: 348) |

TABLE 14

EFFECTS OF ANTIANGIOGENIC SMs ON ANGIOGENEIS GENE EXPRESSION

| NSC: | 19630 | 122567 | 150117 | 259969 | 292222 | 292596 |
|---|---|---|---|---|---|---|
| AKT1 | 0.1 | −1.6 | 1.6 | −1.4 | 0.7 | −0.8 |
| ANGPT1 | −0.5 | 1.6 | 1.7 | 1.4 | 0.9 | 2.2 |
| ANGPT2 | −1.8 | −0.9 | −1.2 | 0.9 | −1.3 | 0.8 |
| ANGPTL3 | −5.0 | −1.7 | 1.8 | 3.6 | 0.6 | 1.0 |
| ANGPTL4 | −0.2 | −0.4 | −4.0 | 1.5 | 1.3 | −3.2 |
| ANPEP | −0.4 | −1.2 | −1.7 | 0.2 | −0.6 | 0.8 |
| BAL1 | −0.9 | 0.2 | 0.8 | 0.4 | 0.2 | 1.7 |
| CCL11 | −0.3 | 0.6 | 0.7 | 0.0 | 0.2 | 2.1 |
| CCL2 | 2.3 | 2.5 | 0.9 | 3.6 | 0.9 | 2.4 |
| CDH5 | −0.2 | −1.9 | −1.6 | −1.6 | −0.1 | −0.2 |
| COL18A1 | 0.4 | 1.6 | 0.8 | 1.9 | 1.2 | 2.3 |
| COL4A3 | 0.1 | 1.9 | 2.4 | 3.2 | 2.0 | 1.9 |
| DLL4 | −4.5 | −8.7 | 5.5 | −4.1 | −2.2 | −6.6 |
| CXCL10 | 4.7 | 3.7 | −1.7 | 2.8 | 0.8 | 2.5 |
| CXCL3 | 12.1 | 4.0 | 0.8 | 11.6 | 5.0 | −3.8 |
| CXCL5 | 4.8 | 4.3 | −3.5 | 10.2 | 3.4 | 5.6 |
| CXCL6 | −0.5 | 1.1 | 1.2 | 1.0 | 0.4 | 2.2 |
| CXCL9 | −1.0 | 1.6 | 1.2 | 0.5 | 0.4 | 1.5 |
| TYMP | 0.3 | −0.3 | −1.1 | 0.1 | −0.1 | −5.5 |
| S1PR1 | −2.6 | −0.7 | −1.9 | −0.3 | −0.3 | 0.2 |
| EFNA1 | 3.7 | −0.3 | 0.4 | 7.8 | 0.9 | 3.1 |
| EFNA3 | −0.4 | −0.4 | −1.8 | 0.3 | 0.1 | 0.5 |
| EFNB2 | −1.9 | −4.0 | 0.4 | −6.6 | −2.2 | −3.4 |
| EGF | −1.0 | −0.3 | −2.3 | 0.2 | 2.8 | 2.2 |
| ENG | 0.1 | −1.7 | −0.1 | −0.7 | −0.9 | −0.3 |
| EPHB4 | −0.8 | −0.5 | −1.2 | 0.3 | −0.5 | 0.9 |
| EREG | 7.6 | 1.9 | −2.4 | 9.3 | 5.0 | 9.6 |
| FGF1 | −3.0 | 1.9 | −3.8 | 5.7 | −1.4 | 4.8 |
| FGF2 | 1.7 | −0.7 | 0.0 | 2.5 | −0.6 | 2.5 |
| FGFR3 | −0.2 | 1.2 | 1.0 | 1.2 | 0.8 | 2.2 |
| FIGF | −3.2 | −0.1 | 2.4 | 0.2 | 0.1 | 1.7 |
| FLT1 | −2.1 | −4.4 | −0.5 | −0.7 | −0.2 | −1.9 |
| HAND2 | −0.5 | 0.4 | 1.5 | 1.4 | 1.0 | 1.7 |
| HGF | −0.3 | 1.3 | 1.5 | 1.5 | 1.3 | 2.2 |
| HIF1A | −1.7 | −3.1 | −1.8 | 0.7 | −0.7 | −2.1 |
| HPSE | 0.6 | −8.3 | −0.2 | 2.6 | 1.6 | −0.3 |
| ID1 | 1.0 | −0.2 | 0.3 | 1.5 | 0.0 | 4.0 |
| ID3 | 0.4 | −0.3 | 0.5 | 2.5 | −0.2 | 1.0 |
| IFNA1 | 0.4 | 1.1 | 1.9 | 1.1 | 0.8 | 2.2 |
| IFNB1 | −0.4 | 1.2 | 2.1 | 1.6 | 1.1 | 2.6 |
| IFNG | 4.7 | 8.3 | −1.9 | 6.0 | 3.1 | 6.5 |
| IGF1 | 3.6 | −0.1 | −0.2 | −2.6 | 6.0 | 0.6 |
| IL1B | 0.2 | −0.1 | 9.5 | 1.3 | 4.3 | −4.1 |
| B2M | 0.0 | 0.1 | 2.8 | 1.2 | −0.4 | −2.0 |
| HPRT1 | 0.8 | 0.0 | −0.4 | 0.6 | 0.3 | −0.5 |
| RPL13A | −0.2 | 0.7 | −0.8 | 1.2 | 0.7 | 1.9 |
| GADPH | 0.1 | −0.7 | −1.3 | −1.0 | −0.1 | 0.3 |
| ACTB | 0.1 | −1.0 | −0.9 | −2.5 | −0.8 | 0.0 |
| IL6 | 3.5 | 14.4 | 2.2 | 9.4 | 3.0 | 3.7 |
| IL8 | 3.0 | 7.4 | 6.0 | 11.3 | 13.9 | 5.1 |
| ITGAV | −0.3 | −2.7 | −1.8 | −0.9 | 1.2 | −0.9 |
| ITGB3 | −0.9 | −1.4 | −1.4 | −2.9 | 2.5 | −1.8 |
| JAG1 | −1.2 | 0.6 | 0.3 | 1.7 | 1.6 | 0.5 |
| KDR | −2.7 | −2.3 | −2.1 | −0.5 | −1.2 | −1.8 |
| LAMAS5 | −0.8 | −1.1 | −2.2 | −0.8 | −0.4 | −0.3 |
| LECT1 | −0.4 | 0.3 | −0.2 | −8.0 | 1.4 | 1.4 |
| LEP | −4.5 | 0.2 | −0.2 | 0.8 | −0.6 | 2.6 |
| MDK | −1.1 | −0.9 | −1.5 | −1.0 | 0.8 | −1.5 |
| MMP2 | 0.5 | 0.3 | −0.6 | −0.1 | 2.8 | 1.1 |
| MMP9 | 0.3 | 0.9 | −0.3 | 4.3 | 3.3 | 1.8 |
| Notch4 | −1.8 | −1.1 | −0.7 | −0.3 | −0.4 | −0.6 |
| NRP1 | −0.5 | −3.0 | −2.0 | −2.6 | 0.8 | −2.3 |
| NRP2 | −2.2 | −4.3 | −3.2 | −3.5 | 1.0 | −3.2 |
| PDGFA | −0.7 | −1.7 | −0.9 | 1.1 | 1.6 | 4.0 |
| PECAM1 | −2.6 | −2.7 | −2.5 | −3.0 | −0.7 | −1.8 |
| PGF | −2.4 | −4.9 | −1.6 | −7.2 | 0.6 | −1.7 |
| PLAU | 0.1 | −0.1 | 0.0 | 3.8 | 2.7 | −0.2 |
| PLG | −2.7 | −1.5 | −3.9 | −1.0 | −0.7 | −0.4 |
| PLXDC1 | −4.0 | 0.7 | −3.2 | 2.3 | −0.1 | 0.3 |
| PROK2 | −1.3 | 1.3 | 0.7 | 2.2 | 1.9 | 2.0 |
| PTGS1 | −2.4 | 0.8 | 0.3 | 2.9 | 2.0 | 1.1 |
| SERPINF1 | −0.8 | 0.2 | 1.5 | 6.5 | 2.3 | 0.7 |
| SPHK1 | −0.5 | 0.9 | 1.2 | 3.2 | 2.0 | 1.8 |
| STAB1 | −1.0 | −1.7 | −0.9 | 0.5 | 0.2 | −0.5 |
| TEK | −0.4 | 0.3 | 0.7 | 1.6 | 2.0 | 1.3 |
| TGFA | 1.1 | 2.0 | 5.3 | 8.7 | −3.4 | 8.9 |
| TGFB1 | −1.3 | −1.2 | −1.3 | 0.3 | 1.1 | −0.8 |
| TGFB2 | −0.5 | 1.2 | 1.6 | 1.3 | 1.9 | 2.1 |
| TGFBR1 | −0.1 | 1.2 | 1.2 | 1.1 | 1.8 | 1.4 |
| THBS1 | 0.5 | 0.1 | −0.6 | −0.1 | 1.1 | −0.1 |
| THBS2 | −0.6 | 1.2 | 0.9 | 2.6 | 1.9 | 1.1 |
| TIMP1 | −0.8 | −1.4 | −0.7 | 2.5 | 1.6 | 1.4 |
| TIMP2 | −0.9 | −1.4 | −0.8 | 0.0 | 1.1 | 0.4 |
| TIMP3 | 0.7 | −4.3 | −2.7 | −0.6 | −0.4 | −1.2 |
| TNF | −0.6 | −0.2 | 2.4 | 9.3 | 1.0 | 6.1 |
| TNFAIP2 | 0.2 | −1.0 | −0.6 | 4.6 | 0.6 | −0.2 |

TABLE 14-continued

EFFECTS OF ANTIANGIOGENIC SMs ON ANGIOGENEIS GENE EXPRESSION

| NSC: | 19630 | 122567 | 150117 | 259969 | 292222 | 292596 |
|---|---|---|---|---|---|---|
| TNFAIP2 | −0.4 | −1.1 | 2.7 | <u>4.7</u> | 0.2 | −0.1 |
| VEGFA | 4.2 | 4.9 | −0.3 | <u>5.7</u> | 3.2 | 0.4 |
| VEGFC | 0.1 | 1.8 | <u>2.0</u> | 1.9 | 2.7 | 1.6 |
| ROBO4 | 0.1 | 0.0 | −0.2 | −4.1 | 1.1 | −1.2 |
| EphB1 | 0.0 | 0.8 | 0.7 | 0.6 | 0.9 | 0.4 |
| B2M | −0.1 | −0.2 | −1.2 | 1.5 | 1.3 | −1.6 |
| HPRT1 | 0.9 | 0.0 | 0.6 | −0.5 | 1.4 | 0.1 |
| RPL13A | 0.3 | 1.2 | 0.1 | 0.7 | 1.7 | 1.5 |
| GADPH | −0.3 | −0.8 | −0.1 | 0.0 | 1.4 | 0.8 |
| ACTB | −0.3 | −1.0 | −0.6 | −2.2 | −6.3 | −0.4 |
| CD248 | 1.3 | 1.2 | −0.4 | 0.6 | 1.3 | 0.2 |
| GPCR124 | −1.7 | <u>−3.7</u> | −2.9 | <u>−4.6</u> | <u>−1.9</u> | −6.7 |
| PLXDC1 | −5.7 | −1.7 | −0.6 | <u>−2.4</u> | 0.3 | 0.2 |
| ANTXR1 | −0.3 | <u>−3.5</u> | −4.2 | −1.4 | −0.2 | −2.1 |
| RASD2 | 0.9 | 0.5 | −0.1 | 0.5 | 0.3 | −0.5 |
| ARHGEF17 | 0.2 | −5.0 | −2.0 | −0.8 | −0.9 | −1.6 |
| TNS3 | −1.8 | <u>2.0</u> | 0.6 | <u>−8.0</u> | 0.5 | 1.3 |
| DKK3 | −1.5 | −1.9 | <u>−3.3</u> | −2.7 | −1.1 | −0.4 |
| MMP11 | 0.8 | 1.3 | −0.2 | 0.1 | 0.1 | −0.3 |
| NID1 | −2.6 | <u>−6.3</u> | <u>−5.2</u> | <u>−3.6</u> | −2.5 | <u>−3.6</u> |
| THY1 | <u>−11.3</u> | <u>−9.4</u> | <u>−12.7</u> | <u>−3.0</u> | −8.0 | −5.8 |
| CST4 | 0.8 | 1.3 | −0.1 | 0.4 | 0.8 | 0.3 |
| MRC2 | 1.6 | 0.7 | −0.7 | −0.6 | 0.6 | −0.5 |
| TNS1 | 0.6 | 0.0 | −0.9 | −0.3 | −0.3 | −0.5 |
| BMP1 | 0.5 | 0.9 | −0.4 | −0.6 | 0.4 | −0.4 |
| COMT | −0.7 | −1.5 | −1.0 | −1.7 | −0.2 | −0.7 |
| PTPRCAP | 0.4 | 0.0 | 0.2 | 0.9 | 0.1 | −0.5 |
| 57722 | 0.2 | 0.1 | −0.9 | −0.1 | 0.0 | −0.2 |
| EXTL3 | 1.0 | 0.3 | 0.0 | 0.4 | 0.8 | −0.5 |
| Vwf | −1.8 | −3.5 | <u>−3.7</u> | <u>−5.4</u> | −3.3 | −2.6 |
| PNMT | 0.7 | 1.1 | −0.4 | −0.1 | 0.1 | −0.7 |
| 58488 | 1.2 | 1.5 | 0.3 | 0.4 | 1.0 | 0.2 |
| itbp4 | −0.8 | −1.9 | −2.5 | −1.7 | 0.1 | −1.5 |
| 23001 | 0.4 | −0.5 | −1.0 | 0.3 | −0.8 | 0.1 |
| 4247 | 1.0 | 0.3 | −0.1 | 0.2 | 0.5 | −0.3 |
| Sdc4 | 2.2 | 0.4 | 0.2 | <u>4.0</u> | 0.7 | 1.4 |
| ralb | 0.1 | 0.3 | −0.7 | 0.7 | −0.4 | −0.5 |
| DGKG | 5.4 | 2.0 | 3.4 | <u>6.1</u> | 2.9 | 1.8 |
| TRA2B | 1.5 | −1.6 | −0.2 | 0.6 | −0.6 | 0.9 |
| CLIC1 | −0.1 | 0.9 | 0.0 | <u>1.8</u> | 6.6 | 0.6 |
| 90780 | −1.2 | −1.9 | −1.4 | −2.4 | 0.1 | −0.8 |
| 5569 | −3.0 | 0.8 | −0.1 | <u>4.6</u> | 1.5 | 0.1 |
| 151516 | 1.2 | 1.1 | 0.0 | 0.5 | 0.7 | 0.3 |
| CALD1 | 1.7 | <u>2.3</u> | 1.1 | −0.6 | 0.6 | 1.6 |
| DUT | −0.8 | −1.8 | −0.2 | −1.9 | −0.4 | −1.2 |
| copa | 0.4 | 0.1 | 0.0 | −2.1 | 0.2 | −0.5 |
| PDCD2 | 0.5 | −0.4 | −0.9 | <u>−1.7</u> | 0.2 | −1.1 |
| 151516 | 0.9 | 1.3 | 0.0 | 0.5 | 0.7 | 0.3 |
| VGLL4 | −1.3 | <u>−3.5</u> | −3.5 | <u>1.3</u> | −0.8 | <u>−2.8</u> |
| APOE | 3.3 | 0.8 | −1.0 | 0.8 | −2.2 | 5.1 |
| 8131 | 0.6 | 0.1 | −0.5 | −0.2 | 0.1 | 0.3 |
| 10988 | 2.5 | 1.2 | 0.8 | 0.3 | 1.0 | 0.9 |
| 9569 | −2.3 | −2.2 | −4.2 | −1.7 | 0.2 | <u>−2.0</u> |
| B2M | −1.4 | −0.2 | −0.7 | 0.5 | 0.0 | −0.4 |
| HPRT1 | 0.2 | −0.6 | 1.1 | 0.8 | 0.2 | 0.4 |
| RPL13A | 1.0 | 0.9 | 0.6 | 0.0 | 0.3 | 1.1 |
| GADPH | 0.1 | −0.7 | −0.5 | −1.7 | −0.1 | −0.3 |
| ACTB | −0.9 | −0.5 | −0.5 | −2.2 | −0.9 | −0.9 |
| Acvrl1 | −0.6 | −1.3 | −1.2 | <u>−1.9</u> | 0.0 | −1.6 |
| Adcy4 | 0.0 | −0.4 | −0.5 | −0.6 | −0.4 | 4.3 |
| Calcrl | <u>−4.3</u> | <u>−4.0</u> | −5.4 | −2.9 | −1.1 | <u>−4.3</u> |
| Caskin2 | <u>−2.8</u> | −2.3 | <u>−2.7</u> | <u>−2.3</u> | −6.7 | <u>−2.3</u> |
| Ccbp2 | −0.1 | 1.4 | 0.4 | 5.6 | 0.4 | 0.0 |
| Cldn5 | 0.6 | 0.0 | 0.1 | 0.4 | −0.1 | −0.6 |
| 1839 | −1.2 | 1.0 | 0.9 | −4.2 | −0.1 | −0.3 |
| Egfl7 | <u>−3.8</u> | −2.6 | <u>−3.3</u> | −2.3 | −1.2 | <u>−3.3</u> |
| Ehd4 | −1.1 | −0.8 | −0.6 | −0.7 | −1.4 | −1.0 |
| Entpd1 | −4.9 | −0.3 | <u>−8.9</u> | −5.6 | −5.5 | <u>−8.3</u> |
| Epas1 | 1.8 | 0.9 | 0.4 | 1.5 | −1.7 | 0.3 |
| Erg | −1.6 | <u>2.4</u> | −3.2 | −3.9 | 3.7 | −6.4 |
| ESAM1 | <u>−3.3</u> | −2.9 | −2.6 | <u>−1.6</u> | −1.1 | −2.0 |
| Fgd5 | −1.6 | −1.5 | −1.2 | −0.8 | −0.8 | −1.0 |
| Grp116 | <u>−1.9</u> | <u>−2.3</u> | <u>−3.1</u> | <u>−5.5</u> | −4.4 | <u>−3.1</u> |
| Hspa12b | <u>−4.6</u> | −3.4 | <u>−3.5</u> | −10.2 | −2.2 | <u>−3.3</u> |
| Icam1 | 0.1 | 0.0 | 0.6 | <u>2.8</u> | 0.5 | 0.5 |
| Icam2 | 0.4 | 0.1 | 0.0 | 7.5 | 0.1 | −0.4 |
| Kifc1 | 3.4 | 1.1 | −0.1 | −4.8 | 0.5 | 1.6 |
| Lasts2 | −0.1 | 4.8 | 0.3 | 1.5 | 0.1 | 0.4 |
| Lrrk1 | −2.9 | −0.5 | −1.8 | 0.3 | −0.1 | −1.5 |
| Mmm2 | −2.4 | <u>−3.5</u> | −3.4 | −7.5 | −1.0 | <u>−2.4</u> |
| Myo1b | <u>−2.3</u> | −2.9 | −2.7 | <u>−3.0</u> | −1.5 | <u>−2.0</u> |
| PALD | −1.1 | −0.5 | −1.7 | −1.3 | 1.8 | −1.9 |
| NM_023516 | 0.5 | 0.2 | 0.6 | 0.9 | 0.4 | 0.2 |
| 55332 | −1.1 | −1.0 | −1.7 | 0.1 | 2.4 | −8.6 |
| CTTNBP2NL | <u>−2.3</u> | −0.9 | <u>−2.3</u> | −1.0 | 0.2 | −3.4 |
| CENTD3 | 0.6 | 1.1 | −0.2 | −1.0 | −0.5 | 0.1 |
| C1orf54 | −4.8 | −3.4 | −1.3 | <u>−6.1</u> | −0.1 | −2.2 |
| 134265 | −1.6 | −0.2 | −1.0 | −0.6 | −1.3 | −1.6 |
| Npr3 | 8.3 | 1.5 | 0.5 | <u>2.7</u> | 0.9 | 0.7 |
| Pltp | 0.9 | 1.5 | 0.9 | 1.4 | 0.4 | 0.5 |
| Ptprb | <u>−1.6</u> | 0.5 | −2.6 | −0.1 | 0.3 | −1.9 |
| Ptprm | −1.2 | −0.4 | −1.4 | 1.7 | −0.1 | −0.8 |
| GRRP1 | 0.0 | −0.3 | 0.0 | 0.6 | 0.1 | 0.2 |
| stard9 | −0.7 | 0.5 | 0.1 | 0.0 | 0.8 | −0.9 |
| RAMP2 | <u>−4.8</u> | −5.8 | <u>−4.4</u> | <u>−5.9</u> | −0.6 | −5.0 |
| Rasip1 | 3.1 | −1.2 | −1.7 | −1.1 | −0.3 | −0.5 |
| Robo4 | 0.3 | 1.2 | −0.3 | 0.3 | 0.0 | 0.2 |
| Sdpr | −0.1 | 1.6 | 0.0 | 0.9 | −4.9 | 0.8 |
| Slc43a3 | −0.8 | 1.8 | 0.0 | 0.2 | 1.0 | 0.6 |
| Slc9a3r2 | −0.5 | −1.9 | <u>−2.6</u> | −0.8 | <u>−2.4</u> | −4.4 |
| Slco2a1 | <u>−2.5</u> | −0.6 | −2.9 | −2.4 | <u>−5.3</u> | −1.0 |
| B2M | −0.9 | 0.3 | −0.8 | 0.8 | 0.6 | −0.8 |
| HPRT1 | 2.0 | −0.2 | 0.4 | 0.5 | 0.4 | 0.1 |
| RPL13A | 0.4 | 1.3 | 0.2 | 0.0 | 1.2 | 0.6 |
| GADPH | −1.6 | −2.0 | −0.5 | −2.1 | −0.2 | 0.4 |
| ACTB | −1.6 | −0.1 | −0.2 | 0.4 | −0.6 | −0.1 |

Log2 fold-change of gene expression. Fold-changes with P ≤ 0.001 are underlined.

Clustering Analysis of Gene Expression Data

It is well known that tumors become resistant to antiangiogenic therapy (Bergers and Hanahan, *Nature Reviews: Cancer*, 8:592-603, 2008). Tumor angiogenesis involves multiple pathways. Current antiangiogenic drugs (such as AVASTIN®) successfully inhibit one pathway and are followed by activation of alternative pathways which resume the angiogenesis process within the tumor. A multitargeted strategy that inhibits multiple angiogenesis pathways is expected to more successfully avoid drug resistance.

To that end, clustering analysis was performed with the gene expression data to identify drugs which inhibit angiogenesis, and by extension tumor growth, by targeting different sets of genes and therefore different angiogenesis pathways.

Combinations of drugs which effect distant gene sets in the clustering analysis could potentially target different angiogenesis pathways and therefore be more efficient antiangiogenic regimens. Several potential drug combinations emerge from this clustering analysis, such as NSC 259969+NSC 150117.

In view of the many possible embodiments to which the principles of our invention may be applied, it should be recognized that the illustrated embodiments are only examples and should not be taken as a limitation on the scope of the invention. Rather, the scope of the invention is defined by the following claims. We therefore claim as our invention all that comes within the scope and spirit of these claims.

The invention claimed is:

1. A method of inhibiting endothelial cell tube formation in a subject, comprising administering to the subject an effective amount of a composition comprising 2-benzylidene-3-(cyclohexylamino)-3H-inden-1-one chloride (NSC 150117), or a pharmaceutically acceptable salt thereof, thereby inhibiting endothelial cell tube formation in the subject.

2. The method of claim 1, wherein the composition further comprises [4-[(4-arsonophenyl)methyl]phenyl]arsonic acid (NSC 48300), or a pharmaceutically-acceptable salt thereof.

3. The method of claim 1, wherein the composition is administered topically, intravenously, orally, parenterally, or as an implant.

4. The method of claim 1, further comprising administering to the subject an inhibitor of bFGF, FGF, or VEGF.

* * * * *

SEQUENCE LISTING

<160> NUMBER OF SEQ ID NOS: 348

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
gcacaaacga ggggagtaca t                                              21

<210> SEQ ID NO 2
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 2
cctcacgttg gtccacatc                                                 19

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
ctcgctgcca ttctgactca c                                              21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 4
gacagttgcc atcgtgttct g                                              21

<210> SEQ ID NO 5
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 5
tcttggccgc agcctataac                                                20

<210> SEQ ID NO 6
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 6
tgctggacct gatattgctt ct                                             22

<210> SEQ ID NO 7
<211> LENGTH: 23
<212> TYPE: DNA
<213> ORGANISM: Artificial sequence

```
<220> FEATURE:
<223> OTHER INFORMATION: Synthetic oligonucleotide

<400> SEQUENCE: 7
cttcaatgaa acgtgggaga act                                             23

<210> SEQ ID NO 8
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 8
gccagtaatc gcaactagat gt                                              22

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 9
tcctgggacg agatgaatgt c                                               21

<210> SEQ ID NO 10
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 10
ctgagccttg agttgtgtct g                                               21

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11
gcacaatcat cgcactgtca g                                               21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
cgctttactt tggtccaagg t                                               21

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
gcggcgctac actctctac                                                  19
```

```
<210> SEQ ID NO 14
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 14
agcacctcgt cgaagctct                                                      19

<210> SEQ ID NO 15
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 15
ataccccttc agcgactaga g                                                   21

<210> SEQ ID NO 16
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 16
gctttggagt tggagatttt tgg                                                 23

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
cagccagatg caatcaatgc c                                                   21

<210> SEQ ID NO 18
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 18
tggaatcctg aacccacttc t                                                   21

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
gatcaagtca agcgtgagtc g                                                   21

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 20
agcctctcaa tggcgaacac                                              20

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
gctgaacctg aactggcttt g                                            21

<210> SEQ ID NO 22
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 22
gacaccggca atgttctcct c                                            21

<210> SEQ ID NO 23
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 23
cagctctgat gccaatgaac a                                            21

<210> SEQ ID NO 24
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 24
ttgcacgttc ctcttccatg a                                            21

<210> SEQ ID NO 25
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 25
tccaactgcc cttcaatttc ac                                           22

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ctggatggcg atcttgctga                                              20

<210> SEQ ID NO 27

```
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 27
gtggcattca aggagtacct c                                              21

<210> SEQ ID NO 28
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 28
gccttcgatt ctggattcag aca                                            23

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
cgcccaaacc gaagtcatag                                                20

<210> SEQ ID NO 30
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 30
gctccccttg ttcagtatct ttt                                            23

<210> SEQ ID NO 31
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 31
gagagctgcg ttgcgtttg                                                 19

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 32
tttccttgtt tccaccgtcc a                                              21

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
```

```
agagctgcgt tgcacttgtt                                                    20

<210> SEQ ID NO 34
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 34
gcagtttacc aatcgttttg ggg                                                23

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 35
ccagtagtga gaaagggtcg c                                                  21

<210> SEQ ID NO 36
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 36
tggggcaaat tgtttaaggt ctt                                                23

<210> SEQ ID NO 37
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 37
agctggagtc tattcctgga tt                                                 22

<210> SEQ ID NO 38
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 38
ggctgcatat aggattccgt c                                                  21

<210> SEQ ID NO 39
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 39
cttgctgacc atttggaaaa cc                                                 22

<210> SEQ ID NO 40
<211> LENGTH: 20
<212> TYPE: DNA
```

```
<213> ORGANISM: Artificial sequence
<220> FEATURE:
<223> OTHER INFORMATION: Synthetic oligonucleotide

<400> SEQUENCE: 40
ctgtgtaggc tactcctgcc                                                   20

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 41
cggagaagct gtctgagaag t                                                 21

<210> SEQ ID NO 42
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 42
ctgaggactg tgagagatgt agt                                               23

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 43
tctctgggct acgagttcca c                                                 21

<210> SEQ ID NO 44
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 44
acgttgatct tcacattggg g                                                 21

<210> SEQ ID NO 45
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 45
actgctgggg tgttttgatg g                                                 21

<210> SEQ ID NO 46
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 46
tgtgggtata gtaccagtcc ttg                                               23
```

```
<210> SEQ ID NO 47
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 47
aaggtactct cgcaggaaat gg                                            22

<210> SEQ ID NO 48
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 48
acatactctc tcttgccttg acc                                           23

<210> SEQ ID NO 49
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 49
agccccacaa gtcttgcag                                                19

<210> SEQ ID NO 50
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 50
gctagtggta tatgtcacct cgc                                           23

<210> SEQ ID NO 51
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 51
cggcagcctc actactcag                                                19

<210> SEQ ID NO 52
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 52
tcccattttg atggcccgaa g                                             21

<210> SEQ ID NO 53
<211> LENGTH: 21
<212> TYPE: DNA
<213> ORGANISM: Artificial sequence
<220> FEATURE:
```

<223> OTHER INFORMATION: Synthetic oligonucleotide

<400> SEQUENCE: 53
ctgcctgggt tccatcttc t                                                21

<210> SEQ ID NO 54
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 54
gccattcatg tcagagctac act                                             23

<210> SEQ ID NO 55
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 55
acaccgacgg gcttttatac g                                               21

<210> SEQ ID NO 56
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 56
cccattcttc ttgaggccaa c                                               21

<210> SEQ ID NO 57
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 57
agaagagcga ccctcacatc a                                               21

<210> SEQ ID NO 58
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 58
actgcccagt tcgtttcagt g                                               21

<210> SEQ ID NO 59
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 59
tccttgcaca acgtcaccct t                                               21

-continued

```
<210> SEQ ID NO 60
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 60
gcagagtgat gagaaaaccc aa                                              22

<210> SEQ ID NO 61
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 61
acagagagtg ggtagtggtg a                                               21

<210> SEQ ID NO 62
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 62
gttcctccaa actagaagca gc                                              22

<210> SEQ ID NO 63
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 63
ctgtcatgct aatggtgtcc c                                               21

<210> SEQ ID NO 64
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 64
tgctgcttcc tggtcctaaa ata                                             23

<210> SEQ ID NO 65
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 65
atgagtctgg taggtggttt tcc                                             23

<210> SEQ ID NO 66
<211> LENGTH: 21
<212> TYPE: DNA
<213> ORGANISM: Artificial sequence
<220> FEATURE:
<223> OTHER INFORMATION: Synthetic oligonucleotide
```

```
<400> SEQUENCE: 66
catactcggg gctgtaggac a                                              21

<210> SEQ ID NO 67
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 67
tacaggggca ctgtcaatac c                                              21

<210> SEQ ID NO 68
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 68
ggatactgag aatcccaacg c                                              21

<210> SEQ ID NO 69
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 69
ggcgcgaacg acaagaaaaa g                                              21

<210> SEQ ID NO 70
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 70
ccttatcaag atgcgaactc aca                                            23

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
tcctgcgtac ctgaggtttg                                                20

<210> SEQ ID NO 72
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 72
caaccgtaac ttctcctcca c                                              21

<210> SEQ ID NO 73
<211> LENGTH: 20
```

<212> TYPE: DNA
<213> ORGANISM: Artificial sequence
<220> FEATURE:
<223> OTHER INFORMATION: Synthetic oligonucleotide

<400> SEQUENCE: 73
acgagcagca ggtaaacgtg                                              20

<210> SEQ ID NO 74
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 74
gaaggtccct gatgtagtcg at                                           22

<210> SEQ ID NO 75
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 75
agtcccgaga ggcactcag                                               19

<210> SEQ ID NO 76
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 76
gctccttttg tcgttggaga tg                                           22

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
gcctcgccct ttgctttact                                              20

<210> SEQ ID NO 78
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 78
ctgtgggtct cagggagatc a                                            21

<210> SEQ ID NO 79
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 79

```
atgaccaaca agtgtctcct cc                                              22

<210> SEQ ID NO 80
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 80
gctcatggaa agagctgtag tg                                              22

<210> SEQ ID NO 81
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 81
ctcttggctg ttactgccag g                                               21

<210> SEQ ID NO 82
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 82
ctccacactc ttttggatgc t                                               21

<210> SEQ ID NO 83
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 83
atgctcttca gttcgtgtgt g                                               21

<210> SEQ ID NO 84
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 84
gcactccctc tacttgcgtt c                                               21

<210> SEQ ID NO 85
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 85
ctcgccagtg aaatgatggc t                                               21

<210> SEQ ID NO 86
<211> LENGTH: 21
<212> TYPE: DNA
<213> ORGANISM: Artificial sequence
```

```
<220> FEATURE:
<223> OTHER INFORMATION: Synthetic oligonucleotide

<400> SEQUENCE: 86
gtcggagatt cgtagctgga t                                              21

<210> SEQ ID NO 87
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 87
aaattcggta catcctcgac gg                                             22

<210> SEQ ID NO 88
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 88
ggaaggttca ggttgttttc tgc                                            23

<210> SEQ ID NO 89
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 89
ttttgccaag gagtgctaaa ga                                             22

<210> SEQ ID NO 90
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 90
aaccctctgc acccagtttt c                                              21

<210> SEQ ID NO 91
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 91
tcgggactcc tgctacctc                                                 19

<210> SEQ ID NO 92
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 92
cacgagaaga aacatccggg a                                              21
```

```
<210> SEQ ID NO 93
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 93
aggatgactg tgtcgtcaga t                                              21

<210> SEQ ID NO 94
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 94
ggtagacgtg gcctctttat aca                                            23

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
tcgggtcagt tcgagttgga                                                20

<210> SEQ ID NO 96
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 96
aggcacactt tgaagtatgt gtc                                            23

<210> SEQ ID NO 97
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 97
ggcccaataa tcagagtggc a                                              21

<210> SEQ ID NO 98
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 98
tgtcatttcc gatcactttt gga                                            23

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 99
cccaccgagg acctttactg                                              20

<210> SEQ ID NO 100
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 100
ggtgtgcctt gttgctgtt                                               19

<210> SEQ ID NO 101
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 101
ggtgggacct gatgacgtg                                               19

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
agctcccgaa atgaggacca                                              20

<210> SEQ ID NO 103
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 103
gaaccctgtg cggattcttg t                                            21

<210> SEQ ID NO 104
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 104
tccatcttgg ataaggtcag gat                                          23

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
cgcggtcgcc aaaaagaaag                                              20

<210> SEQ ID NO 106
```

```
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 106
cagtcggctc caaactcct                                               19

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
ccgtcgccca tcatcaagtt                                              20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
ctgtctgggg cagtccaaag                                              20

<210> SEQ ID NO 109
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 109
tggcagagat gcgtggaga                                               19

<210> SEQ ID NO 110
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 110
ggcaagtctt ccgagtagtt tt                                           22

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
gggtgagacg tgccagtttc                                              20

<210> SEQ ID NO 112
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 112
```
ctgggtgtca atggagaggg a                           21

<210> SEQ ID NO 113
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 113
tggggctctc acaagacctt                             20

<210> SEQ ID NO 114
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 114
agcttgggaa tagatgaagt tgc                         23

<210> SEQ ID NO 115
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 115
gaagggaaca tgcactatga ca                          22

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
agcgttttta ccgtgggctt                             20

<210> SEQ ID NO 117
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 117
ccagcgactc ctggagatag a                           21

<210> SEQ ID NO 118
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 118
cttctcgggc acatgcttag t                           21

<210> SEQ ID NO 119
<211> LENGTH: 22
<212> TYPE: DNA

```
<213> ORGANISM: Artificial sequence
<220> FEATURE:
<223> OTHER INFORMATION: Synthetic oligonucleotide

<400> SEQUENCE: 119
aacagtgttg acatgaagag cc                                              22

<210> SEQ ID NO 120
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 120
tgtaaaacag cacgtcatcc tt                                              22

<210> SEQ ID NO 121
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 121
tgctgcggcg atgagaatc                                                  19

<210> SEQ ID NO 122
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 122
gtctcctcct ttccggctt                                                  19

<210> SEQ ID NO 123
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 123
gtgagcgact ccaaaggca                                                  19

<210> SEQ ID NO 124
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 124
gcagttgcac cagtgaatgt t                                               21

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125 caggggggctt cactgttcag                                                20
```

<210> SEQ ID NO 126
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 126
gccattatca cacattgttg ctc                                              23

<210> SEQ ID NO 127
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 127
cctgggcatg tgtcagagc                                                   19

<210> SEQ ID NO 128
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 128
ggtgttggag agtattgtgt gg                                               22

<210> SEQ ID NO 129
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 129
gtgacaagga ctcccaatgt g                                                21

<210> SEQ ID NO 130
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 130
tcttgaccca gatactgaca gc                                               22

<210> SEQ ID NO 131
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 131
ctcccaggag tacagctacg a                                                21

<210> SEQ ID NO 132
<211> LENGTH: 19
<212> TYPE: DNA
<213> ORGANISM: Artificial sequence
<220> FEATURE:

```
<223> OTHER INFORMATION: Synthetic oligonucleotide

<400> SEQUENCE: 132
ccagcaatct ggcgagaga                                                 19

<210> SEQ ID NO 133
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 133
gccctggtgc tactcctct                                                 19

<210> SEQ ID NO 134
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 134
cagcttgttc acggggactt t                                              21

<210> SEQ ID NO 135
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 135
aggctgaaat ctccttcacg c                                              21

<210> SEQ ID NO 136
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 136
gtctccagac atgaccacca g                                              21

<210> SEQ ID NO 137
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 137
acatctgctc gaacccaaac a                                              21

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
gacagcgaca tctggcaaca                                                20
```

```
<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
tgccaccctg gttttacgg                                                    20

<210> SEQ ID NO 140
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 140
ttggaagcga tcacacatct c                                                 21

<210> SEQ ID NO 141
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 141
ggccctggct gtccttatc                                                    19

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
agcaagcggt tcttcccttc                                                   20

<210> SEQ ID NO 143
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 143
ggccagatcc tgtccaagc                                                    19

<210> SEQ ID NO 144
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 144
gtgggtttcc accattagca c                                                 21

<210> SEQ ID NO 145
<211> LENGTH: 19
<212> TYPE: DNA
<213> ORGANISM: Artificial sequence
<220> FEATURE:
<223> OTHER INFORMATION: Synthetic oligonucleotide
```

```
<400> SEQUENCE: 145
ctgcatctgg tcacggtcg                                                  19

<210> SEQ ID NO 146
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 146
cctcgggctc aggatagtct                                                 20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
acggcgttac agtgtttctg                                                 20

<210> SEQ ID NO 148
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 148
gcacatacaa acggcctatc t                                               21

<210> SEQ ID NO 149
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 149
tgcctgatga caagttccaa g                                               21

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
ccagagtggt ctttccgctc                                                 20

<210> SEQ ID NO 151
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 151
acaaagacac gaccttcgac c                                               21

<210> SEQ ID NO 152
<211> LENGTH: 19
```

```
<212> TYPE: DNA
<213> ORGANISM: Artificial sequence
<220> FEATURE:
<223> OTHER INFORMATION: Synthetic oligonucleotide

<400> SEQUENCE: 152
gacttgccgt cctgcttga                                            19

<210> SEQ ID NO 153
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 153
cttctgcaat tccgacctcg t                                         21

<210> SEQ ID NO 154
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 154
ccctaaggct tggaaccctt t                                         21

<210> SEQ ID NO 155
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 155
aagcggtcag tgagaaggaa g                                         21

<210> SEQ ID NO 156
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 156
tcctcttgat agggttgcca ta                                        22

<210> SEQ ID NO 157
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 157
caactccgac atcgtgatcc g                                         21

<210> SEQ ID NO 158
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 158
```

```
gaagcctcgg tacatcttca tc                                              22

<210> SEQ ID NO 159
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 159
atgagcactg aaagcatgat cc                                              22

<210> SEQ ID NO 160
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 160
gagggctgat tagagagagg tc                                              22

<210> SEQ ID NO 161
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 161
tccccgagag cgtctttct                                                  19

<210> SEQ ID NO 162
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 162
atgtcattgg ggtagaggtt ct                                              22

<210> SEQ ID NO 163
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 163
caacatcacc atgcagatta tgc                                             23

<210> SEQ ID NO 164
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 164
gctttcgttt ttgcccttt c                                                21

<210> SEQ ID NO 165
<211> LENGTH: 21
<212> TYPE: DNA
<213> ORGANISM: Artificial sequence
```

```
<220> FEATURE:
<223> OTHER INFORMATION: Synthetic oligonucleotide

<400> SEQUENCE: 165
cacggcttat gcaagcaaag a                                              21

<210> SEQ ID NO 166
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 166
tcctttcctt agctgacact tgt                                            23

<210> SEQ ID NO 167
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 167
tgcgaacacg aatgtgtgga                                                20

<210> SEQ ID NO 168
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 168
caatctggca ctcatctgtg tc                                             22

<210> SEQ ID NO 169
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 169
tgagcaataa caagatcacg gg                                             22

<210> SEQ ID NO 170
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 170
tcggaggtga gacagccaa                                                 19

<210> SEQ ID NO 171
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 171
cctgggcatg tgtcagagc                                                 19
```

<210> SEQ ID NO 172
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 172
ggtgttggag agtattgtgt gg                                           22

<210> SEQ ID NO 173
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 173
cggtagacgc ctcttattat ggt                                          23

<210> SEQ ID NO 174
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 174 cctttccaa cttagcacct tct                                           23

<210> SEQ ID NO 175
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 175
cagtgtgccc gccaaaaac                                               19

<210> SEQ ID NO 176
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 176
tgggtgtgta ctggtcctca a                                            21

<210> SEQ ID NO 177
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 177
cgactctgaa tccccaggaa c                                            21

<210> SEQ ID NO 178
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 178
cctgcggttg ggagaagata                                              20

<210> SEQ ID NO 179
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 179
ggcattaccc cgtgaacagt                                              20

<210> SEQ ID NO 180
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 180
caccccgatg tctctgtgat                                              20

<210> SEQ ID NO 181
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 181
tggggtcact gcaccaaaat                                              20

<210> SEQ ID NO 182
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 182
gaaggtcggc ttgcacacat a                                            21

<210> SEQ ID NO 183
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 183
gaggccctaa aggtatggag c                                            21

<210> SEQ ID NO 184
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 184
cccttctcgg tgagtcttgg                                              20

<210> SEQ ID NO 185
```

```
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 185
cacattgagc cctacacgga g                                              21

<210> SEQ ID NO 186
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 186
gctgagagca tagcgcaaga t                                              21

<210> SEQ ID NO 187
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 187
tcgctctcct gctaacagtc t                                              21

<210> SEQ ID NO 188
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 188
ctcgtactgg atgggtgaac t                                              21

<210> SEQ ID NO 189
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 189
cctctgtgta ccctgctact c                                              21

<210> SEQ ID NO 190
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 190
cttcggtggc cttgttgtac t                                              21

<210> SEQ ID NO 191
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 191
```

```
ccgaaaccgg ctattcaacc t                                              21

<210> SEQ ID NO 192
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 192
cagcgaagat tcagtgcttc c                                              21

<210> SEQ ID NO 193
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 193
tagatgggag cctgtatgct aag                                            23

<210> SEQ ID NO 194
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 194
gtaggacgtg tggcattaac a                                              21

<210> SEQ ID NO 195
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 195
ctctctcgtt tcagaaaaga ggc                                            23

<210> SEQ ID NO 196
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 196
ttcctgagta acaaggggtc c                                              21

<210> SEQ ID NO 197
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 197
tactgcgagc agaaggagtg                                                20

<210> SEQ ID NO 198
<211> LENGTH: 19
<212> TYPE: DNA
```

```
<213> ORGANISM: Artificial sequence
<220> FEATURE:
<223> OTHER INFORMATION: Synthetic oligonucleotide

<400> SEQUENCE: 198
ccagcgaaat ccaccatcc                                                   19

<210> SEQ ID NO 199
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 199
agctggggtc cacagacaa                                                   19

<210> SEQ ID NO 200
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 200
gacgcctctc cacattgct                                                   19

<210> SEQ ID NO 201
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 201
gcgagcagat catcggctt                                                   19

<210> SEQ ID NO 202
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 202
tgcaaactgg tattccacat tgt                                              23

<210> SEQ ID NO 203
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 203
cgctcatcgc ccactattac c                                                21

<210> SEQ ID NO 204
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 204
tgttcagctc ttggcgctt                                                   19
```

<210> SEQ ID NO 205
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 205
agccttgtga aactgaagca t                                              21

<210> SEQ ID NO 206
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 206
ggccatccca gtccatctg                                                 19

<210> SEQ ID NO 207
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 207
gcagaccgta gccccaatg                                                 19

<210> SEQ ID NO 208
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 208
gcgtagttgt tgcggaggta                                                20

<210> SEQ ID NO 209
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 209
cggtgcctcc aagtgactg                                                 19

<210> SEQ ID NO 210
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 210
aggctgaact cctgtgacct t                                              21

<210> SEQ ID NO 211
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 211
tatgctggtt ccctggctga     20

<210> SEQ ID NO 212
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 212
ggcctcatca cactcgttg     19

<210> SEQ ID NO 213
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 213
tcttgcggtg gaacagaata ag     22

<210> SEQ ID NO 214
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 214
gcatagcccc aagcaaaagt t     21

<210> SEQ ID NO 215
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 215
gtgcataacc ggcccgaata     20

<210> SEQ ID NO 216
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 216
aaccggacag aaattcaccc c     21

<210> SEQ ID NO 217
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 217
gctcttcgta ggcggagtc     19

<210> SEQ ID NO 218
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 218
cctcatcgtc tggtagggct                                             20

<210> SEQ ID NO 219
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 219
gccaacaaga gtaagggcca g                                           21

<210> SEQ ID NO 220
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 220
cgtcatacat gaactgaagc gtc                                         23

<210> SEQ ID NO 221
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 221
ggtgaagaac ggtgggtctc                                             20

<210> SEQ ID NO 222
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 222
aatcggctca tgtgggtcat a                                           21

<210> SEQ ID NO 223
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 223 ccccctgcaaa gtctcgctc                                             19

<210> SEQ ID NO 224
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 224
aatctcgact gtaagacctg cta								23

<210> SEQ ID NO 225
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 225
acaaccgcag gtcgaattgt t								21

<210> SEQ ID NO 226
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 226
gtgactccct tgagccaca								19

<210> SEQ ID NO 227
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 227
ccagaaaaga agcgaaggaa gt								22

<210> SEQ ID NO 228
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 228
tccgaagtca tcttcaaaag gg								22

<210> SEQ ID NO 229
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 229
gccttgaaat tagcaggtct tga								23

<210> SEQ ID NO 230
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 230
ctgtagaact tcgttgtgca tct								23

<210> SEQ ID NO 231
<211> LENGTH: 19

```
<212> TYPE: DNA
<213> ORGANISM: Artificial sequence
<220> FEATURE:
<223> OTHER INFORMATION: Synthetic oligonucleotide

<400> SEQUENCE: 231
ttcgagaggc cccgttttc                                                    19

<210> SEQ ID NO 232
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 232
attggcccca tcaaaaggtt c                                                 21

<210> SEQ ID NO 233
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 233
tttgagcgtc gcagagaact t                                                 21

<210> SEQ ID NO 234
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 234
tgtcccaagg attcttcctc c                                                 21

<210> SEQ ID NO 235
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 235
cgccatttca cccagtaagc                                                   20

<210> SEQ ID NO 236
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 236
agccactctt ccataacacc c                                                 21

<210> SEQ ID NO 237
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 237
```

```
tcagctttca ccccaaaaga c                                              21

<210> SEQ ID NO 238
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 238
cacatccgat agtcccataa ctg                                            23

<210> SEQ ID NO 239
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 239
ccggcctgcg agttttag                                                  19

<210> SEQ ID NO 240
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 240
gggggaggat tctcagaagg t                                              21

<210> SEQ ID NO 241
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 241
ttcgagaggc cccgttttc                                                 19

<210> SEQ ID NO 242
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 242
attggcccca tcaaaaggtt c                                              21

<210> SEQ ID NO 243
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 243
aatatcggca ttctgtgcta cg                                             22

<210> SEQ ID NO 244
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 244
gcagggtctg tattctgggt                    20

<210> SEQ ID NO 245
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 245
gttgctggtc acattcctgg                    20

<210> SEQ ID NO 246
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 246
ggtaatccca aaagcgaccc a                  21

<210> SEQ ID NO 247
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 247
cagccccatc agcgtgatt                     19

<210> SEQ ID NO 248
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 248
gcggcttact tgtctgggac                    20

<210> SEQ ID NO 249
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 249
agaccctccc tcagttccaa t                  21

<210> SEQ ID NO 250
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 250
gggtattcgc attcttgtcc tt                 22

<210> SEQ ID NO 251
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 251
ctgctcttca acacacgata cg                                              22

<210> SEQ ID NO 252
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 252
ccctctcttg actatccacg at                                              22

<210> SEQ ID NO 253
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 253
ccaacctcct tcggagcag                                                  19

<210> SEQ ID NO 254
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 254
ctgtggtgca gtcactgtcc                                                 20

<210> SEQ ID NO 255
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 255
agctgacctc agacccgag                                                  19

<210> SEQ ID NO 256
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 256
catacgccgt gaagatgacg a                                               21

<210> SEQ ID NO 257
<211> LENGTH: 21
<212> TYPE: DNA
<213> ORGANISM: Artificial sequence
<220> FEATURE:
<223> OTHER INFORMATION: Synthetic oligonucleotide

```
<400> SEQUENCE: 257
aagaccccat tcaacaagca g                                              21

<210> SEQ ID NO 258
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 258
ccagtttcca tcttggtcac ag                                             22

<210> SEQ ID NO 259
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 259
ctgatcctcg ccgtcaagaa t                                              21

<210> SEQ ID NO 260
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 260
gttcacgttg agcctctttg t                                              21

<210> SEQ ID NO 261
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 261
ctgaggatgc cgattctgag a                                              21

<210> SEQ ID NO 262
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 262
taacggagca agaccatgag a                                              21

<210> SEQ ID NO 263
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 263
ctctgctggt tcgccaacat                                                20

<210> SEQ ID NO 264
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 264
cagctcgtac ttctgcgaca                                               20

<210> SEQ ID NO 265
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 265
ccctcccact gtatccacg                                                19

<210> SEQ ID NO 266
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 266
agtgactctc aaaaggtcca ga                                            22

<210> SEQ ID NO 267
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 267
cagcacctac cgaaccatct a                                             21

<210> SEQ ID NO 268
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 268
ccctcctagc actgcattca t                                             21

<210> SEQ ID NO 269
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 269
ctgctctttg acgctcacaa g                                             21

<210> SEQ ID NO 270
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 270
```
gtcggcctta ttcagcacg                                              19

<210> SEQ ID NO 271
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 271
caactatctg ctgggcaaat tca                                         23

<210> SEQ ID NO 272
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 272
ggcaggtctg gattgagtta tac                                         23

<210> SEQ ID NO 273
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 273
tttcacacgg cacatttgga c                                           21

<210> SEQ ID NO 274
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 274
gtggacgggg tcactatacc                                             20

<210> SEQ ID NO 275
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 275
ccagcagctc atatcaagga ag                                          22

<210> SEQ ID NO 276
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 276
gttccgtagg cacactcaaa c                                           21

<210> SEQ ID NO 277
<211> LENGTH: 19
<212> TYPE: DNA

```
<213> ORGANISM: Artificial sequence
<220> FEATURE:
<223> OTHER INFORMATION: Synthetic oligonucleotide

<400> SEQUENCE: 277
cccctggtga ccaacttgc                                                    19

<210> SEQ ID NO 278
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 278
tgggatgaag acacctcccc                                                   20

<210> SEQ ID NO 279
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 279
agcccctatg agttcttccc a                                                 21

<210> SEQ ID NO 280
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 280
gtgcctgctc tgattctaaa cc                                                22

<210> SEQ ID NO 281
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 281
tgcactgaac tggaattacg ag                                                22

<210> SEQ ID NO 282
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 282
cagccgtagg acttttttgtg g                                                21

<210> SEQ ID NO 283
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 283
caccctcgca gtctccaaaa                                                   20
```

<210> SEQ ID NO 284
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 284
gaaagcatag ccactagacg tg                                          22

<210> SEQ ID NO 285
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 285
tctgtgtccc cctcaaaagt c                                           21

<210> SEQ ID NO 286
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 286
ggggtctcta tgcccaacaa                                             20

<210> SEQ ID NO 287
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 287
cggatgagaa ggtattcgag gt                                          22

<210> SEQ ID NO 288
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 288
cacccacttc aggctggtta c                                           21

<210> SEQ ID NO 289
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 289
gagccgtgcg agttctctac                                             20

<210> SEQ ID NO 290
<211> LENGTH: 23
<212> TYPE: DNA
<213> ORGANISM: Artificial sequence
<220> FEATURE:

<223> OTHER INFORMATION: Synthetic oligonucleotide

<400> SEQUENCE: 290
ggccttaatc agaggtctct tca                                           23

<210> SEQ ID NO 291
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 291
acttttcctg ccacgactta ttc                                           23

<210> SEQ ID NO 292
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 292
atccagggaa gtgtcactgt t                                             21

<210> SEQ ID NO 293
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 293
gcccgacaac gacatcaag                                                19

<210> SEQ ID NO 294
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 294
gccaaatagg gtcgaggaag ta                                            22

<210> SEQ ID NO 295
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 295
ggaccccgtt ggacgtaac                                                19

<210> SEQ ID NO 296
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 296
cttgacctgg tacactggct t                                             21

```
<210> SEQ ID NO 297
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 297
tggcctcatt ggaaaggacc                                               20

<210> SEQ ID NO 298
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 298
ccaggcgttg cttcctcag                                                19

<210> SEQ ID NO 299
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 299
ggctgctggc agactatgg                                                19

<210> SEQ ID NO 300
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 300
tggacttggc cttgctgtta t                                             21

<210> SEQ ID NO 301
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 301
gctgaccctg cttggcttat                                               20

<210> SEQ ID NO 302
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 302
ccctcgccat accgatgtat ta                                            22

<210> SEQ ID NO 303
<211> LENGTH: 19
<212> TYPE: DNA
<213> ORGANISM: Artificial sequence
<220> FEATURE:
<223> OTHER INFORMATION: Synthetic oligonucleotide
```

<400> SEQUENCE: 303
tgcttcctga ggggaatgg                                                  19

<210> SEQ ID NO 304
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 304
atcgtggctg caccaagaaa                                                 20

<210> SEQ ID NO 305
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 305
agcctgaact cctgacacta t                                               21

<210> SEQ ID NO 306
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 306
tgcttttcgc catcattttt ctc                                             23

<210> SEQ ID NO 307
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 307
gtatgcagac acgttccgac                                                 20

<210> SEQ ID NO 308
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 308
caggcgtaga atgcgtttcc                                                 20

<210> SEQ ID NO 309
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 309
acagtcaccc ccagttatga t                                               21

<210> SEQ ID NO 310
<211> LENGTH: 21

```
<212> TYPE: DNA
<213> ORGANISM: Artificial sequence
<220> FEATURE:
<223> OTHER INFORMATION: Synthetic oligonucleotide

<400> SEQUENCE: 310
atctggacta ggttccgttg t                                            21

<210> SEQ ID NO 311
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 311
tgtgggtgac aactgttcta cc                                           22

<210> SEQ ID NO 312
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 312
agaagccaat gatacgggtg at                                           22

<210> SEQ ID NO 313
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 313
tgctcacttt ctccccgtg                                               19

<210> SEQ ID NO 314
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 314
gggcagtaac accagcacc                                               19

<210> SEQ ID NO 315
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 315
tcacagagct gcaactgaca t                                            21

<210> SEQ ID NO 316
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 316
```
aggcattggt gatttgaagc a                                     21

<210> SEQ ID NO 317
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 317
catggtgatt cttacctgct tga                                   23

<210> SEQ ID NO 318
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 318
cccacgacca ctttctcatt tt                                    22

<210> SEQ ID NO 319
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 319
tccagcaaga gtaattctcc tcc                                   23

<210> SEQ ID NO 320
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 320
gtacgtgttg ggtctccaga ta                                    22

<210> SEQ ID NO 321
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 321
tcaagacgca ccaggtgata g                                     21

<210> SEQ ID NO 322
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 322
cggtagaaga tgagggaatc agg                                   23

<210> SEQ ID NO 323
<211> LENGTH: 23
<212> TYPE: DNA
<213> ORGANISM: Artificial sequence

```
<220> FEATURE:
<223> OTHER INFORMATION: Synthetic oligonucleotide

<400> SEQUENCE: 323
ctcatgctta ttcctcccat tcc                                             23

<210> SEQ ID NO 324
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 324
agggtgggtg gatagtatgt g                                               21

<210> SEQ ID NO 325
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 325
ctgggcgctg tcctgaatc                                                  19

<210> SEQ ID NO 326
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 326
caatctcgca gggtgctata ag                                              22

<210> SEQ ID NO 327
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 327
tctggtgaac ggaaggagg                                                  19

<210> SEQ ID NO 328
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 328
cgaagaagac ttgacagagg c                                               21

<210> SEQ ID NO 329
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 329
gtgggtgagc agtttactct g                                               21
```

<210> SEQ ID NO 330
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 330
gccaggggtt tcccatcttt c    21

<210> SEQ ID NO 331
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 331
catccgggac aactcacagg    20

<210> SEQ ID NO 332
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 332
ctccaaactg atctgtcgct g    21

<210> SEQ ID NO 333
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 333
tcagccccga ggatggttt    19

<210> SEQ ID NO 334
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 334
aaggctaagt gcaaggagac a    21

<210> SEQ ID NO 335
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 335
gctccgaagc tggcaagaa    19

<210> SEQ ID NO 336
<211> LENGTH: 22
<212> TYPE: DNA
<213> ORGANISM: Artificial sequence
<220> FEATURE:
<223> OTHER INFORMATION: Synthetic oligonucleotide

```
<400> SEQUENCE: 336
gggacttgtc actatgcagg tt                                              22

<210> SEQ ID NO 337
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 337
gggcagcgac acctctacta                                                 20

<210> SEQ ID NO 338
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 338
tggaaatgag acccgatgaa gaa                                             23

<210> SEQ ID NO 339
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 339
ggctatccag cgtactccaa a                                               21

<210> SEQ ID NO 340
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 340
cggcaggcat actcatcttt tt                                              22

<210> SEQ ID NO 341
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 341
cctggcgtcg tgattagtga t                                               21

<210> SEQ ID NO 342
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 342
agacgttcag tcctgtccat aa                                              22

<210> SEQ ID NO 343
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 343
cgaggttggc tggaagtacc                                                  20

<210> SEQ ID NO 344
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 344
cttctcggcc tgtttccgta g                                                21

<210> SEQ ID NO 345
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 345
atggggaagg tgaaggtcg                                                   19

<210> SEQ ID NO 346
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 346
ggggtcattg atggcaacaa ta                                               22

<210> SEQ ID NO 347
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 347
catgtacgtt gctatccagg c                                                21

<210> SEQ ID NO 348
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 348
ctccttaatg tcacgcacga t                                                21
```